(12) United States Patent
Yeung et al.

(10) Patent No.: US 10,646,288 B2
(45) Date of Patent: May 12, 2020

(54) AUTOMATED STEERING SYSTEMS AND METHODS FOR A ROBOTIC ENDOSCOPE

(71) Applicant: Bio-Medical Engineering (HK) Limited, Hong Kong (CN)

(72) Inventors: Chung-Kwong Yeung, Hong Kong (CN); Steven Chu, Menlo Park, CA (US); Wenling Chan, Hong Kong (CN); Tin Chak Johnson Pang, Hong Kong (CN); Hon Chung Chung, Hong Kong (CN)

(73) Assignee: BIO-MEDICAL ENGINEERING (HK) LIMITED, Hong Kong (HK)

(*) Notice: Subject to any disclaimer, the term of this patent is extended or adjusted under 35 U.S.C. 154(b) by 0 days.

(21) Appl. No.: 15/928,843

(22) Filed: Mar. 22, 2018

(65) Prior Publication Data

US 2018/0296281 A1    Oct. 18, 2018

Related U.S. Application Data

(60) Provisional application No. 62/484,754, filed on Apr. 12, 2017, provisional application No. 62/535,386, filed on Jul. 21, 2017.

(51) Int. Cl.
*A61B 34/30* (2016.01)
*A61B 1/00* (2006.01)
(Continued)

(52) U.S. Cl.
CPC .......... *A61B 34/30* (2016.02); *A61B 1/00009* (2013.01); *A61B 1/31* (2013.01);
(Continued)

(58) Field of Classification Search
CPC . A61B 34/30; A61B 1/00009; A61B 2576/02; A61B 34/32; A61B 34/35;
(Continued)

(56) References Cited

U.S. PATENT DOCUMENTS 8,147,402 B2 * 4/2012 Tanaka ................. A61B 1/0005
600/103
8,167,791 B2 * 5/2012 Tanaka ............... A61B 1/00147
600/109
(Continued)

FOREIGN PATENT DOCUMENTS

CN        1836624 A       9/2006
CN        101653353 A     2/2010
(Continued)

OTHER PUBLICATIONS

Cianchetti, et al., Soft robotics technologies to address shortcomings in today's minimally invasive surgery: the STIFF-FLOP approach. Soft Robotics. 2014; 1(2): 122-131.
(Continued)

*Primary Examiner* — Ryan N Henderson
*Assistant Examiner* — Pamela F Wu
(74) *Attorney, Agent, or Firm* — Wilson Sonsini Goodrich & Rosati

(57) ABSTRACT

Systems and methods for automated steering control of a robotic endoscope, e.g., a colonoscope, are provided. The control system may comprise: a) a first image sensor configured to capture a first input data stream comprising a series of two or more images of a lumen; and b) one or more processors that are individually or collectively configured to generate a steering control output signal based on an analysis of data derived from the first input data stream using a machine learning architecture, wherein the steering control output signal adapts to changes in the data of the first input data stream in real time.

42 Claims, 33 Drawing Sheets

(51) Int. Cl.
*A61B 34/32* (2016.01)
*G06N 3/04* (2006.01)
*G06T 7/64* (2017.01)
*G06T 7/174* (2017.01)
*A61B 1/31* (2006.01)

(52) U.S. Cl.
CPC .......... *A61B 34/32* (2016.02); *G06N 3/0454* (2013.01); *G06T 7/174* (2017.01); *G06T 7/64* (2017.01); *A61B 2034/301* (2016.02); *A61B 2034/303* (2016.02); *A61B 2576/00* (2013.01); *G06K 2209/05* (2013.01); *G06T 2207/10068* (2013.01); *G06T 2207/20081* (2013.01); *G06T 2207/20084* (2013.01); *G06T 2207/30028* (2013.01)

(58) Field of Classification Search
CPC ...... A61B 2034/301–306; A61B 34/37; A61B 1/0016; A61B 1/04; A61B 1/05; A61B 1/0055; A61B 1/31; G06T 2207/10068; G06T 2207/30028; G06T 7/64; G06T 7/66; G06T 7/13; G06T 7/174; G06T 7/136; G06T 2007/20084; G06T 2007/20081; G05B 19/402; G06K 9/4604; G06K 2209/05; G06N 3/0454
USPC ................. 600/117–118, 146, 148–149, 128
See application file for complete search history.

(56) References Cited

U.S. PATENT DOCUMENTS

| | | | |
|---|---|---|---|
| 8,444,549 | B2 | 5/2013 | Viola et al. |
| 2009/0041320 | A1* | 2/2009 | Tanaka ..................... A61B 1/04 382/128 |
| 2010/0204547 | A1* | 8/2010 | Tanaka ................. A61B 1/0051 600/145 |
| 2011/0319910 | A1* | 12/2011 | Roelle ..................... A61B 34/71 606/130 |
| 2012/0158011 | A1 | 6/2012 | Sandhu et al. |
| 2015/0272423 | A1* | 10/2015 | Ito ..................... A61B 1/00009 600/476 |
| 2015/0297313 | A1 | 10/2015 | Reiter et al. |
| 2016/0184032 | A1* | 6/2016 | Romo .................... A61B 10/04 606/130 |
| 2017/0071504 | A1* | 3/2017 | Wang ..................... A61B 5/066 |
| 2018/0144214 | A1* | 5/2018 | Hsieh .................. G06K 9/6265 |

FOREIGN PATENT DOCUMENTS

| | | |
|---|---|---|
| CN | 103479320 A | 1/2014 |
| CN | 104582624 A | 4/2015 |
| CN | 105796043 A | 7/2016 |
| CN | 106169068 A | 11/2016 |
| CN | 106408610 A | 2/2017 |
| CN | 107361728 A | 11/2017 |
| WO | WO-2010114920 A1 | 10/2010 |

OTHER PUBLICATIONS

Feng, et al., A Compliant Control of a Colonoscopy Robot Based on Force Sensing. Robot, 2016; 38(2): 217-224.

Konda, et al., Endoscopes and devices to improve colon polyp detection. Gastrointestinal Endoscopy. 2015; 81(5): 1122-1129.

Kumar, et al., Design of a vision-guided microrobotic colonoscopy system. Advanced Robotics, 2000; 14(2): 87-104.

Litten, et al., Development of a colonoscopy add-on device for improvement of the intubation process. Medical Devices: Evidence and Research 2011;4:197-208.

Liu, et al., A biomimetic sensor for a crawling minirobot. Robotics and Autonomous Systems. Jul. 2006; 54(7): pp. 513-528.

PCT/CN2018/080034 International Search Report and Written Opinion dated Jul. 4, 2018.

Reilink, et al., Image-Based flexible endoscope steering. The 2010 IEEE. Oct. 10-22, 2010; pp. 2339-2344.

Yildirim, et al., Artificial neural networks in robot control systems: A survey paper. Mathematical & computational applications, 2002; 7(2): 103-112.

Chen, et al., Sensor-based guidance control of a continuum robot for a semi-autonomous. Robotics and Autonomous Systems. 2009; 57:712722.

* cited by examiner

AUTOMATED STEERING SYSTEMS AND METHODS FOR A ROBOTIC ENDOSCOPE

CROSS-REFERENCE

This application claims the benefit of U.S. Provisional Application No. 62/484,754, filed Apr. 12, 2017, and U.S. Provisional Application No. 62/535,386, filed Jul. 21, 2017, each of which is incorporated herein by reference in its entirety.

BACKGROUND

Conventional colonoscopy has been used for screening of colorectal cancer. However, as the colon is a tortuous and pliable tube with many internal ridges and sharp bends, advancement of the colonoscope is difficult and often complicated by excessive looping and stretching of the colon. This may cause significant pain and discomfort as well as a substantial risk of over-distension or even perforation of the colon. A high degree of technical expertise from the medical practitioner is therefore required for skillful manipulation of the colonoscope.

Robotics technology has advantages that can be incorporated into endoscopes for a variety of applications, including colonoscopy. For example, by exploiting soft deformable structures that are capable of moving effectively through a complex environment like the inside the colon, one can significantly reduce pain and patient discomfort while minimizing the risk of colonic perforation. However, the guidance of such robotic endoscopes may still require significant technical expertise by the medical practitioner.

Accordingly, a need exists for improved systems and methods for automated steering control of endoscopes in general, and in particular, for the steering of robotic colonoscopes. A variety of image processing-based approaches to identifying the center of the colon lumen and determining a navigation direction for an advancing colonoscope have been described in the literature (see, for example, Reilink, et al. (2010), "Image-Based Flexible Endoscope Steering", IEEE/RSJ International Conference on Intelligent Robots and Systems, Oct. 18-22, 2010, Taipei, Taiwan, page 2339; van der Stap, et al. (2012), "The Use of the Focus of Expansion for Automated Steering of Flexible Endoscopes", The Fourth IEEE RAS/EMBS International Conference on Biomedical Robotics and Biomechatronics, Roma, Italy. Jun. 24-27, 2012, page 13; Ciuti, et al. (2012), "Intra-Operative Monocular 3D Reconstruction for Image-Guided Navigation in Active Locomotion Capsule Endoscopy", IEEE RAS EMBS International Conference on Biomedical Robotics and Biomechatronics, pp. 768-774; Bell, et al. (2013), "Image Partitioning and Illumination in Image Based Pose Detection for Teloperated Flexible Endoscopes", Artificial Intelligence in Medicine 59(3):185-196; van der Stap, et al. (2013), "Towards Automated Visual Flexible Endoscope Navigation", Surg Endosc. 27(10): 3539-3547; Pullens, et al. (2016), "Colonoscopy with Robotic Steering and Automated Lumen Centralization: a Feasibility Study in a Colon Model", Endoscopy 48(3):286-290; and van der Stap, et al. (2016), "Feasibility of Automated Target Centralization in Colonoscopy", Int J Comput Assist Radiol Surg. 11(3):457-465). To date however, no single approach has been sufficiently reliable to augment or replace the know-how provided by a skilled surgeon. The present disclosure describes novel methods and systems that utilize data provided by a variety of image sensors and/or non-imaging sensors, image processing using a combination of image processing algorithms, and/or machine learning algorithms to identify the center position of the colon lumen ahead of an advancing colonoscope and determine a navigation direction. The use of a machine learning approach allows the system to simulate the surgeon's thought process in guiding the progress of the colonoscope. The disclosed methods and systems are applicable to a variety of other endoscope applications in addition to colonoscopy.

SUMMARY

Systems and methods are provided for automated steering control of a robotic endoscope, e.g., a robotic colonoscope. Various aspects of the invention described herein may be applied to any of the particular applications set forth below. The invention may be applied as an automated steering control system for a robotic colonoscopy system or any robotic or endoscopic system that requires steering control. The systems and methods may employ artificial intelligence-based control method for improved performance of the endoscopy system.

Disclosed herein are control systems for providing an adaptive steering control output signal for steering a robotic endoscope, the control systems comprising: a) a first image sensor configured to capture a first input data stream comprising a series of two or more images of a lumen; and b) one or more processors that are individually or collectively configured to generate a steering control output signal based on an analysis of data derived from the first input data stream using a machine learning architecture, wherein the steering control output signal adapts to changes in the data derived from the first input data stream in real time.

In some embodiments, the control systems further comprise at least a second image sensor configured to capture at least a second input data stream comprising a series of two or more images of the lumen, wherein the steering control output signal is based on an analysis of data derived from the first input data stream and the at least second input data stream using a machine learning architecture, and wherein the steering control output signal adapts to changes in the data derived from the first or at least second input data streams in real time. In some embodiments, the first input data stream or at least second input data stream comprise video data. In some embodiments, the first image sensor and at least second image sensor are used to provide a stereoscopic image that comprises depth information about the proximity of the walls of the lumen or other obstacles relative to the distal end of the robotic endoscope. In some embodiments, the analysis comprises a determination of the location of the center of the lumen, a determination of the location of a wall of the lumen, a determination of the location of an obstacle, a calculation of a confidence level for determining the location of the center of the lumen, a determination of a loss of or change in the integrity of lumen center position data, or any combination thereof. In some embodiments, the first image sensor is located at a steerable distal portion of the distal end of the robotic endoscope. In some embodiments, the analysis comprises performing automated image processing and feature extraction on one or more images to identify the center position of the lumen. In some embodiments, the analysis comprises performing automated image processing and feature extraction on one or more images using a combination of at least two image processing algorithms to identify the center position of the lumen. In some embodiments, the center of the lumen is not visible within the one or more images, and a predicted position for the center of the lumen is calculated based on motion vectors derived from the center positions of the lumen in two or more images previously captured by the first or at least second image sensor. In some embodiments, image feature extraction data and the predicted position of the center of the lumen are individually or collectively used to determine the position of the lumen center in real time. In some embodiments, the analysis comprises performing automated image processing on one or more images to identify areas of high light reflection and thereby determine the proximity of the lumen wall or an obstacle to the distal end of the robotic endoscope based on a relationship between light reflection and proximity. In some embodiments, the relationship is represented by a light reflection intensity gradient or color gradient map. In some embodiments, the determination of the location of the center of the lumen comprises: (i) generating a plurality of vectors, where each vector is aligned in a direction that is normal to a local segment of a contour identified in an image, and (ii) counting the number of vectors that intersect a given pixel in the image. In some embodiments, the analysis of data derived from the first input data stream comprises calculating motion vectors or light intensity gradients. In some embodiments, a confidence level for determining a location of the center of the lumen is calculated based on a moment of inertia of an image feature identified as the center of the lumen. In some embodiments, an image acquisition and processing rate for the first input data stream is at least 10 Hz. In some embodiments, an image acquisition and processing rate for the at least second input data stream is at least 10 Hz. In some embodiments, at least one of the processors is located at a steerable distal portion of the distal end of the robotic endoscope, is located external to the lumen, or is remotely coupled to the robotic endoscope. In some embodiments, the machine learning architecture is an artificial neural network, a recurrent neural network, or a recurrent convolutional neural network. In some embodiments, the neural network comprises at least 3 layers including an input layer, one or more hidden layers, and an output layer. In some embodiments, at least the first input data stream is provided as input data to the machine learning architecture, and wherein one or more parameters of the machine learning architecture are stored in a medium accessible by the one or more processors. In some embodiments, the one or more parameters are pre-stored in the medium. In some embodiments, the one or more parameters are selected according to an availability of at least the first input data stream. In some embodiments, the one or more parameters are updated dynamically based on parameters provided by one or more additional robotic endoscopes. In some embodiments, the one or more parameters of the machine learning architecture are shared with the one or more additional robotic endoscopes. In some embodiments, the analysis performed by the machine learning architecture is refined using one or more sets of training data as input. In some embodiments, the analysis performed by the machine learning architecture is refined based on repeated use by a skilled operator. In some embodiments, the steering control output signal is used to control one or more actuators of the robotic endoscope. In some embodiments, the one or more actuators effect a movement of a steerable distal portion of the robotic endoscope. In some embodiments, the movement of the steerable distal portion is effected about one or more axes of rotation comprising a roll axis, a yaw axis, a pitch axis, or any combination thereof. In some embodiments, the one or more actuators are selected from a hydraulic actuator, a pneumatic actuator, or a tendon-driven actuator mechanism. In some embodiments, the one or more processors are further configured to generate a steering control output signal to direct the robotic endoscope to search along a specified route when a confidence level for determining the location of the center of the lumen relative to the distal end of the robotic endoscope is below a first threshold, and to repeat the steps of (i) performing automated image processing and feature extraction on one or more images of at least the first input data stream to identify the center position of the lumen, (ii) calculating a new confidence level for the determination of the center position of the lumen, and (iii) generating the steering control output signal to direct the robotic endoscope to search along the specified route until the new confidence level is above a second threshold. In some embodiments, the confidence level is calculated based on an intensity calculation, a moment of inertia calculation, and/or a convexity calculation for the lumen center position determined from the first input data stream. In some embodiments, the specified route is a pre-determined route selected from the group consisting of a spiral route, a rectilinear grid pattern, a circular pattern, a two-dimensional route, a three-dimensional route, or any combination thereof. In some embodiments, the specified route is determined by the machine learning architecture. In some embodiments, the specified route is automatically selected based on an analysis of the first input data stream. In some embodiments, the robotic endoscope is a robotic colonoscope. In some embodiments, the robotic colonoscope is a soft robotic colonoscope.

Also disclosed herein are methods for providing an adaptive steering control output signal for steering a robotic endoscope, the methods comprising: a) providing a first input data stream comprising a series of two or more images; and b) generating a steering control output signal based on an analysis of data derived from the first input data stream using a machine learning architecture, wherein the steering control output signal adapts to changes in the data of the first data stream in real time.

In some embodiments, the methods further comprise providing at least a second input data stream comprising a series of two or more images, wherein the steering control output signal is based on an analysis of data derived from the first input data stream and the at least second input data stream using a machine learning architecture, and wherein the steering control output signal adapts to changes in the data derived from the first or at least second input data streams in real time. In some embodiments, the first input data stream or at least second input data stream comprise video data. In some embodiments, the analysis comprises a determination of the location of the center of the lumen, a determination of the location of a wall of the lumen, a determination of the location of an obstacle, a calculation of a confidence level for determining the location of the center of the lumen, a determination of a loss of or change in the integrity of lumen center position data, or any combination thereof. In some embodiments, the first input data stream is captured by an image sensor located at a steerable distal portion of the distal end of the robotic endoscope. In some embodiments, the first input data stream and at least second input data stream are both captured by a single image sensor located at a steerable distal portion of the distal end of the robotic endoscope. In some embodiments, the first input data stream and at least second input data stream are captured by a first image sensor and an at least second image sensor located at a steerable distal portion of the distal end of the robotic endoscope. In some embodiments, the analysis comprises performing automated image processing and feature extraction on one or more images to identify the center position of the lumen. In some embodiments, the analysis comprises performing automated image processing and feature extraction on one or more images using a combination of at least two image processing algorithms to identify the center position of the lumen. In some embodiments, the center of the lumen is not visible within the one or more images, and the center position of the lumen is calculated based on motion vectors derived from the center positions of the lumen in two or more images previously captured by the first or at least second image sensor. In some embodiments, image feature extraction data and the predicted position of the center of the lumen are individually or collectively used to determine the position of the lumen center in real time. In some embodiments, the analysis comprises performing automated image processing on one or more images to identify areas of high light reflection and thereby determine the proximity of the lumen wall or an obstacle to the distal end of the robotic endoscope based on a relationship between light reflection and proximity. In some embodiments, the relationship is represented by a light reflection intensity gradient or color gradient map. In some embodiments, the first image sensor and at least second image sensor are used to provide a stereoscopic image that comprises depth information about the proximity of the walls of the lumen or other obstacles relative to the distal end of the robotic endoscope. In some embodiments, the determination of the location of the center of the lumen comprises: (i) generating a plurality of vectors, where each vector is aligned in a direction that is normal to a local segment of a contour identified in an image, and (ii) counting the number of vectors that intersect a given pixel in the image. In some embodiments, the analysis of data derived from the first input data stream comprises calculating motion vectors or light intensity gradients. In some embodiments, a confidence level for determining a location of the center of the lumen is calculated based on a moment of inertia of an image feature identified as the center of the lumen. In some embodiments, the steering control output signal is updated at a rate of at least 10 Hz. In some embodiments, the steering control output signal is updated at a rate of at least 100 Hz. In some embodiments, the machine learning architecture is an artificial neural network, a recurrent neural network, or a recurrent convolutional neural network. In some embodiments, the neural network comprises at least 3 layers including an input layer, one or more hidden layers, and an output layer. In some embodiments, at least the first input data stream is provided as input data to the machine learning architecture, and wherein one or more parameters of the machine learning architecture are stored in a medium accessible by one or more processors configured to implement the machine learning architecture. In some embodiments, the one or more parameters are pre-stored in the medium. In some embodiments, the one or more parameters are selected according to an availability of at least the first input data stream. In some embodiments, the one or more parameters are updated dynamically based on parameters provided by one or more additional robotic endoscopes. In some embodiments, the one or more parameters of the machine learning architecture are shared with the one or more additional robotic endoscopes. In some embodiments, the analysis performed by the machine learning architecture is refined using one or more sets of training data as input. In some embodiments, the analysis performed by the machine learning architecture is refined based on repeated use by a skilled operator. In some embodiments, the steering control output signal is used to control one or more actuators of the robotic endoscope. In some embodiments, the one or more actuators effect a movement of a steerable distal portion of the robotic endoscope. In some embodiments, the movement of the steerable distal portion is effected about one or more axes of rotation comprising a roll axis, a yaw axis, a pitch axis, or any combination thereof. In some embodiments, the one or more actuators are selected from a hydraulic actuator, a pneumatic actuator, or a tendon-driven actuator mechanism. In some embodiments, the method further comprises generating a steering control output signal to direct the robotic endoscope to search along a specified route when a confidence level for determining the location of the center of the lumen relative to the distal end of the robotic endoscope is below a first threshold, and repeating the steps of (i) performing automated image processing and feature extraction on one or more images of at least the first input data stream to identify the center position of the lumen, (ii) calculating a new confidence level for the determination of the center position of the lumen, and (iii) generating the steering control output signal to direct the robotic endoscope to search along the specified route until the new confidence level is above a second threshold. In some embodiments, the confidence level is calculated based on an intensity calculation, a moment of inertia calculation, and/or a convexity calculation for the lumen center position determined from the first input data stream. In some embodiments, the specified route is a pre-determined route selected from the group consisting of a spiral route, a rectilinear grid pattern, a circular pattern, a two-dimensional route, a three-dimensional route, or any combination thereof. In some embodiments, the specified route is determined by the machine learning architecture. In some embodiments, the specified route is automatically selected based on an analysis of the first input data stream. In some embodiments, the robotic endoscope is a robotic colonoscope. In some embodiments, the robotic colonoscope is a soft robotic colonoscope.

Disclosed herein are robotic endoscopes, comprising: a) an elongated body structure comprising one or more actuation units and a steerable distal portion; and b) a control system comprising: i) a first image sensor configured to capture a first input data stream comprising a series of two or more images of a lumen; and ii) one or more processors that are individually or collectively configured to generate a steering control output signal to control the one or more actuation units based on an analysis of data derived from the first input data stream using a machine learning architecture, wherein the steering control output signal adapts to changes in the data derived from the first input data stream in real time.

In some embodiments, the elongated body structure further comprises one or more wires that are driven by the one or more actuation units to steer the steerable distal portion. In some embodiments, the elongated body structure comprises an elongated elastomeric body structure. In some embodiments, the robotic endoscopes further comprise at least a second image sensor configured to capture at least a second input data stream comprising a series of two or more images of the lumen, wherein the steering control output signal is based on an analysis of data derived from the first input data stream and the at least second input data stream using a machine learning architecture, and wherein the steering control output signal adapts to changes in the data derived from the first or at least second input data streams in real time. In some embodiments, the first input data stream or at least second input data stream comprise video data. In some embodiments, the first image sensor and at least second image sensor are used to provide a stereoscopic image that comprises depth information about the proximity of the walls of the lumen or other obstacles relative to the distal end of the robotic endoscope. In some embodiments, the analysis comprises a determination of the location of the center of the lumen, a determination of the location of a wall of the lumen, a determination of the location of an obstacle, a calculation of a confidence level for determining the location of the center of the lumen, a determination of a loss of or change in the integrity of lumen center position data, or any combination thereof. In some embodiments, the first image sensor is located at the steerable distal portion of the robotic endoscope. In some embodiments, the analysis comprises performing automated image processing and feature extraction on one or more images to identify the center position of the lumen. In some embodiments, the analysis comprises performing automated image processing and feature extraction on one or more images using a combination of at least two image processing algorithms to identify the center position of the lumen. In some embodiments, the center of the lumen is not visible within the one or more images, and a predicted position for the center of the lumen is calculated based on motion vectors derived from the center positions of the lumen in two or more images previously captured by the first or at least second image sensor. In some embodiments, image feature extraction data and the predicted position of the center of the lumen are individually or collectively used to determine the position of the lumen center in real time. In some embodiments, the analysis comprises performing automated image processing on one or more images to identify areas of high light reflection and thereby determine the proximity of the lumen wall or an obstacle to the distal end of the robotic endoscope based on a relationship between light reflection and proximity. In some embodiments, the relationship is represented by a light reflection intensity gradient or color gradient map. In some embodiments, the determination of the location of the center of the lumen comprises: (i) generating a plurality of vectors, where each vector is aligned in a direction that is normal to a local segment of a contour identified in an image, and (ii) counting the number of vectors that intersect a given pixel in the image. In some embodiments, the analysis of data derived from the first input data stream comprises calculating motion vectors or light intensity gradients. In some embodiments, a confidence level for determining a location of the center of the lumen is calculated based on a moment of inertia of an image feature identified as the center of the lumen. In some embodiments, an image acquisition and processing rate for the first input data stream is at least 10 Hz. In some embodiments, an image acquisition and processing rate for the at least second input data stream is at least 10 Hz. In some embodiments, at least one of the processors is located at a steerable distal portion of the distal end of the robotic endoscope, is located external to the lumen, or is remotely coupled to the robotic endoscope. In some embodiments, the machine learning architecture is an artificial neural network, a recurrent neural network, or a recurrent convolutional neural network. In some embodiments, the neural network comprises at least 3 layers including an input layer, one or more hidden layers, and an output layer. In some embodiments, at least the first input data stream is provided as input data to the machine learning architecture, and wherein one or more parameters of the machine learning architecture are stored in a medium accessible by the one or more processors. In some embodiments, the one or more parameters are pre-stored in the medium. In some embodiments, the one or more parameters are selected according to an availability of at least the first input data stream. In some embodiments, the one or more parameters are updated dynamically based on parameters provided by one or more additional robotic endoscopes. In some embodiments, the one or more parameters of the machine learning architecture are shared with the one or more additional robotic endoscopes. In some embodiments, the analysis performed by the machine learning architecture is refined using one or more sets of training data as input. In some embodiments, the analysis performed by the machine learning architecture is refined based on repeated use by a skilled operator. In some embodiments, the one or more actuators effect a movement of a steerable distal portion of the robotic endoscope. In some embodiments, the movement of the steerable distal portion is effected about one or more axes of rotation comprising a roll axis, a yaw axis, a pitch axis, or any combination thereof. In some embodiments, the one or more actuators are selected from a hydraulic actuator, a pneumatic actuator, or a tendon-driven actuator mechanism. In some embodiments, the steering control output signal is updated at a rate of at least 10 Hz. In some embodiments, the steering control output signal is updated at a rate of at least 100 Hz. In some embodiments, the distal end of the robotic endoscope further comprises one or more light sources to provide illumination. In some embodiments, the one or more light sources comprise light emitting diodes (LEDs). In some embodiments, the steerable distal portion of the robotic colonoscope comprises one or more optical fibers that are coupled to one or more light sources located external to the colon lumen. In some embodiments, the one or more processors are further configured to generate a steering control output signal to direct the steerable distal portion of the robotic endoscope to search along a specified route when a confidence level for determining the location of the center of the lumen relative to the distal end of the robotic endoscope is below a first threshold, and to repeat the steps of (i) performing automated image processing and feature extraction on one or more images of at least the first input data stream to identify the center position of the lumen, (ii) calculating a new confidence level for the determination of the center position of the lumen, and (iii) generating the steering control output signal to direct the robotic endoscope to search along the specified route until the new confidence level is above a second threshold. In some embodiments, the confidence level is calculated based on an intensity calculation, a moment of inertia calculation, and/or a convexity calculation for the lumen center position determined from the first input data stream. In some embodiments, the specified route is a pre-determined route selected from the group consisting of a spiral route, a rectilinear grid pattern, a circular pattern, a two-dimensional route, a three-dimensional route, or any combination thereof. In some embodiments, the specified route is determined by the machine learning architecture. In some embodiments, the specified route is automatically selected based on an analysis of the first input data stream. In some embodiments, the robotic endoscope is a robotic colonoscope. In some embodiments, the robotic colonoscope is a soft robotic colonoscope.

In one aspect of the invention, a control system for providing an adaptive steering control output signal for steering a robotic endoscope is provided. The control system may comprise: a) a first sensor configured to provide a first input data, wherein the first input data stream comprises data relating to the position of the distal end of the robotic endoscope relative to the center of a lumen, relative to the walls of the lumen, relative to other obstacles, or any combination thereof; and b) a processor that is configured to generate a steering control output signal based on an analysis of the first input data stream using a machine learning architecture, wherein the steering control output signal adapts to changes in the data of the first data stream in real time.

In some embodiments, the system may further comprise at least a second sensor configured to provide at least a second input data stream, wherein the at least second input data stream comprises data relating to the position of the distal end of the robotic endoscope relative to the center of the lumen, relative to the walls of the lumen, relative to other obstacles, or any combination thereof, that is different from the first input data stream; and wherein the processor is configured to generate a steering control output signal based on an analysis of the first and at least second data streams using the machine learning architecture, wherein the steering control output signal adapts to changes in any one of the first or at least second data streams, or combinations thereof, in real time. In some cases, the first sensor is an image sensor. In some cases, both the first sensor and the at least second sensor are image sensors. In some instances, the image sensors are configured to acquire image data or video data. In some embodiments, the first sensor is located at a steerable distal portion of the distal end of the robotic endoscope.

In some cases, the first input data stream comprises data that is obtained by performing automated image processing and feature extraction on one or more image frames to identify the center position of the lumen. In some instances, the center of the lumen is not visible within at least one of the one or more image frames, and the center position of the lumen is calculated based on motion vectors. In some cases, the first input data stream comprises data that is obtained by performing automated image processing on one or more image frames to identify areas of high light reflection and thereby determine the proximity of the lumen wall or an obstacle to the distal end of the robotic endoscope based on a relationship between light reflection and proximity, and in some examples the relationship is represented by a light reflection intensity gradient or color gradient map.

In some cases, the first image sensor and at least second image sensor are used to provide a stereoscopic image that comprises depth information about the lumen proximal to the distal end of the robotic endoscope. In some instances, the depth information is indicative of a proximity of the walls of the lumen or other obstacles relative to the distal end of the robotic endoscope. In some instances, the first input data stream comprises data that is obtained by performing automated image processing and feature extraction on one or more stereoscopic image frames to identify the center position of the lumen. In some situations, the center of the lumen is not visible within at least one of the one or more stereoscopic image frames, and the center position of the colon lumen is calculated based on motion vectors. In some cases, the first input data stream comprises data that is obtained by performing automated image processing on one or more stereoscopic image frames to identify areas of high light reflection and thereby determine the proximity of the lumen wall or an obstacle to the distal end of the robotic endoscope based on a relationship between light reflection and proximity, and the relationship in some examples is represented by a light reflection intensity gradient or color gradient map. In some instances, the at least second sensor is a proximity sensor such as a capacitive touch sensor that comprises multiple sensing electrodes. In some examples, the proximity sensor is located at a steerable distal portion of the distal end of the robotic endoscope.

In some embodiments, an image acquisition and processing rate for the first data stream is at least 10 Hz and for the at least second data stream is at least 10 Hz. In some embodiments, the processor is located at a steerable distal portion of the distal end of the robotic endoscope or is located external to the lumen. In some embodiments, the processor is remotely coupled to the robotic endoscope.

In some embodiments, the machine learning architecture is implemented as a neural network. In some cases, the neural network comprises at least 3 layers. In some cases, the at least 3 layers include an input layer, one or more hidden layers, and an output layer. In some cases, the at least first input data stream is provided as input data to the machine learning architecture, and wherein one or more parameters of the machine learning architecture are stored in a medium accessible by the processor. In some instances, the one or more parameters are pre-stored in the medium and the one or more parameters are selected according to an availability of the input data stream. In some instances, the one or more parameters are updated dynamically based on parameters provided by one or more additional robotic endoscopes. In some cases, the one or more parameters of the machine learning architecture are shared with the one or more additional robotic endoscopes. In some embodiments, the machine learning architecture is linked to an internet cloud-based database. In some embodiments, the analysis performed by the machine learning architecture is refined using one or more sets of training data as input. In some embodiments, the analysis performed by the machine learning architecture is refined based on repeated use by a skilled operator.

In some embodiments, the steering control output signal is used to control one or more actuators of the robotic endoscope. In some cases, the one or more actuators effect a movement of a steerable distal portion of the robotic endoscope. In some cases, the movement of the steerable distal portion is effected about one or more axes of rotation such as a roll axis, a yaw axis, a pitch axis, or any combination thereof. In some cases, the one or more actuators are selected from a hydraulic actuator, a pneumatic actuator, or a tendon-driven actuator mechanism.

In some embodiments, the robotic endoscope is a robotic colonoscope. In some embodiments, the robotic colonoscope is a soft robotic colonoscope.

In another aspect of the invention, a robotic colonoscope system is provided. The robotic colonoscope system may comprise: a) an elongated elastomeric body structure comprising one or more actuation units and a steerable distal portion; and b) a control system comprising: i) a first sensor configured to provide a first input data stream, wherein the first input data stream comprises data relating to the position of the steerable distal portion relative to the center of a colon lumen, relative to the walls of the colon lumen, relative to other obstacles, or any combination thereof; and ii) a processor that is configured to generate a steering control output signal to control the one or more actuation units based on an analysis of the first input data stream using a machine learning architecture, wherein the steering control output signal adapts to changes in the data of the first data stream in real time.

In some embodiments, the robotic colonoscope system further comprises at least a second sensor configured to provide a second input data stream, wherein the at least second input data stream comprises data relating to the position of the steerable distal portion relative to the center of the colon lumen, relative to the walls of the colon lumen, relative to other obstacles, or any combination thereof, that is different from the first input data stream; and wherein the processor is configured to generate a steering control output signal based on an analysis of the first and at least second data streams using the machine learning architecture, wherein the steering control output signal adapts to changes in any one of the first or at least second data streams, or combinations thereof, in real time.

In some embodiments, the first sensor is an image sensor or a proximity sensor. In some cases, both the first sensor and the at least second sensor are image sensors. In some instances, the image sensors are configured to acquire image data or video data.

In some embodiments, the first sensor is located at the steerable distal portion of the robotic colonoscope and the distal end of the robotic colonoscope further comprises one or more light sources to provide illumination. In some cases, the one or more light sources comprise light emitting diodes (LEDs). In some cases, the steerable distal portion of the robotic colonoscope comprises one or more optical fibers that are coupled to one or more light sources located external to the colon lumen. In some cases, the first input data stream comprises data that is obtained by performing automated image processing and feature extraction on one or more image frames to identify the center position of the colon lumen. In some situations, the center of the colon lumen is not visible within at least one of the one or more image frames, and the center position of the colon lumen is calculated based on motion vectors. In some cases, the first input data stream comprises data that is obtained by performing automated image processing on one or more image frames to identify areas of high light reflection and thereby determine the proximity of the lumen wall or an obstacle to the distal end of the robotic colonoscope based on a relationship between light reflection and proximity and the relationship is represented by a light reflection intensity gradient or color gradient map.

In some cases, the first image sensor and at least second image sensor are used to provide a stereoscopic image that comprises depth information about the colon lumen proximal to the distal end of the robotic colonoscope. In some cases, the depth information is indicative of the proximity of the walls of the lumen or other obstacles relative to the distal end of the robotic colonoscope. In some cases, the first input data stream comprises data that is obtained by performing automated image processing and feature extraction on one or more stereoscopic image frames to identify the center position of the colon lumen. In some situations, the center of the colon lumen is not visible within at least one of the one or more stereoscopic image frames, and the center position of the colon lumen is calculated based on motion vectors. In some cases, the first input data stream comprises data that is obtained by performing automated image processing on one or more stereoscopic image frames to identify areas of high light reflection and thereby determine the proximity of the lumen wall or an obstacle to the distal end of the robotic colonoscope based on a relationship between light reflection and proximity and the relationship is represented by a light reflection intensity gradient or color gradient map.

In some embodiments, the machine learning architecture is implemented as a neural network. In some cases, the neural network comprises at least 3 layers. In some cases, the at least 3 layers include an input layer, one or more hidden layers, and an output layer. In some cases, the at least first input data stream is provided as input data to the machine learning architecture, and wherein one or more parameters of the machine learning architecture are stored in a medium accessible by the processor. In some instances, the one or more parameters are pre-stored in the medium and the one or more parameters are selected according to an availability of the input data stream. In some instances, the one or more parameters are updated dynamically based on parameters provided by one or more additional robotic endoscopes. In some cases, the one or more parameters of the machine learning architecture are shared with the one or more additional robotic endoscopes. In some embodiments, the machine learning architecture is linked to an internet cloud-based database. In some embodiments, the analysis performed by the machine learning architecture is refined using one or more sets of training data as input. In some embodiments, the analysis performed by the machine learning architecture is refined based on repeated use by a skilled operator.

In some embodiments, the steering control output signal is used to control one or more actuators of the robotic endoscope. In some cases, the one or more actuators effect a movement of a steerable distal portion of the robotic endoscope. In some cases, the movement of the steerable distal portion is effected about one or more axes of rotation such as a roll axis, a yaw axis, a pitch axis, or any combination thereof. In some cases, the one or more actuators are selected from a hydraulic actuator, a pneumatic actuator, or a tendon-driven actuator mechanism.

In some embodiments, the robotic endoscope is a robotic colonoscope. In some embodiments, the robotic colonoscope is a robotic colonoscope.

In a separate yet related aspect, a method for providing an adaptive steering control output signal for steering a robotic colonoscope is provided. The method comprises: a) providing a first input data stream, wherein the first input data stream comprises data relating to the position of the distal end of the robotic endoscope relative to the center of a lumen, relative to the walls of the lumen, relative to other obstacles, or any combination thereof; and b) generating a steering control output signal based on an analysis of the first input data stream using a machine learning architecture, wherein the steering control output signal adapts to changes in the data of the first data stream in real time.

In some embodiments, the method further comprises providing at least a second input data stream, wherein the at least second input data stream comprises data relating to the position of the distal end of the robotic endoscope relative to the center of the lumen, relative to the walls of the lumen, relative to other obstacles, or any combination thereof, that is different from the first input data stream; and wherein the steering control output signal adapts to changes in any one of the first or second data streams, or combinations thereof, in real time. In some cases, the first data stream and at least second input data stream are both captured by a single image sensor located at a steerable distal portion of the distal end of the robotic endoscope. In alternatively cases, the first data stream and at least second input data stream are captured by a first image sensor and an at least second image sensor located at a steerable distal portion of the distal end of the robotic endoscope. In some cases, the image sensors are configured to acquire image data or video data. In some cases, the first input data stream comprises data that is obtained by performing automated image processing and feature extraction on one or more image frames. In some cases, the center of the lumen is not visible within at least one of the one or more image frames, and the center position of the lumen is calculated based on motion vectors. In some instances, the first input data stream comprises data that is obtained by performing automated image processing on one or more image frames to identify areas of high light reflection and thereby determine the proximity of the lumen wall or an obstacle to the distal end of the robotic endoscope based on a relationship between light reflection and proximity and the relationship is represented by a light reflection intensity gradient or color gradient map.

In some cases, the first image sensor and at least second image sensor are used to provide a stereoscopic image that comprises depth information about the colon lumen proximal to the distal end of the robotic colonoscope. In some cases, the depth information is indicative of a proximity of the walls of the lumen or other obstacles relative to the distal end of the robotic colonoscope. In some cases, the first input data stream comprises data that is obtained by performing automated image processing and feature extraction on one or more stereoscopic image frames to identify the center position of the colon lumen. In some situations, the center of the colon lumen is not visible within at least one of the one or more stereoscopic image frames, and the center position of the colon lumen is calculated based on motion vectors. In some cases, the first input data stream comprises data that is obtained by performing automated image processing on one or more stereoscopic image frames to identify areas of high light reflection and thereby determine the proximity of the lumen wall or an obstacle to the distal end of the robotic colonoscope based on a relationship between light reflection and proximity and the relationship is represented by a light reflection intensity gradient or color gradient map.

In some embodiments, the machine learning architecture is implemented as a neural network. In some cases, the neural network comprises at least 3 layers. In some cases, the at least 3 layers include an input layer, one or more hidden layers, and an output layer. In some cases, the at least first input data stream is provided as input data to the machine learning architecture, and wherein one or more parameters of the machine learning architecture are stored in a medium accessible by the processor. In some instances, the one or more parameters are pre-stored in the medium and the one or more parameters are selected according to an availability of the input data stream. In some instances, the one or more parameters are updated dynamically based on parameters provided by one or more additional robotic endoscopes. In some cases, the one or more parameters of the machine learning architecture are shared with the one or more additional robotic endoscopes. In some embodiments, the machine learning architecture is linked to an internet cloud-based database. In some embodiments, the analysis performed by the machine learning architecture is refined using one or more sets of training data as input. In some embodiments, the analysis performed by the machine learning architecture is refined based on repeated use by a skilled operator.

In some embodiments, the steering control output signal is used to control one or more actuators of the robotic endoscope. In some cases, the one or more actuators effect a movement of a steerable distal portion of the robotic endoscope. In some cases, the movement of the steerable distal portion is effected about one or more axes of rotation such as a roll axis, a yaw axis, a pitch axis, or any combination thereof. In some cases, the one or more actuators are selected from a hydraulic actuator, a pneumatic actuator, or a tendon-driven actuator mechanism.

In some embodiments, the robotic endoscope is a robotic colonoscope. In some embodiments, the robotic colonoscope is a soft robotic colonoscope.

In another aspect, a method for using a machine learning architecture to optimize an automated colonoscope steering mechanism is provided. The method comprises: a) providing two or more sets of input sensor data obtained from two or more different types of sensors; b) providing a plurality of training datasets, wherein a training dataset comprises at least a first set of known input sensor data for each of the two or more different types of sensors and a corresponding set of known output steering control signals; and c) analyzing the plurality of training datasets using the machine learning architecture to determine a set of weighting parameters, wherein the weighting parameters are subsequently used by the machine learning architecture to provide a steering control signal for the automated colonoscope steering mechanism that is adaptive to changes in the two or more sets of input sensor data.

In some embodiments, the first set of input sensor data is provided by a proximity sensor or an image sensor. In some embodiments, the input sensor data are derived from at least one proximity sensor and at least one image sensor and the input sensor data comprises information indicative of a center position of a colon lumen, proximity of a guiding portion of a robotic colonoscope to a wall of the colon lumen, or a location of an obstacle relative to a guiding portion of a robotic colonoscope. In some cases, the information indicative of the center position of the colon lumen is obtained by analyzing an image of the colon lumen, or by calculating a predicted center position of the colon lumen based on analyzing two or more images of the colon lumen. In some instances, a change in the integrity of center position data comprises a failure of an automated image feature extraction step to identify a center position of the colon lumen or the failure of the automated image processing step to identify an obstacle, and results in the machine learning architecture providing a steering control signal that is based on proximity sensor data only.

In some embodiments, the output steering control signals of the training datasets are obtained from sets of empirical steering control instructions provided to the steering mechanism of a robotic colonoscope. In some cases, the empirical steering control instructions are generated in response to the input sensor data of the training datasets by one or more trained operators of the robotic colonoscope. The output steering control signals are for controlling one or more actuation units of a robotic colonoscope. In some embodiments, the output steering control signals are indicative of a navigation direction and the navigation direction needs not be aligned with a center position of a colon lumen. In some embodiments, the robotic endoscope is a soft robotic colonoscope.

In another aspect, a control system for providing an adaptive steering control output signal for steering a robotic colonoscope is provided. The control system comprises: a) one or more image sensors configured to capture two or more images of a colon lumen; and b) one or more processors that are individually or collectively configured to (i) perform automated feature extraction on the series of two or more images to determine a center position of the colon lumen, (ii) perform automated image processing on the series of two or more images to identify a location of a colon lumen wall or other obstacle that is in close proximity to an distal end of the robotic colonoscope based on areas of high light reflection, and (iii) determine a navigation direction that directs the robotic colonoscope towards the center position of the colon lumen using a machine learning architecture-based analysis of the center positions and locations determined in steps (i) and (ii), wherein the machine learning architecture-based analysis provides a steering control output signal that adapts to loss of or changes in the integrity of center position or location data.

In some embodiments, the control system further comprises the use of proximity sensor data to determine the navigation direction and the navigation direction may or may not be aligned with a center of the colon lumen. In some embodiments, a loss of or change in the integrity of center position data comprises a failure of the automated image feature extraction step to identify a center position of the colon lumen or the failure of the automated image processing step to identify an obstacle, and results in the machine learning architecture providing a steering control signal that is based on proximity sensor data only. In some embodiments, a predicted center position of the colon lumen is calculated from motion vectors obtained from the center positions of the colon lumen obtained by automated processing of two or more images previously captured by one or more optical image sensors. In some cases, the image feature extraction data and the predicted lumen center position data are individually or collectively used to determine the position of the lumen center in real time.

In as separate yet related aspect, a method for providing an adaptive steering control output signal for steering a robotic colonoscope is provided. The method comprises: a) providing two or more images of a colon lumen; b) performing automated feature extraction on the series of two or more images to determine a center position of the colon lumen; c) performing automated image processing on the series of two or more images to identify a location of a colon lumen wall or other obstacle that is in close proximity to an distal end of the robotic colonoscope based on areas of high light reflection; and d) determining a navigation direction that directs the robotic colonoscope towards the center position of the colon lumen using a machine learning architecture-based analysis of the center positions and locations determined in steps (b) and (c), wherein the machine learning architecture-based analysis provides a steering control output signal that adapts to loss of or changes in the integrity of center position or location data.

In another aspect, a control system for tracking an object of interest by providing an adaptive steering control output signal to a robotic endoscope is provided. The control system may comprise: a) a first image sensor configured to provide a first image data stream, wherein the first image data stream comprises data relating to a position of the object of interest within a field-of-view of the first image sensor; and b) a processor that is configured to generate a steering control output signal based on an analysis of the first image data stream using a machine learning architecture such that the object of interest has a substantially fixed position relative to the field-of-view of the first image sensor, and wherein the steering control output signal adapts to changes in the data of the first image data stream in real time.

In some embodiments, the first image data stream is a video data stream. In some cases, the object of interest is automatically positioned in the center of the field-of-view or at a location within the field-of-view that is determined by a user or by the machine learning architecture. In some cases, the object of interest is recognized using an automated image feature extraction comprising at least one of the following methods: intensity level analysis, contour mapping, noise removal, and computation of a center of mass process, or automated light intensity gradient analysis process. In some cases, the object of interest is recognized by performing additional image data processing using the machine learning architecture of step (b).

The method may further comprise determining a confidence level for the recognition of the object of interest. The confidence level is determined based on at least one of the following: intensity, moment of inertia, or convexity of the image of the object of interest. The method may further comprise calculating a motion direction vector for the object of interest relative to a steering direction for the robotic endoscope.

In some embodiments, the first image sensor is located at a steerable distal portion of the distal end of the robotic endoscope. The first image data stream further comprises data relating to the position of the distal end of the robotic endoscope relative to a center position of a lumen, a wall of the lumen, or an obstacle. The data relating to the position of the distal end of the robotic endoscope relative to the center position of the lumen, the wall of the lumen, or an obstacle is obtained by performing automated image processing and feature extraction on one or more image frames to identify the center of the lumen and/or by performing automated analysis of light intensity gradients in one or more image frames to identify the center of the lumen. In some cases, the method further comprises determining a confidence level for the identification of the center of the lumen. The confidence level is determined based on at least one of the following: intensity, moment of inertia, or convexity of the image of the center of the lumen.

In some cases, the steering control signal is adjusted to align the steering direction of the robotic endoscope with the motion direction vector of the object of interest. In some embodiments, the system may further comprise a second sensor configured to provide a second data stream, wherein the second data stream comprises data relating to a position of the distal end of the robotic endoscope relative to a center position of a lumen, a wall of the lumen, or another obstacle. The second sensor in some embodiments is a proximity sensor. For example, the proximity sensor is a capacitive touch sensor that comprises multiple sensing electrodes. The proximity sensor is located at a steerable distal portion of the distal end of the robotic endoscope. In some embodiments, the steering control output signal is generated based on an analysis of both the first image data stream and the second data stream.

In some embodiments, the steering control system may further comprise at least a third sensor configured to provide at least a third data stream, wherein the at least third data stream comprises data relating to the position of a segment of a main body of the robotic endoscope relative to a center position of a lumen, a wall of the lumen, or another obstacle. In some embodiments, the at least third sensor is a proximity sensor. In some embodiments, the at least third sensor is a capacitive touch sensor. In some embodiments, the capacitive touch sensor comprises multiple sensing electrodes. In some embodiments, the at least third sensor is located on the segment of the main body of the robotic endoscope. In some embodiments, the steering control output signal is generated based on an analysis of the first image data stream, the second data stream, and the at least third data stream.

In some cases, the steering control output signal is generated based on an analysis of the first image data stream, the second input data stream, the at least third data stream, a historical data set, or any combination thereof. The historical data set may comprise a plurality of past steering control vectors and/or motion direction vectors, and/or loci extracted from processing of the first image stream. In some situations, the steering control signal is adjusted so that the position of the object of interest within the field-of-view varies from one image frame of the first image data stream to the next by less than 2000 pixels. In some situations, the steering control signal is adjusted so that the position of the object of interest within the field-of-view varies from one image frame of the first image data stream to the next by less than 1000 pixels.

The steering control output signal is used to control one or more actuators of the robotic endoscope. The robotic endoscope is a robotic colonoscope in some embodiments. In some situations the object of interest tracked by the provided system is a polyp, a lesion, an adenoma, or a cancerous growth.

In another aspect, a control system for performing automated route searching by providing an adaptive steering control output signal to a robotic endoscope is provided. The control system comprises: a) a first image sensor configured to provide a first image data stream, wherein the first image data stream comprises data relating to the position of a distal end of the robotic endoscope relative to a center position of a lumen, a wall of the lumen, an obstacle, or any combination thereof; and b) a processor that is configured to: i) perform automated image processing and feature extraction on one or more image frames of the first image data stream to identify the center position of the lumen; ii) determine a confidence level for data relating to the center position of the lumen relative to the distal end of the robotic endoscope; iii) generate a steering control output signal to direct the robotic endoscope to search along a specified route when the confidence level is below a first threshold; iv) repeat steps (i) to (iii) until the confidence level is above a second threshold; and v) generate a new steering control output signal based on an analysis of the first image data stream using a machine learning architecture.

In some embodiments, the confidence level is determined based on an intensity, moment of inertia, and/or convexity calculation for the lumen center position data extracted from the first image data stream. In some embodiments, the specified route is a pre-determined route selected from the group consisting of a spiral route, a rectilinear grid pattern, a circular pattern, a two-dimensional route, a three-dimensional route, or any combination thereof. In some cases, the specified route is determined by the machine learning architecture. For instance, the specified route may be automatically selected based on an analysis of the first image data stream by the machine learning architecture.

In another aspect, a method for constructing a three-dimensional map of the center position of a lumen using a robotic endoscope equipped with an adaptive steering control system is provided. The method may comprise: a) providing a first image data stream, wherein the first image data stream comprises image data relating to a position of a distal end of the robotic endoscope relative to the center of the lumen, relative to a wall of the lumen, relative to an obstacle, or any combination thereof;) generating a steering control output signal based on an analysis of the first image data stream using a machine learning architecture to identify a steering direction for movement towards the center of the lumen, wherein the steering control output signal adapts to changes in the data of the first image data stream in real time; c) storing a sequence of data pairs in a computer memory device, wherein each data pair comprises a steering direction and a translational displacement of the robotic endoscope; and d) using a processor and the stored values of steering direction and translational displacement to create a three-dimensional map of the position of the center of the lumen.

In some embodiments, the method further comprises using the three-dimensional map to provide a set of spatial coordinates that identify the location of a feature of interest that is detected in the first image data stream. In some cases, the set of spatial coordinates is used by a surgeon or other healthcare provider to guide a subsequent surgical procedure or healthcare procedure.

In another aspect, a method for reconstructing a three-dimensional image map of the interior of a lumen using a robotic endoscope equipped with an adaptive steering control system is provided. The method may comprise: a) providing a first image data stream, wherein the first image data stream comprises image data relating to a position of a distal end of the robotic endoscope relative to the center of the lumen, relative to a wall of the lumen, relative to an obstacle, or any combination thereof; b) generating a steering control output signal based on an analysis of the first image data stream using a machine learning architecture to identify a steering direction for movement towards the center of the lumen, wherein the steering control output signal adapts to changes in the data of the first image data stream in real time; c) storing the image data from the first image data stream, and values of steering direction and translational movement of the robotic endoscope, in a computer memory device; d) using the stored values of steering direction and translational movement to create a three-dimensional map of the position of the center of the lumen; and 3) overlaying the stored image data with the three-dimensional map of the position of the center of the lumen to reconstruct a three-dimensional image map of the lumen interior.

In some embodiments, the method may further comprise displaying all or a portion of the three-dimensional image map data on a viewing device. In some embodiments, the viewing device comprises a display screen or is a wearable augmented reality device that displays a three-dimensional view. In some embodiments, the three-dimensional view is a first person view, or an augmented reality view comprising images of the reconstructed lumen interior and the robotic endoscope. In some cases, the image of the robotic endoscope in the three-dimensional view is constructed based on a pre-stored computer-aided design model of the robotic endoscope.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference in its entirety. In the event of a conflict between a term herein and a term in an incorporated reference, the term herein controls.

BRIEF DESCRIPTION OF THE DRAWINGS

A better understanding of the features and advantages of the present invention will be obtained by reference to the following detailed description that sets forth illustrative embodiments, in which the principles of the invention are utilized, and the accompanying drawings of which.

DETAILED DESCRIPTION

Figure 1A:
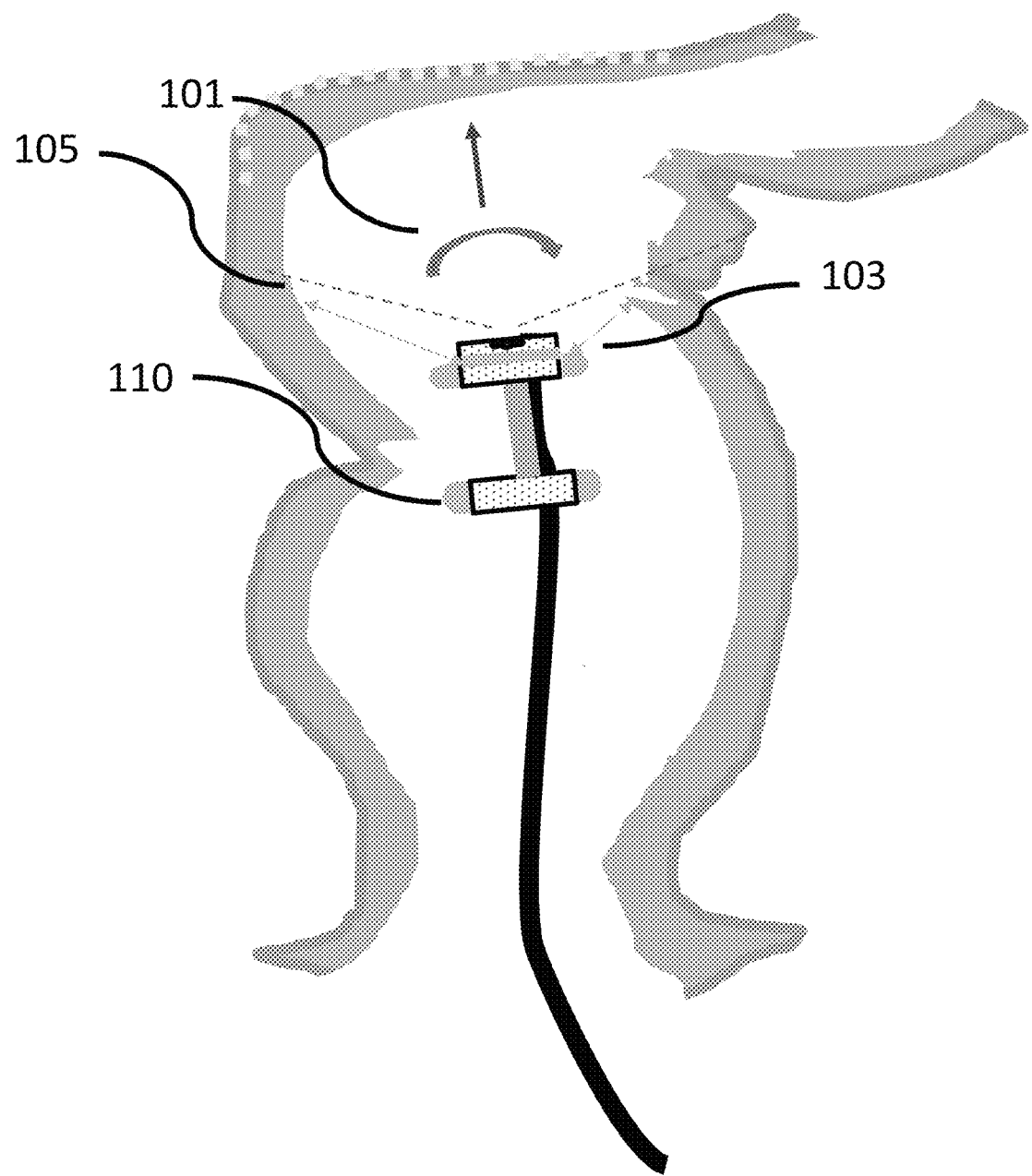
FIG. 1A schematically illustrates a colonoscope controlled by an automated steering system, in accordance with some embodiments of the invention.

While preferred embodiments of the invention are shown and described herein, it will be obvious to those skilled in the art that such embodiments are provided by way of example only. Numerous variations, changes, and substitutions will now occur to those skilled in the art without departing from the disclosed invention. It should be understood that various alternatives to the embodiments of the invention described herein may be employed in practicing the invention.

Overview:

Disclosed herein are systems and methods for semi-automated or fully-automated steering control of a robotic endoscope. Although described primarily in the context of a robotic colonoscope, it will understood by those of skill in the art that the disclosed invention may be applied for semi-automated or fully-automated steering control of any robotic colonoscopy system, or for any robotic or endoscopic system in general that requires steering control. Various aspects of the invention described herein may be applied to any of the particular applications set forth below. It shall be understood that different aspects of the invention can be appreciated individually, collectively or in combination with each other.

In one aspect of the invention, a steering control system and method are provided. The control system may provide an adaptive steering control output signal for steering a robotic endoscope in real-time. In some instances, the steering control system (or method) may utilize an artificial intelligence algorithm (e.g., a deep machine learning algorithm) to process image data as input and provide a predicted steering direction and/or steering control signal as output for guiding the movement of the robotic endoscope. In some instances, the steering control system may utilize image processing algorithms to pre-process image data prior to providing it as input to the artificial intelligence algorithm. In some instances, the steering control system may utilize a combination of two or more image processing algorithms to pre-process image data prior to providing it as input to the artificial intelligence algorithm. In some instances, the steering control system may utilize an artificial intelligence algorithm to process touch/proximity sensor data as input and provide a predicted steering direction and/or steering control signal as output for guiding the movement of the robotic endoscope. In some instances, the steering control system may utilize an artificial intelligence algorithm to integrate and process both image data and touch/proximity sensor signal data as input and provide a predicted steering direction and/or steering control signal as output for guiding the movement of the robotic endoscope. In some instances, e.g., in semi-automated mode, the steering control system may be configured to provide assistance to a surgeon who is actively guiding the advancing endoscope. In some instances, e.g., in fully-automated mode, the steering control system may be configured to guide the advancing endoscope with little or no input from a surgeon or other operator. In some instances, the control system may comprise: a) a first sensor (e.g., an image sensor) configured to provide a first input data stream, wherein the first input data stream comprises data relating to the position of the distal end of the robotic endoscope relative to the center of a lumen, compartment, or cavity; b) optionally, a second sensor (e.g., an image sensor) configured to provide a second input data stream, wherein the second input data stream comprises data relating to the position of the distal end of the robotic endoscope relative to the walls of the lumen, compartment, cavity or other obstacles; and c) one or more processors that are individually or collectively configured to determine a steering direction and/or generate a steering control output signal based on an analysis of the first and second input data streams using a machine learning architecture, wherein the steering control output signal adapts to changes in any one of the first or second data streams, or combinations thereof, in real time. In those embodiments where the first and/or second input data streams comprise image data, the image data may be pre-processed using one or more image processing algorithms prior to providing it as input to the machine learning algorithm. In some embodiments, the control system further comprises a third sensor (e.g., a touch/proximity sensor) configured to provide a third input data stream, wherein the third input data stream comprises data relating to the position of the distal end of the robotic colonoscope relative to the walls of the lumen, compartment, cavity or other obstacles that is different from the second input data stream; and wherein the one or more processors are individually or collectively configured to determine a steering direction and/or generate a steering control output signal based on an analysis of the first, second, and third input data streams using the machine learning architecture, wherein the steering control output signal adapts to changes in any one of the first, second, or third data streams, or combinations thereof, in real time. In some instances, the disclosed steering control system and method may be used to guide a robotic colonoscope. In some instances, the robotic colonscope may be a soft robotic colonoscope.

In a second aspect of the invention, a robotic endoscope system, e.g., a soft robotic endoscope, that utilizes the disclosed steering control methods and systems is described. In some instances, e.g., in semi-automated mode, the steering control system of the robotic endoscope may be configured to provide assistance to a surgeon who is actively guiding the advancing robotic endoscope. In some instances, e.g., in fully-automated mode, the steering control system of the robotic endoscope may be configured to guide the advancing endoscope with little or no input from a surgeon or other operator. In some instances, the robotic endoscope system may comprise: a) an elongated elastomeric body structure comprising one or more actuation units and a steerable distal portion; and b) a control system comprising: i) a first sensor configured to provide a first input data stream, wherein the first input data stream comprises data relating to the position of the steerable distal portion relative to the center of a colon lumen, relative to the walls of the colon lumen, relative to other obstacles, or any combination thereof; and ii) a processor that is configured to generate a steering control output signal to control the one or more actuation units based on an analysis of the first input data stream using a machine learning architecture, wherein the steering control output signal adapts to changes in the data of the first data stream in real time.

In a third aspect of the invention, methods for training and optimizing the performance of the disclosed steering control systems are provided. In some instances, the methods may comprise: a) providing a first set of input sensor data; b) providing a plurality of training datasets, wherein a training dataset comprises at least a first set of known input sensor data and a corresponding set of known output steering control signals; and c) analyzing the plurality of training datasets using the machine learning architecture to determine a set of weighting parameters, wherein the weighting parameters are subsequently used by the machine learning architecture to provide a steering control signal for the automated robotic endoscope steering mechanism that is adaptive to changes in the data of the first set of input sensor data. In some embodiments, the training data used for training and optimizing the performance of the steering control system may comprise recorded image and/or sensor data and empirical steering control instructions provided to the steering mechanism of a robotic endoscope by a surgeon or other skilled operator during previous endoscopic procedures. In some embodiments, the training data used for training and optimizing the performance of the steering control system may comprise recorded image data from previous endoscopic procedures and empirical steering control instructions provided to a virtual steering mechanism by a surgeon or other skilled operator during simulated endoscopic procedures. In some embodiments, the training data used for training and optimizing the performance of the steering control system may comprise simulated image data and paired sets of empirical steering instructions. In some embodiments, the training data may comprise any combination of the aforementioned data sets, and may further be linked to and updated via a cloud-based database.

In a fourth aspect of the invention, special features of the disclosed steering control methods and systems are described. Examples include, but are not limited to, (i) image processing algorithms and combinations thereof to improve the reliability of correctly identifying the position of a lumen center in an image, (ii) tracking an object of interest within the field of view of an image sensor, wherein the object of interest is manually selected by a surgeon or other skilled operator, or in some instances, is identified by the image processing and/or machine learning algorithms used to implement the steering control system, (iii) use of the stored data on the center position of the lumen and navigational direction determined at each step of the endoscopic procedure, along with data for the distance advanced at each step, to construct a three-dimensional map of the position of the lumen center, and (iv) the combination of a three dimensional map of the position of the lumen center with images taken at each step of the endoscopic procedure to reconstruct a three-dimensional image map of the interior of the lumen.

Definitions

Unless otherwise defined, all technical terms used herein have the same meaning as commonly understood by one of ordinary skill in the art in the field to which this disclosure belongs. As used in this specification and the appended claims, the singular forms "a", "an", and "the" include plural references unless the context clearly dictates otherwise. Any reference to "or" herein is intended to encompass "and/or" unless otherwise stated.

As used herein, the term "data stream" may refer to a continuous or discontinuous series or sequence of analog or digitally-encoded signals (e.g., voltage signals, current signals, image data comprising spatially-encoded light intensity and/or wavelength data, etc.) used to transmit or receive information.

As used herein, the term "lumen" may refer to the interior space of a tubular biological structure such as an artery or intestine, interior space of the gastrointestinal tract (e.g., the colon or large intestine, or the small intestine), or to the interior space of a hollow compartment or cavity within the body of a living organism (e.g., an animal or human).

As used herein, the term "machine learning" may refer to any of a variety of artificial intelligence algorithms (e.g., artificial neural networks (ANN) comprising multiple hidden layers) used to perform supervised learning, unsupervised learning, reinforcement learning, or any combination thereof.

As used herein, the term "real time" may refer to the rate at which sensor data is acquired, processed, and/or used in a feedback look with a machine learning or artificial neural network algorithm to update a prediction of steering direction and/or steering control signal in response to changes in one or more of the input data streams.

As used herein, the term "soft robotics" may refer to robotic systems, e.g., a soft robotic endoscope, that comprises one or more non-rigid components constructed with soft and deformable materials like silicone, plastic, fabric, rubber, or compliant mechanical parts like springs. Such robotic systems may include any of a variety of actuators or actuation mechanisms know to those of skill in the art including, but not limited to, pneumatic actuators, hydraulic actuators, springs, electrical motors or micromotors, piezoelectric transducers, etc.

Applications:

The steering control methods and systems disclosed herein may be used for any robotics system that requires a steering control function. In preferred embodiments, the disclosed methods and systems may be used to guide the movement of robotic endoscopes. Examples of endoscopes to which the disclosed methods and systems could potentially be applied include, but are not limited to, cystoscopes (for examination of the bladder), nephroscopes (for examination of the kidney), bronchoscopes (for examination of the bronchus), arthroscope (for examination of joints), colonoscopes (for examination of the colon), duodenoscopes (for examination of the duodenum), enteroscopes (for examination of the small intestine) esophagogastroduodenoscopes (for examination of the lining of the esophagus, stomach, and first part of the small intestine), and laparoscopes (for examination of the abdomen or pelvis). In some instances, the endoscopes may be used not only for visual examination and diagnosis, but also to assist with delivery of drugs or devices (e.g., stents) or in surgical procedures (e.g., laparoscopic surgical anastomosis, arthroscopy, etc.). In one preferred example, the steering control method may be used for controlling a colonoscopy system, e.g., a soft robotic colonoscopy system.

Automated Steering of a Robotic Colonoscope:

FIG. 1A schematically illustrates a colonoscope 110 controlled by an automated steering system, in accordance with embodiments of the invention. In some embodiments, the colonoscope 110 may comprise a robotic system that is made with deformable materials like plastic, or flexible mechanical components like springs. The colonoscope and the provided steering control system may be used to perform a diagnostic, therapeutic or surgical procedure within a body cavity, such as the colonic lumen, of a patient. The provided steering control system and method may enable the endoscopic system 110 to advance around flexures, e.g., looping and/or bending sections of the cavity, such as those within the colonic lumen. In some instances, the steering control system may be semi-automatic, i.e., configured to provide assistance in steering to a surgeon or other skilled operator that is guiding the colonoscope. In some instances, the steering control system may be fully-automatic, i.e., configured to determine the correct navigation direction and provide a set of steering control instructions to one or more actuators of the robotic colonoscope with little or no input from a surgeon or skilled operator.

Locomotion of the colonoscope may also be controlled automatically or semi-automatically. In some cases, insertion of the colonoscope for forward movement may be manually controlled, while the subsequent direction of movement, i.e., in the forward or backward direction, may be controlled either manually or automatically. Alternatively, both the forward or backward movement of the colonoscope and the steering direction may be controlled automatically. In general, the rate for the forward or backward motion of the colonoscope will vary over the course of performing a procedure, and may range from about 0 cm/sec to about 10 cm/sec. In some instances, the rate of forward or backward motion at a given point in the procedure may be at least 0 cm/sec, at least 1 cm/sec, at least 2 cm/sec, at least 3 cm/sec, at least 4 cm/sec, at least 5 cm/sec, at least 6 cm/sec, at least 7 cm/sec, at least 8 cm/sec, at least 9 cm/sec, or at least 10 cm/sec. In some instances, the rate of forward or backward motion at a given point in the procedure may be at most 10 cm/sec, at most 9 cm/sec, at most 8 cm/sec, at most 7 cm/sec, at most 6 cm/sec, at most 5 cm/sec, at most 4 cm/sec, at most 3 cm/sec, at most 2 cm/sec, at most 1 cm/sec, or at most 0 cm/sec. Those of skill in the art will recognize that at a given point in the procedure, the rate of forward or backward motion may have any value within this range, e.g., about 3.5 cm/sec. In some instances, the use of the automated steering control methods and systems of the present disclosure may enable average rates of forward or backward motion of the colonoscope over the course of a procedure that are substantially faster than those achieved for a conventional manual colonoscope, thereby shortening the overall duration of the procedure.

The use of the disclosed methods and systems allows the colonoscope to automatically adjust its direction of movement 101 with respect to its environment 105. In some examples, the movement direction may be controlled by adjusting a direction or orientation of a distal end 103 of the colonoscope, or by adjusting a position of the distal end relative to the surrounding environment. The distal end 103 may be, for example, a head portion that guides the movement of the main body of the colonoscope, thereby allowing the colonoscope to navigate through the environment. Within the colon lumen, for instance, the environment 105 may comprise multiple flexural, looping or bending sections through which the steering control system allows the colonoscope to be maneuvered. For instance, the colonoscope may be able to adjust or control the position of the distal end 103 relative to the center of the colon lumen or the walls of the colon lumen. In another instance, the colonoscope may be able to adjust or control the direction or orientation of the distal end 103 relative to the main body of the colonoscope, the center of the colon lumen, or the walls of the colon lumen. In some cases, the steering control system may control the movement of the distal end 103 with respect to at least two degrees of freedom (DOF), such as a pitch and yaw movement. In some cases, movement of the distal end 103 may be controlled with respect to any combination of roll, pitch, or yaw movement. In example embodiments, each degree of freedom may comprise an angular change of at least, for example, 1 degree, 5 degrees, 10 degrees, 20 degrees, 30 degrees, 40 degrees, 50 degrees, 60 degrees, 70 degrees, 80 degrees, 90 degrees, 110 degrees, 110 degrees, 120 degrees, 130 degrees, 140 degrees, 150 degrees, 160 degrees, 170 degrees, or 180 degrees. In some embodiments, the range of motion for each independent degree of freedom may be the same or may be different, and may range, for example, from 1 degree to 180 degrees, or over any fractional range thereof. In some cases, the movement of the distal end 103 controlled by the steering control system may include translational movement such as forward or backward movement.

As noted above, the disclosed methods and systems for automated steering control allow the direction of movement of the colonoscope (or more generally, an endoscope) to be controlled based on a position of a distal end of the colonoscope (or endoscope) relative to its environment. The environment may include any type of obstacle or contour that requires a determination of a new steering direction in order to avoid the obstacle or navigate around the contour. Typically, the environment to be examined using the colonoscope (or endoscope) may comprise a substantially hollow space, and the steering direction or steering control signal provided to the colonoscope (or endoscope) by the automated steering system may be a specified direction relative to a wall of the hollow space, or relative to an identified or predicted center point of the hollow space immediately ahead of the advancing distal end of the colonoscope (or endoscope). For instance, the environment of the colon lumen has many flexural looping or bending sections through which a colonoscope must be steered in order to navigate through the colon.

In some cases, the steering direction for the distal end of a colonoscope may be determined relative to a wall of the colonic lumen and/or relative to the center of the colonic lumen. In some cases, the location of the lumen center proximal to the distal end 103 of the colonoscope may be identified from sensor data (e.g., image sensor data) in order to determine the navigation or steering direction. In some cases, a position of the distal end 103 relative to the surrounding colon wall or obstacles proximal to the distal end may be identified from sensor data (e.g., image sensor data and/or touch/proximity sensor data) in order to determine the navigation or steering direction. In some cases, once the position of the distal end relative to the lumen center and/or the surrounding wall are known, the distal end may be steered and guided towards the lumen center and away from contacting the colon wall or obstacles. The steering direction may or may not be aligned with the center axis of the lumen. The steering direction or navigation direction may be determined by the provided automated steering control systems or methods. In some instances, the input sensor data used to determine steering direction or navigation direction may be used for feedback control of the colonoscopy system such that the steering direction or navigation direction adapts in real time to changes in the input sensor data. The steering control system may receive input sensor data collected by the plurality of sensors and output a target direction or control signal to the actuation unit of the colonoscope. In some instances, the steering direction or navigation direction determined at each point in time may be used in conjunction with data for the forward translational movement of the colonoscope to track the position of the distal end over time, thereby generating a record of the path of motion of the distal end. Thus a motion vector between current location and the position predicted by the target navigation direction may be generated by incorporating the dynamics of the robotic system in view of the navigation direction.

The steering direction or movement of the steerable distal end of an endoscope (e.g., a colonoscope) may be determined using the provided steering control methods and systems that incorporate the use of a single input sensor data stream or a plurality of input sensor data streams, and processing using artificial intelligence algorithms. In some instances, for example when at least one input sensor data stream comprises image data, the image data may be pre-processed using any of a variety of image processing algorithms, or a combination thereof, prior to providing the processed image data or results to the artificial intelligence algorithm. The types of movement that may be controlled through the use of the disclosed methods and systems include, but are not limited to, steering direction of the distal end, backward or forward movement of the endoscope, rate of translational (forward or backward) movement, acceleration, and the like.

Once the steering direction or direction of movement for the distal end is determined, the distal end may be actuated by one or more actuators to bend, turn, pivot, twist, or move in accordance with the steering direction. The one or more actuators may be affected by control signals generated by the provided method. In some embodiments, the one or more actuators may be connected to one or more sections of the steerable distal end of the endoscope by means of wires (or "tendons") in order to affect movement of the steerable distal end. Various sensors may be used to provide information regarding the location of the lumen center and the position of the distal end relative to the lumen wall. A steering direction may be determined and control instructions to the one or more actuators of the distal end may be generated to effect movement of the distal end or the colonoscope.

Figure 2:
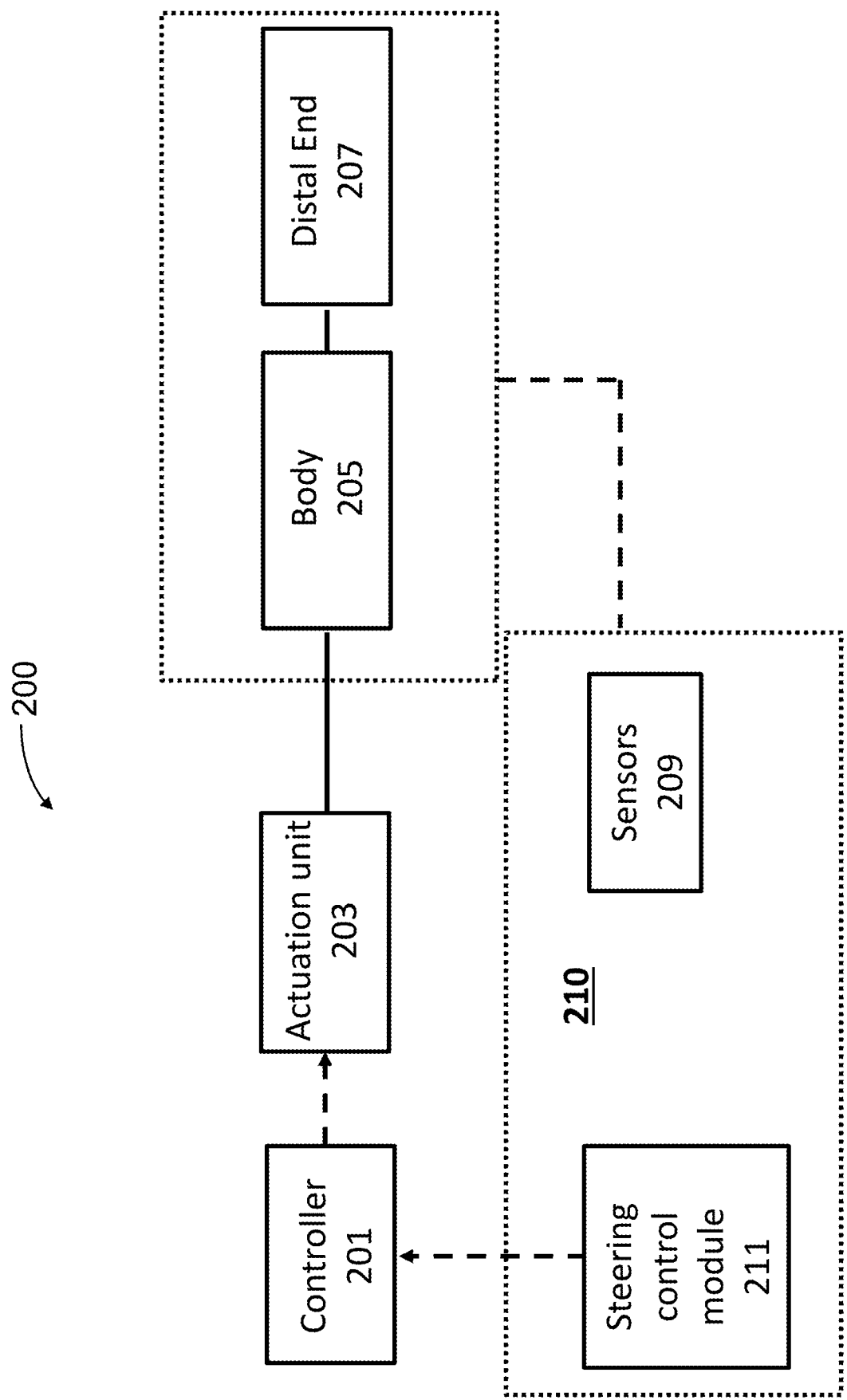
FIG. 2 shows a block diagram of an exemplary robotic endoscope system controlled by a steering control system, in accordance with some embodiments of the present disclosure.

FIG. 2 shows a block diagram of an exemplary robotic colonoscope system controlled by a steering control system 210, in accordance with embodiments. In some embodiments, the steering control system may comprise a steering control module 211 which is configured to process data provided by one or more sensors 209 to determine a steering direction and generate a steering control signal. In some instances, the steering control signal may be transmitted to a controller 201 of the colonoscope system for controlling an actuation unit 203. In some instances, the output of the steering control system 210 may be control signals that are sent to the actuation unit directly. In other instances, the steering control system may comprise the controller such that the output of the system is the control signal sent to the actuation unit. The determination of a steering direction and the generation of the steering control signal that is output by the steering control system may be performed using a machine learning architecture-based control algorithm such as neural network running on a processor (i.e., a steering control processor). Details about the control algorithm are discussed later herein. The actuation unit 203 may be used to effect the steering direction of the colonoscope. For example, the actuation unit may affect the steering direction of a distal end 207 of the colonoscope.

As mentioned elsewhere herein, the colonoscope may comprise a distal end 207 which guides the movement of the main body 205 of the colonoscope. The main body may be flexible and compliant. In some instances, the main body may be an elongated tubular body. In other instances, the main body may have any shape or dimension that can be inserted into a cavity of a patient and guided by the distal end.

The distal end 207 may be steered towards a target direction determined by the steering control system. The distal end may or may not be coupled to additional tools such as biopsy tools or drug delivery devices. The distal end may be manipulated by any suitable actuation mechanism to effectuate the steering movement. For instance, the distal end may comprise a steerable portion such as a bending section that may be actuated in one or more directions with respect to the main body. Any suitable mechanism may be used to effectuate the steering direction of the distal end. For example, the distal end may comprise one or more internal cavities fabricated from a deformable material such that, by controlling a change of pressure, temperature, differential stiffness, or other such parameters that impact the size, shape, or volume thereof, may be expanded, bent or extended such that a direction of the distal end may be controlled. Various other mechanisms can be used for actuating movement (such as a bending, straightening, turning, pivoting, twisting, moving, etc) of the distal end in a target steering direction. For instance, wires and other continuum mechanical structures can be used for steering the distal end. In some instances, microelectrical motors or piezoelectric transducers may also be utilized for actuation.

The distal end 207 may be actuated by an actuation unit 203. The actuation unit may comprise suitable actuators or actuation mechanisms for effectuating the movement of the distal end in the target direction determined by the steering control system 210. The actuation unit may be operably coupled to the steering control system 210 or the controller 201. Various actuators or mechanisms can be used. For example, the actuation unit may utilize one or more hydraulic actuators or pneumatic actuators. The actuation unit may utilize various other types of actuators such as electric motors, micromotors, piezoelectric transducers, etc. In some embodiments, the actuators may be connected to one or more sections of the steerable distal end of the endoscope by means of wires (or "tendons") in order to affect movement of the steerable distal end. Depending on the specific actuation unit and/or dynamics of the colonoscope, a controller 201 may be selected to generate control signals to the actuators to effect the steering direction of the distal end. In some cases, the controller 201 is separate from the steering control system 210. The controller 210 may receive a target direction from the steering control system and generate control signals to control the actuation unit 203. In some cases, the controller 201 may be incorporated into the steering control system. In this case, a control signal supplied to the actuation unit may be generated by the steering control system 210. The actuation unit or actuators may or may not be located within the cavity of the patient. The actuation unit or actuators may or may not be located at the distal end of the colonoscope.

Figure 1B:
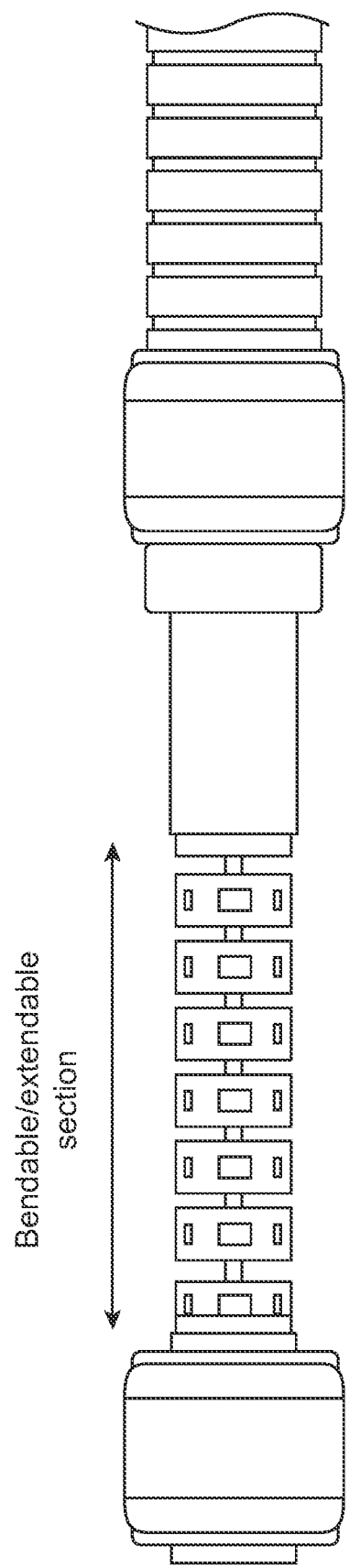
FIG. 1B illustrates a bendable/extendable section of a colonoscope (i.e., the steerable distal end) that is actuated by a series of embedded tendons running through a flexible section of the colonoscope.

In some embodiments, the steerable distal end of the colonoscope may comprise a bendable/extendable section as illustrated in FIG. 1B, wherein bending is accomplished through the actuation of a series of embedded tendons running through the bendable/extendable section (i.e., a tendon-driven actuator mechanism). The bendable/extendable (neck) section at the distal end of colonoscope is housed between the positions of two inflatable balloons, as shown in FIG. 1B. The two inflatable balloons serve as anchors to hold the position of the colonoscope as needed. In some embodiments, the flexible, tendon-driven section has a length of no more than 40 mm, has a bending angle of more than 150°, and is designed to perform omnidirectional bending of the colonoscope to allow a thorough examination behind the folds in the colon. In some embodiments, the length of the bendable/extendable section may be no more than 20 mm, no more than 30 mm, no more than 40 mm, no more than 50 mm, or no more than 60 mm. In some embodiments, the bending angle of the flexible, tendon-driven section may be more than 90°, more than 100°, more than 110°, more than 120°, more than 130°, more than 140°, more than 150°, more than 160°, or more than 170°. The bending angle and bending direction are controlled by the motion of a number of embedded tendons that run through the flexible section. In addition, this section can also be motorized to extend/elongate the distal end. In some embodiments, the actuator for the extension/elongation is not embedded as a part of the colonoscopic device but rather it is placed on the control system. This practical design therefore does not require the disposal of the actuator when the colonoscopic device is disposed of, which saves on the manufacturing cost of the device.

Referring again to FIG. 2, the steering control system 210 may be configured to control the steering movement of the colonoscope. The steering control system may control movement of the colonoscope including steering movement and advancing movement. The steering control system may enable automated or semi-automated control of the colonoscope. In some cases, the steering direction of the colonoscope is automatically controlled by the steering control system whereas the insertion speed or depth may be controlled manually. The insertion movement may be controlled by an additional controller which receives input from an operator or user via any suitable user interface such as a button, joystick, thumbstick, touchpad, motion control, voice control, accelerometer, haptic feedback, or the like. Alternatively, the insertion movement may be controlled by the same steering control system used to direct the movement of the distal end of the colonoscope. The steering control system may be configured to generate a target direction. In some cases, the steering control system may be configured to provide an adaptive steering control output signal for steering the robotic colonoscope, e.g., a steering control output signal that adapts to changes in the input sensor data for one or more sensors in real time. The steering control system may be operably coupled to the colonoscope.

In some embodiments, the steering control system 210 may comprise at least a steering control module 211 and a sensor 209. In some embodiments, the steering control system 210 may comprise at least a steering control module 211 and a plurality of sensors 209. The steering control module 211 may be operably coupled to the colonoscope. In some instances, the steering control module may be on-board the colonoscope. In some instances, the steering control module is external to the cavity of the patient. Alternatively, the steering control module may be located internal to the cavity of the patient and connected to the colonoscope. The steering control module may comprise one or more processors configured to determine a target direction and/or generate output control signals to the actuation unit. In some embodiments, the one or more processors may be a programmable processor (e.g., a central processing unit (CPU), a graphic processing unit (GPU), a general-purpose processing unit or a microcontroller), in the form of fine-grained spatial architectures such as a field programmable gate array (FPGA), an application-specific integrated circuit (ASIC), and/or one or more Advanced RISC Machine (ARM) processors.

In some embodiments, the one or more processors may be operatively coupled to a non-transitory computer readable medium. The non-transitory computer readable medium can store logic, code, and/or program instructions executable by the one or more processor units for performing one or more processing steps. In some cases, the one or more memory units of the steering control system 210 may store a plurality of computational parameters, e.g., weighting factors, biases, threshold values, and various other data that define the machine learning architecture and one or more computation instructions. Details about the machine learning architecture or techniques will be discussed later herein. The non-transitory computer readable medium can include one or more memory units (e.g., removable media, main memory, external storage such as an SD card or random access memory (RAM)). The memory units can include any suitable RAM, including static random-access memory (SRAM), dynamic random-access memory (DRAM), synchronous dynamic random-access memory (SDRAM), double data rate (DDR), double data rate synchronous dynamic random-access memory (DDR SDRAM), DDR, DDR2, DDR3, T-RAM, Z-RAM, and so forth.

In some embodiments, the plurality of sensors 209 may be located at or in close proximity to the distal end 207 of the colonoscope. In some embodiments, the plurality of sensors may comprise at least one sensor, at least two sensors, at least three sensors, at least four sensors, at least five sensors, or more than five sensors. The plurality of sensors may provide sensor data comprising information related to a location of the lumen center, or the position of the distal end relative to the surrounding colonic wall. In some embodiments, the plurality of sensors may comprise at least an optical imaging sensor and a touch/proximity sensor. In some embodiments, both an optical imaging sensor and a touch/proximity sensor are located at the distal end.

In some cases, the plurality of sensors may be removably attached to the distal end. The plurality of sensors can be attached to varied locations of the distal end such as around the perimeter of the distal end. The plurality of sensors may be arranged such that, for example, an optical imaging sensor and a touch or proximity sensor may provide information about obstacles or portions of the colonic wall that are in proximity to the distal end. In some cases, the sensing range may be determined based on the location of the sensors. For instance, when a line of sight (LOS) of an image sensor, e.g., a miniature camera, is substantially aligned with the forward moving direction, the imaging sensor may provide a sensing range (e.g., a field of view) that enables detection of objects or the structure of the environment in front of the distal end. In some cases, the location of the lumen center may be identified within the field of view. In some cases, obstacles within the field of view may be identified based on light reflection intensities derived from the image data. In another instance, for example, when touch or proximity sensors are positioned around the perimeter of the distal end, the sensing range may refer to the range within which obstacles or environmental structures positioned around the perimeter of the distal end can be sensed.

The plurality of sensors may, in some instances, include sensors such as photosensors, optical image sensors, additional touch/proximity sensors, motion sensors, or location sensors located at the distal end of the colonoscope or in the main body of the colonoscope such that these sensors may provide additional information about a relative position of the body portion relative to a colonic wall or lumen center or various motion properties of the colonoscope. In some embodiments, the number of additional sensors of sensors may comprise at least one sensor, at least two sensors, at least three sensors, at least four sensors, at least five sensors, or more than five sensors.

The additional information or sensor data may or may not be supplied to the steering control module for determining the control signal or target direction. In some embodiments, sensors located in the main body of the colonoscope (e.g., in one or more segments of the main body of the colonoscope) may provide sensor data such as proximity data as part of the input data supplied to the control system for generating a steering control signal. For instance, in addition to the input data collected from sensors located at the distal end, proximity information indicating the position of one or more segments of the main body relative to the colonic wall or lumen center may also be used for generating the control signal. This may be beneficial for providing optimized control of the configuration and steering direction of the colonoscope. Alternatively or additionally, sensor data collected by sensors located in the main body of the colonoscope may be utilized to provide real-time data on the configuration of the main body for facilitating the reconstruction of a two-dimensional or three-dimensional map of the interior of the lumen. Details about the reconstruction of two-dimensional or three-dimensional maps will be described later herein.

The plurality of sensors may be operably coupled to the steering control module 211. Sensor data collected by the plurality of sensors may be transmitted to the steering control module for determining a target steering direction. In some cases, the plurality of sensors may be configured to transmit the sensor data in a wired or wireless manner. Any suitable means can be utilized for data transmission. For example, wired communication buses (e.g., inter-integrated circuits (I2C)) may be provided for data transmission. It is noted that any type and any number of wired communication buses (such as I2C or serial peripheral interfaces (SPI)) or wireless communication means (e.g., Bluetooth, Wi-Fi) can be used to accomplish data transmission. Selection of various means for transmitting data may be determined based on need of speed for transmission and bandwidth requirement.

Touch or Proximity Sensors:

In some embodiments, the plurality of sensors 209 may include a touch or proximity sensor. Touch or proximity sensors may be used to provide topographical information of the colonic lumen in the vicinity of the colonoscope, or to detect obstacles in close proximity to the advancing tip of the colonoscope. For example, the touch or proximity sensors may be configured to monitor or measure a position of the distal end relative to the surrounding colonic wall or relative to the lumen center. Various techniques may be employed to provide touch or proximity sensing capability, such as capacitive sensing, resistive sensing, or a combination of both. Other techniques such as thermal infrared, radar, or optical sensing, and the like, can also be used for proximity sensing.

Figure 3:
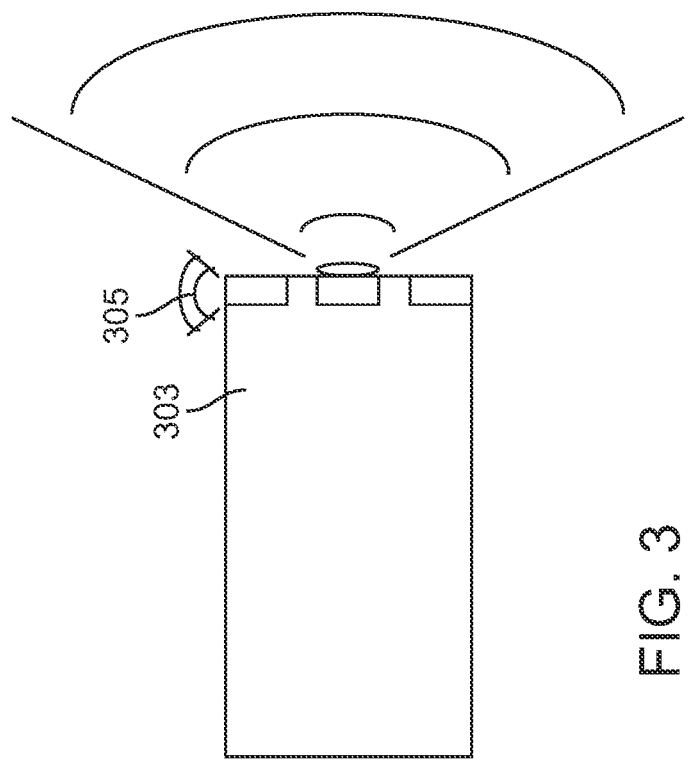
FIG. 3 shows an example of capacitive sensors used to provide touch or proximity sensing at the distal end of an endoscope, for example, at the distal end of a robotic colonoscope.
Figure 3:
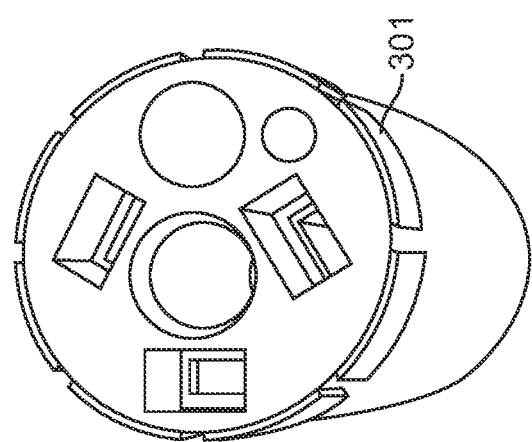

FIGS. 3 and 4 show exemplary capacitive sensors used to provide touch or proximity sensing. Capacitive sensing technology may utilize a capacitive coupling mechanism that can detect and measure changes in capacitance caused by relative motion of a conductive or dielectric material in proximity to a sensing electrode.

As shown in FIG. 3, the capacitive sensors may include one or more electrode sensing plates 301. The electrode sensing plate may comprise circuits such as flexible printed circuits. The electrode sensing plate may be configured to measure a capacitance such that a distance between the sensing plate and an object (e.g., the colonic wall) may be measured based on the capacitance. In some instances, the capacitive sensor may rely on measurements of mutual capacitance, e.g., where proximity to an object such as the colonic wall alters the mutual capacitive coupling between row and column electrodes of the electrode sensing plate, which are scanned sequentially. In some instances, the capacitive sensor may rely on measurements of self- (or absolute) capacitance, e.g., where close proximity to an object such as the colonic wall increases the parasitic capacitance to ground. The electrode sensing plate may have various shapes such as rectangular, square, circular, and the like. The capacitive sensor may comprise one or more of the electrode sensing plates. In some cases, the one or more electrode sensing plates may be mounted symmetrically around to the perimeter of the distal end 303 of the colonoscope. Alternatively, the electrode sensing plates may not be placed symmetrically. The electrode sensing plates may be mounted to a rigid portion of the distal end such that the locations where the electrode sensing plates are attached may be fixed relative to one another. The capacitive sensor may comprise any number of electrode plates. For instance, the capacitive sensor may comprise at least, one, two, three, four, five, six, seven, or eight electrode plates. The capacitive sensor may further comprise a microcontroller. In some instances, the microcontroller may be enclosed within a housing or, for instance, embedded in the same package that houses an image sensor (e.g., a miniature camera).

In some cases, a distance between the sensor electrode plates and the colonic wall is measured. For example, an object or region of the colonic wall that is positioned within a certain proximity range 305 of the capacitive sensor may be detected and the distance may be measured. The sensing range may be at least, for example, 1 mm, 2 mm, 3 mm, 5 mm, 7 mm, 10 mm, 15 mm, 20 mm, 30 mm, 40 mm, or 50 mm. In some cases, the sensing range may be fixed. In some cases, the sensing range may be adjustable. In some cases, the sensing range may be range from about 1 mm to about 50 mm. In some cases, it may be less than about 1 mm. In some cases, it may be greater than about 50 mm. In some cases, a position of the distal end relative to the colonic wall or lumen center is determined. For example, when the plurality of electrode plates are placed symmetrically, an offset of the read-outs from the plurality of electrode plates may be indicative of an off-center position of the distal end relative to the lumen center. The capacitive sensor may be used to measure a position of the distal end relative to the lumen wall or the lumen center with or without detecting a contact. In some cases, the relative position may be determined without detection of a contact point. In some cases, the capacitive sensor may detect a touch or contact point with an object such as the colonic wall. In some instances, when the object or a portion of the colonic wall is detected to be within a certain proximity of the distal end of the colonoscope, the steering control system may steer the colonoscope in a direction away from the object or portion of the colonic wall. The capacitive sensor data may be transmitted to the steering control module and used to determine a target direction such that the distal end may be repositioned to avoid contact with the object or to move away from the object.

Figure 4A:
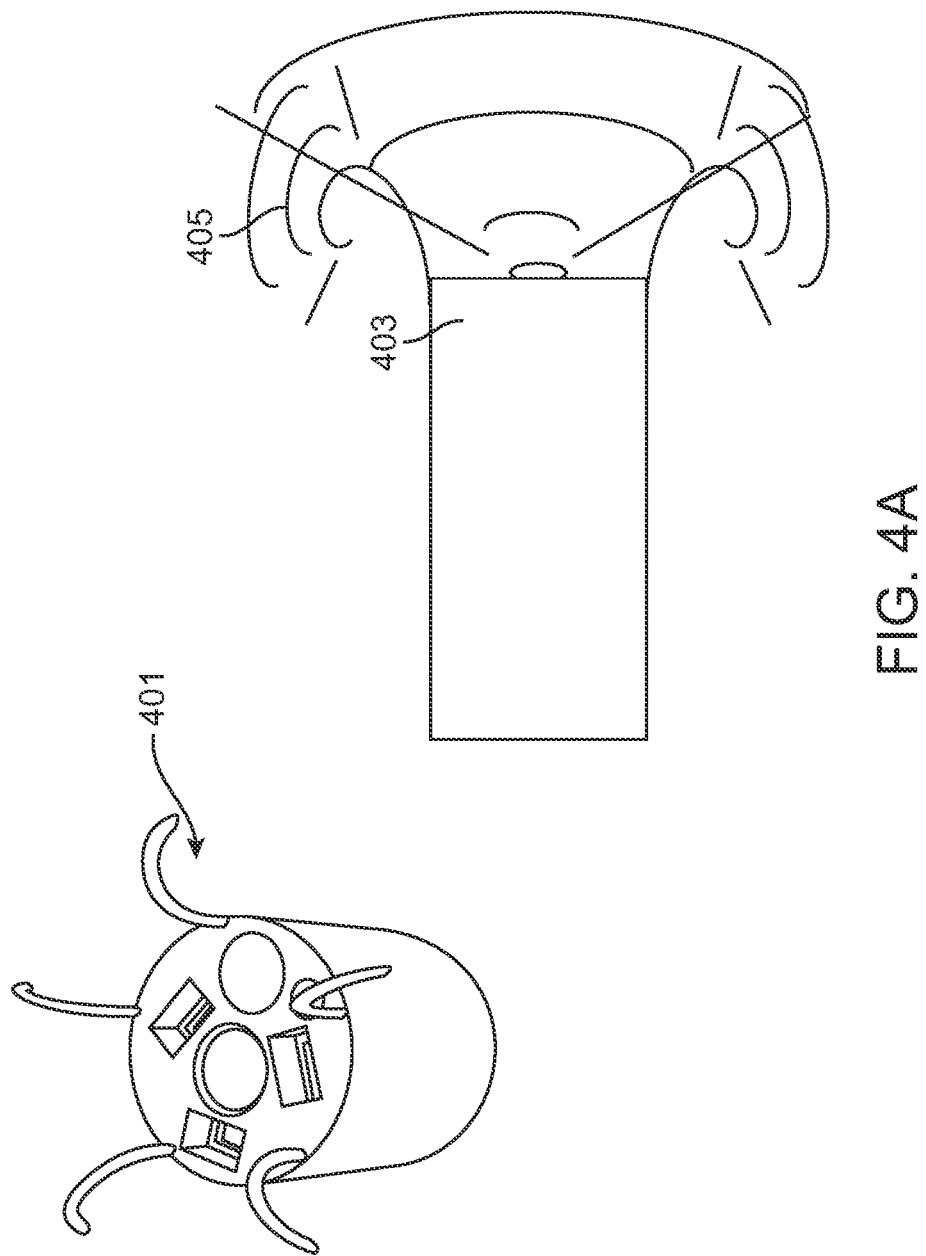
FIG. 4A show another example of capacitive sensors used to provide touch or proximity sensing at the distal end of an endoscope, for example, at the distal end of a robotic colonoscope.

FIG. 4A shows another example of capacitive sensors, in accordance with certain embodiments. As shown in FIG. 4A, the capacitive sensors may include one or more sensing tentacles 401. The sensing tentacles may be metallic wires that are radial mounted on the distal end. The sensing tentacles may comprise one or more circuits located at the base of the tentacles which are attached to the distal end. The sensing tentacles may be configured to measure a capacitance such that a distance between the sensing tentacles and an object (e.g., a portion of the colonic wall) may be measured based on the capacitance. For instance, the measured capacitance may increase as the capacitive sensor approaches the colonic wall or other objects. The capacitive sensor may comprise one or more of the sensing tentacles. In some cases, the one or more sensing tentacles may be mounted symmetrically around the perimeter of the distal end 403 of the colonoscope. Alternatively, the sensing tentacles may not be placed symmetrically. In some cases, the sensing tentacles may be mounted to a rigid portion of the distal end such that the locations where the sensing tentacles are attached are fixed relative to one another. The capacitive sensor may comprise any number of sensing tentacles. For instance, the capacitive sensor may comprise at least, one, two, three, four, five, six, seven, or eight sensing tentacles. The capacitive sensor may further comprise a microcontroller. In some instances, the microcontroller may be enclosed within a housing or, for instance, embedded in the same package that houses an image sensor (e.g., a miniature camera).

Figure 4B:
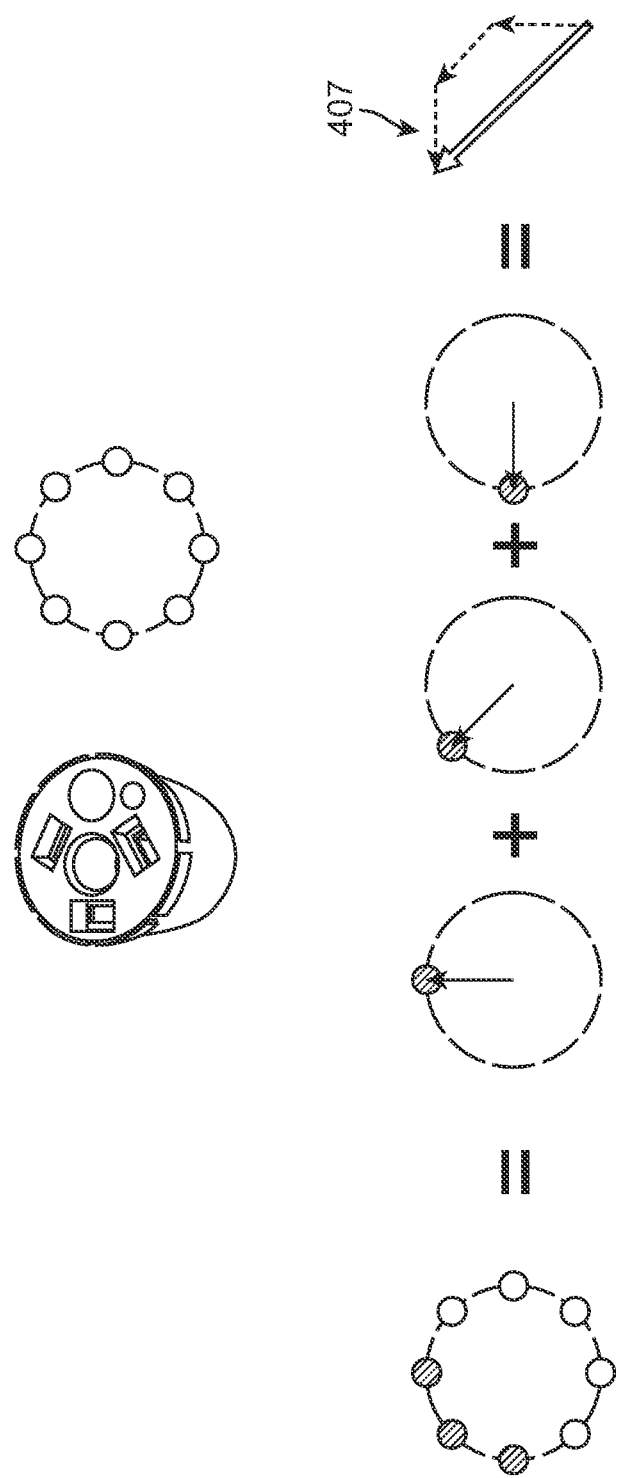
FIG. 4B illustrates an exemplary approach to the determination of direction vectors using proximity sensing.

In some cases, a position of the distal end of the robotic colonoscope relative to the colonic wall or lumen center is determined. For example, when the plurality of electrode plates are placed symmetrically, an offset of the read-outs from the plurality of electrode plates may be indicative of an off-center position of the distal end relative to the lumen center. In some cases, proximity or distance from a portion of the distal end to a detected object may be determined by the proximity sensors. FIG. 4B shows an exemplary approach to proximity detection and determination of a direction vector using a plurality of electrode sensing plates. As shown in the example, each electrode sensing plate may provide a value along a direction relative to the center of the colonoscope, i.e. a vector indicating the proximity of the sensing electrode to a colon wall or other obstacle. A sum of the plurality of vectors 407 may be calculated to determine a direction vector that indicates the position of the distal end of the colonoscope relative to the local environment or nearby obstacles.

In some cases, a distance between the sensing tentacles and the colonic wall is measured. For example, an object or region of the colonic wall that is positioned within a certain proximity range 405 of the capacitive sensor may be detected and the distance may be measured. The sensing range may be dependent on the dimension or shape of the tentacles. In some cases, the sensing range may depend on the radial distance from the perimeter of the distal end that the tentacles can reach. The sensing range may be at least, for example, 1 mm, 2 mm, 3 mm, 5 mm, 7 mm, 10 mm, 15 mm, 20 mm, 30 mm, 40 mm, 50 mm, 60 mm, 70 mm, 80 mm, or 90 mm. In some cases, a position of the distal end relative to the colonic wall or lumen center is determined. For example, when the plurality of sensing tentacles are placed symmetrically, an offset of the read-outs from the plurality of sensing tentacles may be indicative of an off-center position of the distal end relative to the lumen center. The capacitive sensor may be used to measure a position of the distal end relative to the lumen wall or the lumen center with or without detecting a contact. In some cases, the relative position may be determined without detection of a contact point. In some cases, the capacitive sensor may detect a touch or contact point with an object such as the colonic wall. In some instances, when the object or a portion of the colonic wall is detected to be within a certain proximity of the distal end of the colonoscope, the steering control system may steer the colonoscope in a direction away from the object or portion of the colonic wall. The capacitive sensor data may be transmitted to the steering control module and used to determine a target steering direction such that the distal end may be repositioned to avoid contact with the object or to move away from the object.

Other technologies may also be used as touch or proximity sensors. For example, resistive touch sensors may be utilized to detect a contact point with an object or the colonic wall. In some cases, when a touch or contact point is detected, the steering control system may steer the colonoscope away from the object.

Image Sensors:

The steering control system may further comprise one or more optical imaging sensors. One or more optical imaging sensors may be used to determine a location of the lumen center or to provide information indicative of the orientation of the distal end of the colonoscope relative the colonic lumen. The one or more optical imaging sensors may be configured to collect image data. In some cases, the one or more imaging sensors may be packaged within an imaging device such as a camera. Examples of imaging devices may include a camera, a video camera, or any device having the ability to capture optical signals. The imaging device may be configured to acquire and/or transmit one or more images of objects or environment within the imaging device's field of view. The imaging device may have a field of view of at least 80 degrees, 90 degrees, 100 degrees, 110 degrees, 120 degrees, 130 degrees, 140 degrees, 150 degrees, 160 degrees, or 170 degrees. In some instances, the field of view may be fixed. In some instances, the field of view may be adjustable. In some instances, the imaging device may have a field of view in the range of 80 degrees to 170 degrees. In some instances, the field of view may be less than 80 degrees. In some instances, the field of view may be greater than 170 degrees. The imaging device may be mounted on the distal end of the colonoscope. In some embodiments, the colonoscope may comprise one or more optical fibers (or light pipes, light guides, waveguides, etc.) that are optically coupled to one or more imaging devices that are located external to the colon lumen, wherein the optical fibers collect light that is reflected, scattered, or emitted from a field-of-view proximal to the distal end of the colonoscope and transmit it to the one or more imaging devices. The imaging device may be a 2D camera or a 3D camera. In some cases, the camera may be a 3D camera that includes two imaging sensors configured to provide stereoscopic images such that depth information about objects within the field-of-view can be derived from the captured image data.

The imaging device or camera may have a housing that encloses the one or more imaging sensors and other components of the imaging device. In some cases, microprocessor controllers of touch or proximity sensors may also be enclosed in the camera housing. The imaging sensors may be configured to generate image data in response to various wavelengths of light. For example, the imaging sensors may be configured to collect images in the ultraviolet, visible, near-infrared, or infrared regions of the electromagnetic spectrum. A variety of imaging sensors may be employed for capturing image data such as complementary metal oxide semiconductor (COMS) or charge-coupled device (CCD) sensors. In some cases, the output of the imaging sensor may be image data (digital signals) that may be processed by a camera circuit or processors of the camera. In some cases, the imaging sensor may comprise an array of optical sensors.

The imaging device may have any suitable size and/or dimensions. The imaging device may be of a size and/or dimensions suitable for being inserted into a cavity of a human or for attachment to the distal end of the colonoscope. In some instances, the imaging device may have a maximum dimension (e.g., length, width, height, diameter, diagonal) of less than or equal to about: 0.5 cm, 1 cm, 2 cm, 3 cm, 4 cm, or 5 cm. In some instances, the imaging device may have a length of less than 5 cm. In some instances, the imaging device may have an outer diameter (OD) of less than 1 cm. The imaging device may have a footprint (which may refer to the lateral cross-sectional area encompassed by the imaging device) less than or equal to about: 2 $cm^2$, 1 $cm^2$, or 0.01 $cm^2$. In some instances, the imaging device may weigh no more than 2 kg, 1 kg, 0.5 kg, 0.1 kg, 0.05 kg, 0.01 kg, 5 g, or 1 g.

The imaging sensor may capture an image frame or a sequence of image frames at a specific image resolution. The image frame resolution may be defined by the number of pixels in a frame. The image resolution may be greater than or equal to about 352×420 pixels, 480×320 pixels, 720×480 pixels, 1280×720 pixels, 1440×1080 pixels, 1920×1080 pixels, 2048×1080 pixels, 3840×2160 pixels, 4096×2160 pixels, 7680×4320 pixels, or 15360×8640 pixels. The image resolution may be any resolution within the range of about 352×420 pixels to about 15360×8640 pixels. The imaging device may have a pixel size of less than 1 micron, 2 micron, 3 micron, 5 micron, 10 micron, or 20 micron, and the like. The camera may be, for example, a 4K camera or a camera with a higher resolution. In some embodiments, the pixels of camera may be square. In other embodiments, the imaging device or camera may have non-square pixels or may include additional optical components to correct for optical distortions. The imaging device may capture color images (RGB images), greyscale image, and the like.

The imaging sensor may capture a sequence of image frames at a specific capture rate. In some embodiments, the sequence of images may be captured at standard video frame rates such as about 24p, 25p, 30p, 48p, 50p, 60p, 72p, 90p, 100p, 120p, 300p, 50i, or 60i. In some embodiments, the sequence of images may be captured at a rate less than or equal to about one image every 0.0001 seconds, 0.0002 seconds, 0.0005 seconds, 0.001 seconds, 0.002 seconds, 0.005 seconds, 0.01 seconds, 0.02 seconds, 0.05 seconds, 0.1 seconds, 0.2 seconds, 0.5 seconds, 1 second, 2 seconds, 5 seconds, or 10 seconds. In some embodiments, the capture rate may change depending on user input and/or external conditions (e.g., illumination brightness).

In some cases, the imaging device may include a zoom lens for which the focal length or angle of view can be varied. The imaging device may provide optical zoom by adjusting the focal length of the zoom lens.

The imaging device may be in communication with the steering control module. Image data collected by the imaging device may be transmitted to the steering control module. The image data may be transmitted via a wired or wireless connection. In some cases, the imaging device may be in communication with other devices. For instance, the imaging device may transmit image data to a display such that one or more images may be displayed to an operator or endoscopist operating the colonoscope. In other instances, the imaging device may receive control signals from an external device for controlling the operation of the camera (e.g., taking still or video images, zooming in or out, turning on or off, switching imaging modes, changing image resolution, changing focus, changing depth of field, changing exposure time, changing viewing angle or field of view, etc.).

In some embodiments, one or more light sources may be provided to illuminate a scene for better viewing. The one or more light sources may be mounted on the distal end of the colonoscope. In some cases, the one or more light sources may be placed in a location such that uniform illumination may be provided to illuminate the scene within the field of the view of the camera. For instance, a plurality of LED light sources may be radial mounted on the distal end. Uniform illumination may be beneficial for analyzing distance to an object, or for detection of obstacles based on light reflection. Various types of light sources may be used such as light emitting diodes (LEDs), halogen light sources, xenon light sources, and the like. In some embodiments, the colonoscope may comprise one or more optical fibers that are optically coupled to one or more light sources located external to the colon lumen, and which may be used to illuminate the field-of-view.

Image Processing to Locate a Lumen Center Position or Detect Obstacles:

In some instances, the image data may be processed using one or more image processing algorithms to provide information about the location of the center of the lumen relative to the distal end of the colonoscope (or, more generally, relative to the distal end of an endoscope). In some instances, the result(s) thus obtained from the image processing may be used as input for a machine learning algorithm to determine a navigational direction and generate a set of one or more steering control instructions. In some instances, the image data may be used to estimate a location of a lumen center position. In some instances, the image data may provide information about lumen wall contour that is useful for determining an orientation or direction of the colon relative to the distal end of the colonoscope. In other instances, the image data may provide depth information (e.g., when using a stereo camera) or distance information about one or more features perceived in the scene. In some instance, the image data may be processed, with or without additional touch or proximity sensor data, to determine a target direction for steering the colonoscope. Details about the method for processing the image data and touch or proximity data will be discussed later herein.

Figure 5A:
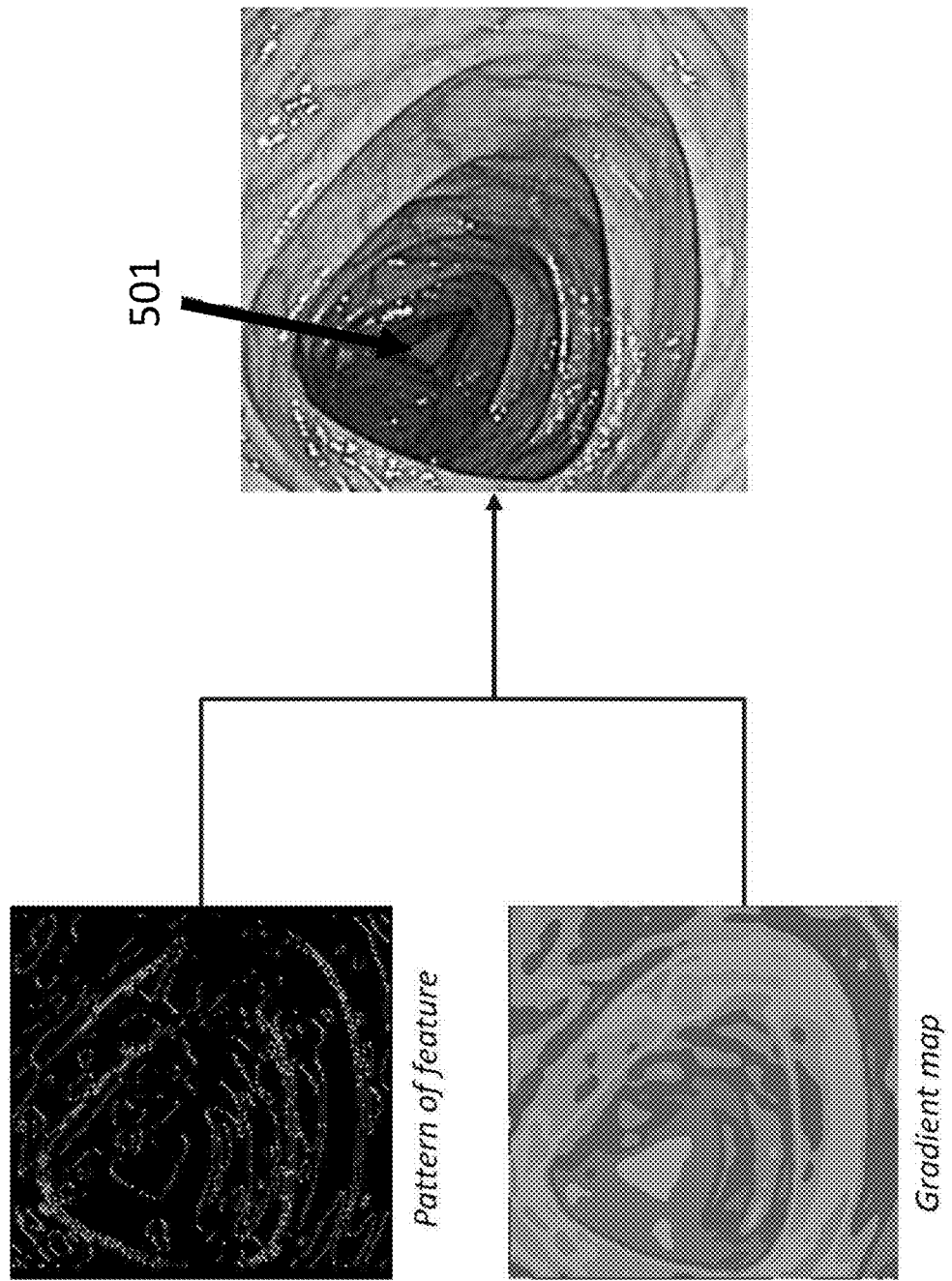
FIG. 5A shows exemplary images that comprise information about the location of the center of a colon lumen and/or the direction in which the lumen is bending ahead of an advancing colonoscope.

As noted above, in some embodiments, the image data may comprise at least a two-dimensional image of the scene captured by the imaging device. In some embodiments, the image data may be analyzed to provide information about a location of the lumen center and/or distance from the colon wall. FIG. 5A shows exemplary images that comprise information about a location of the lumen center and/or a direction of the lumen relative to the distal end of a colonoscope. In some cases, the lumen center can be directly visualized in the image. In some cases, texture of the lumen wall may also be visible and may be indicative of the orientation or direction of the lumen immediately ahead of the distal end of the colonoscope. In some cases, the location of the lumen center may be determined from image data using suitable image processing techniques, e.g., feature extraction, edge detection, pattern recognition, pattern matching, and the like. For example, given the particular topography or texture of the lumen wall such as the mucosal folds, features perceived in the image that indicate the presence of the folds may be recognized through image processing, and a centroid or locus of a dark region may be used to determine the location of the lumen center 501. Examples of image processing algorithms that may be suitable for use in the disclosed methods include, but are not limited to, Laplacian of Gaussian (LoG) methods, Canny edge detection methods, Canny-Deriche edge detection methods, Sobel operator methods, first-order gradient detection methods, second order differential edge detection methods, phase coherence edge detection methods, intensity thresholding methods, intensity clustering methods, intensity histogram-based methods, generalized Hough transforms, circular Hough transforms, Fourier transforms, fast Fourier transforms, wavelet analysis, and auto-correlation analysis.

Figure 5B:
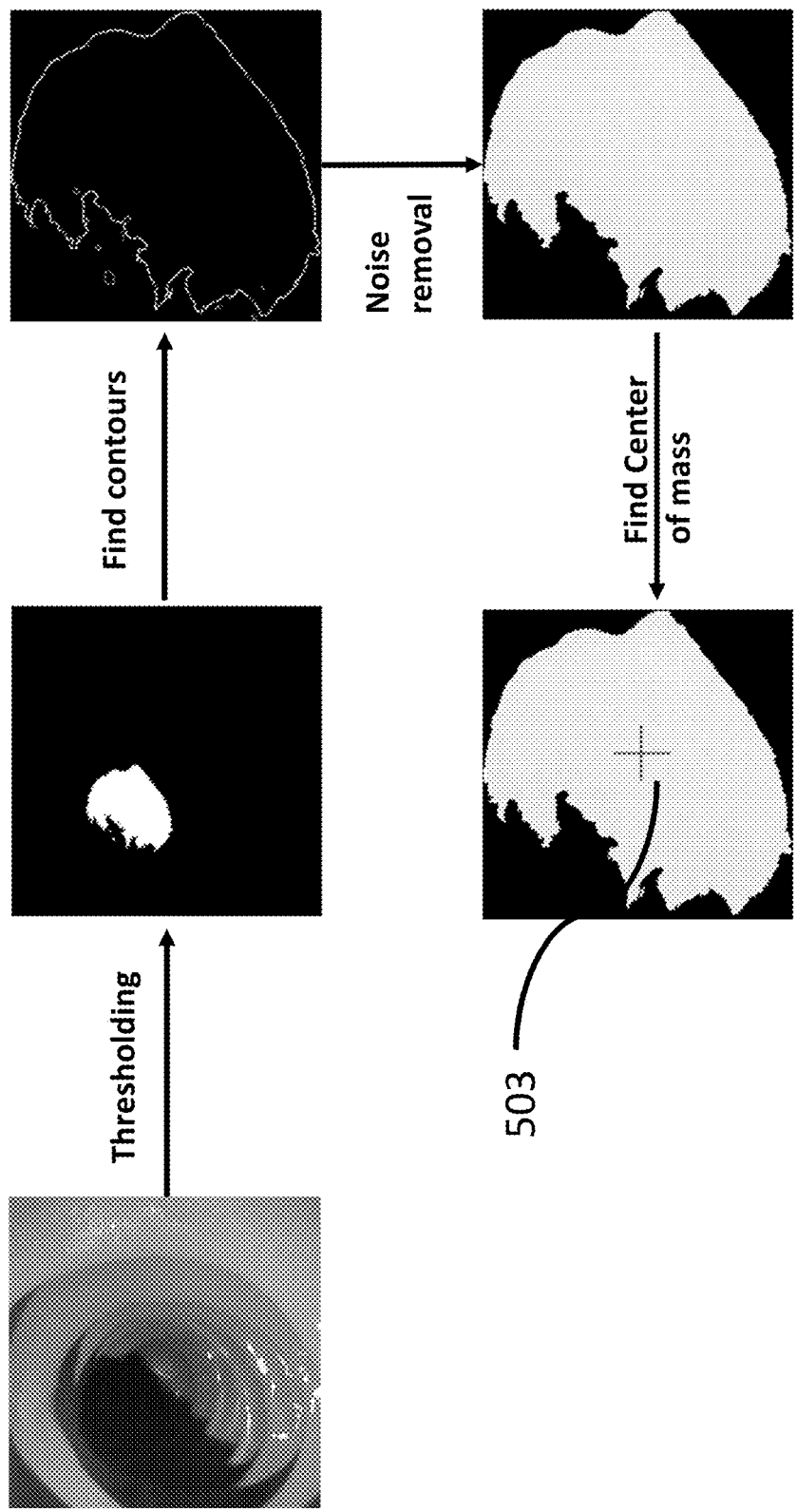
FIG. 5B shows one non-limiting example of a process for identifying the location of a lumen center or the location of an object of interest from image data.

In some embodiments, the location of the lumen center and/or the location of an object of interest may be input by a user, e.g., through use of a user software interface. In some embodiments, the location of the lumen center and/or location of an object of interest may be determined through processing of the input sensor data (or pre-processed input sensor data) by the machine learning method performed on the machine learning architecture. FIG. 5B shows an example of identifying the location of a lumen center 503 or location of an object of interest through automated processing of image data. The location of a lumen center or object of interest can be determined using various image processing or pattern recognition methods. For instance, the location may be obtained using an automated image feature extraction process comprising at least one of the following methods: intensity level analysis, contour mapping, noise removal, and computation of a center of mass. As shown in the example, light intensity thresholding may be applied to a captured image frame, after which the image data may be further processed to identify one or more contours. Once the lumen or the object of interest is segmented or extracted from the background, the location of the lumen center or object center may be identified, e.g., through the use of a center of mass calculation. It should be noted that, although a center of mass calculation is used to define the center of the lumen or object in the example, other approaches such as calculation of a geographical center may also be used to define the center location. Various other methods can also be used for recognizing the object of interest or lumen center including but not limited to, machine learning methods, automated light intensity gradient analysis processes, and the like.

Figure 5C:
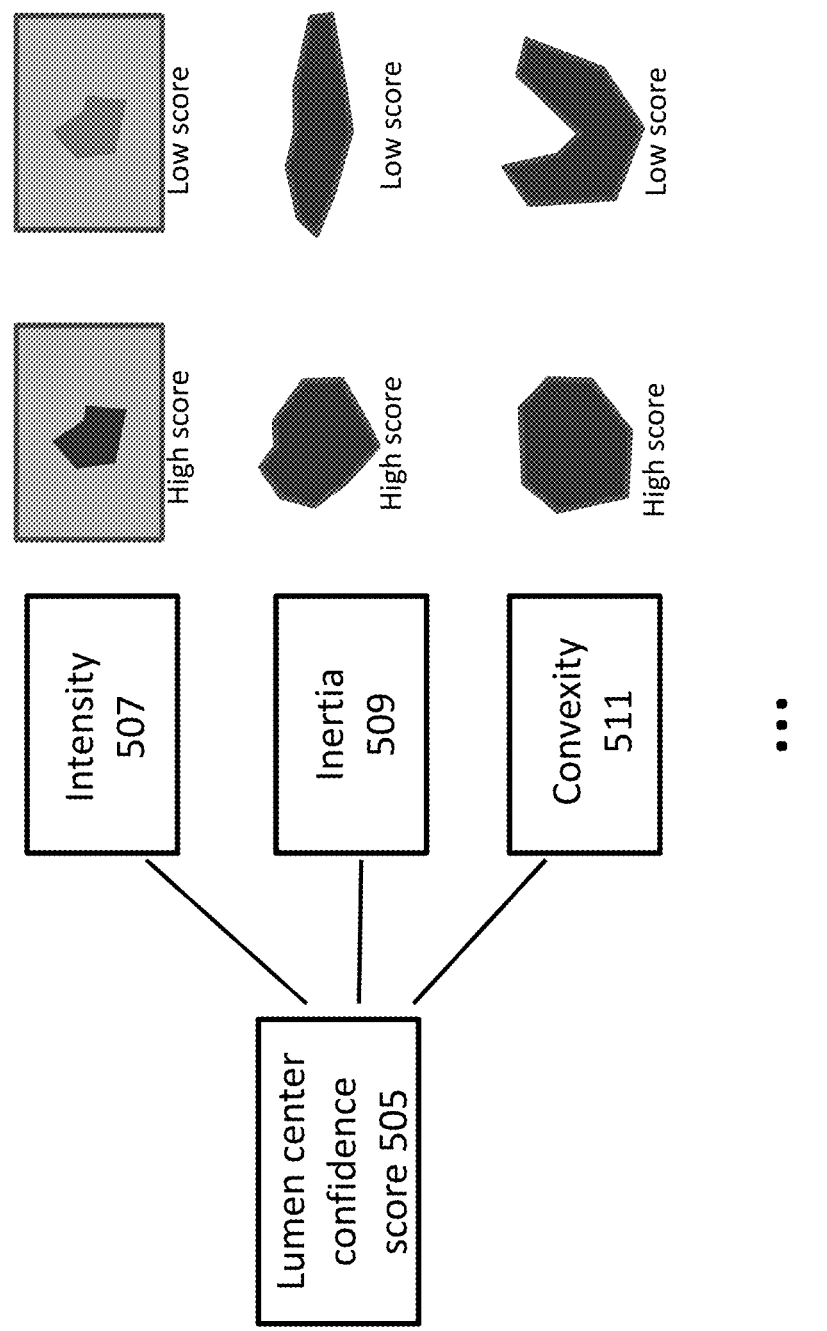
FIG. 5C shows one non-limiting example of a method for determining a lumen center confidence score based on measurement of light intensity values and moments of inertia and convexity calculations for image data.

In some embodiments, a confidence level for recognition of the object of interest or lumen center may be determined. The confidence level may be represented by a confidence score. For example, a lumen center confidence score may be determined from the image data. FIG. 5C shows one non-limiting example of a process for determining a lumen center confidence score 505. The lumen center confidence score may be determined from input image data to be processed by the machine learning method. The lumen center confidence score 505 may be determined based on one or more factors. In some embodiments, the one or more factors may include at least one of the following: a light intensity score 507, moment of inertia calculation 509, or a calculation of the convexity of the image of the object of interest 511. The one or more factors may be combined through, for example, simple summation or through calculation of a weighted average to determine the confidence score 505. For instance, an extracted image of the lumen or object of interest with high intensity may be associated with a high confidence score. In another example, the extracted feature showing the lumen center or object of interest having a low moment of inertia or low convexity value may be associated with a high confidence score.

The one or more factors and the confidence level can be correlated in a variety of ways, such as linearly correlated or non-linearly correlated (e.g., exponential). For example, the confidence level can be calculated or determined as a weighted sum of the various factors. The weighting coefficients may be indicative of significance of the associated factor. The weighting coefficients may be determined empirically, for example based on historic data. The weighting coefficients may be determined based on any suitable theory or any purposes. For instance, the weighting coefficients may vary according to the features to be identified. The weighting coefficients may or may not be equivalent. The one or more factors may be used to determine the confidence score in various other ways such as through the use of a multiplication factor.

In some cases, depth information about the lumen wall may also be extracted from the image data. The depth information may be provided based on, for example, image intensity. When the illumination provided by one or more light sources is uniform or homogeneous, the objects or obstacles that are close to the imaging device may reflect more light so as to appear as bright regions (or regions of glare) in the image. In some cases, the degree of light reflection or image intensity may be used to detect an object or a portion of colon wall when it is in close proximity to the distal end of the colonoscope. The objects or obstacles as detected may be located substantially in front of the distal end. For instance, the presence of image feature exhibiting glare or high brightness may be indicative of an obstacle in close proximity to the distal end of the colonoscope. In some cases, the distance between the objects or colon wall and the distal end may be estimated based on the degree of light reflection or image intensity. In some instances, a gradient map may be generated to correlate the distance of objects or depth of a scene with reflected light intensity. In some cases, the gradient map may be generated based on a pre-determined relationship between the distance and image intensity (e.g., reflected light intensity). In some cases, detection of obstacles or the colon wall in close proximity to the distal end using the light reflection method may cause the steering control system to provide a target steering direction such that the distal end of the colonoscope is steered away from the obstacle or colon wall to avoid contact.

Figure 6A:
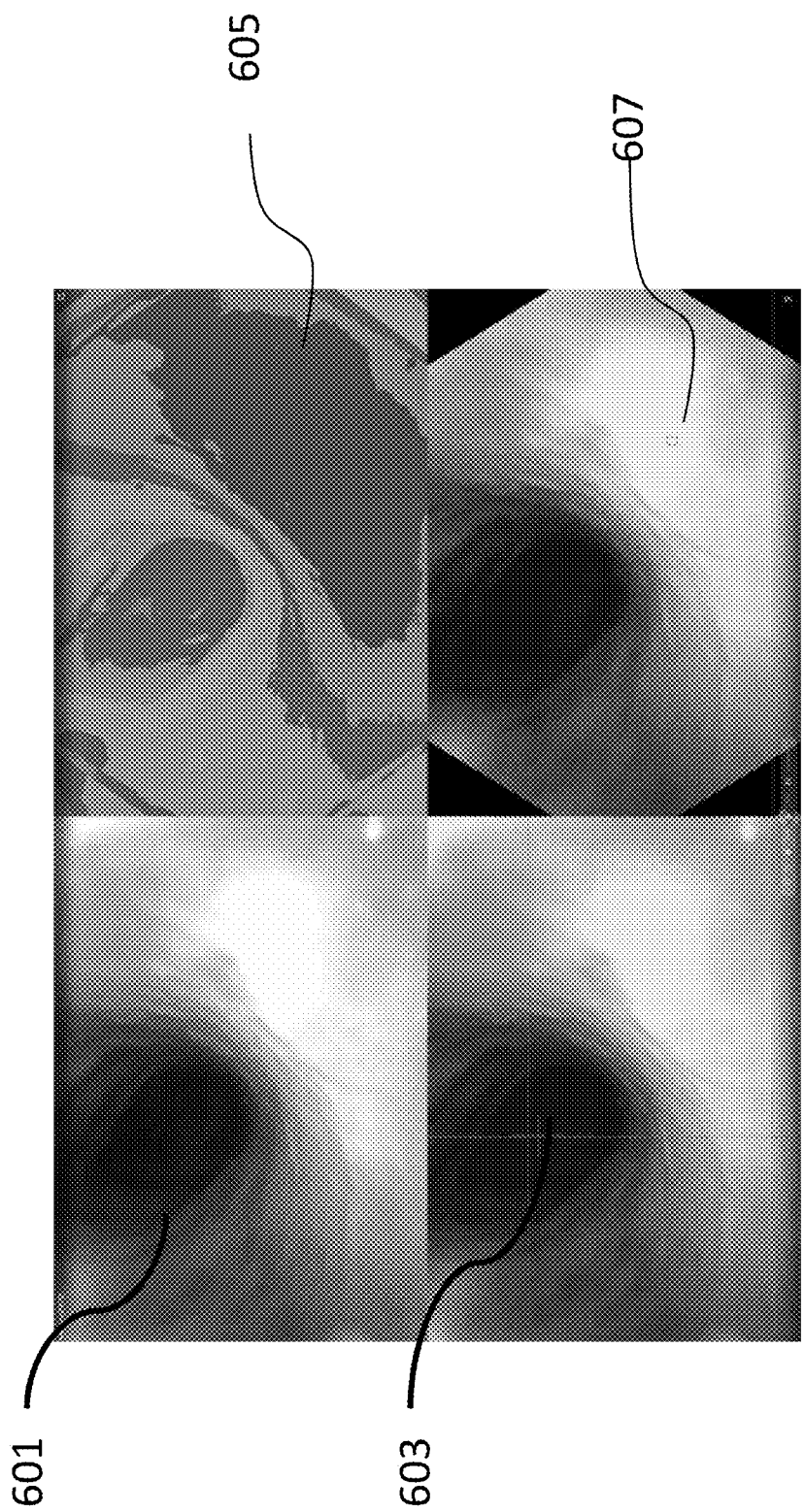
FIG. 6A and FIG. 6B show examples of image data processing methods used for providing information about the location of a lumen center position and depth information about features in the image.
Figure 6B:
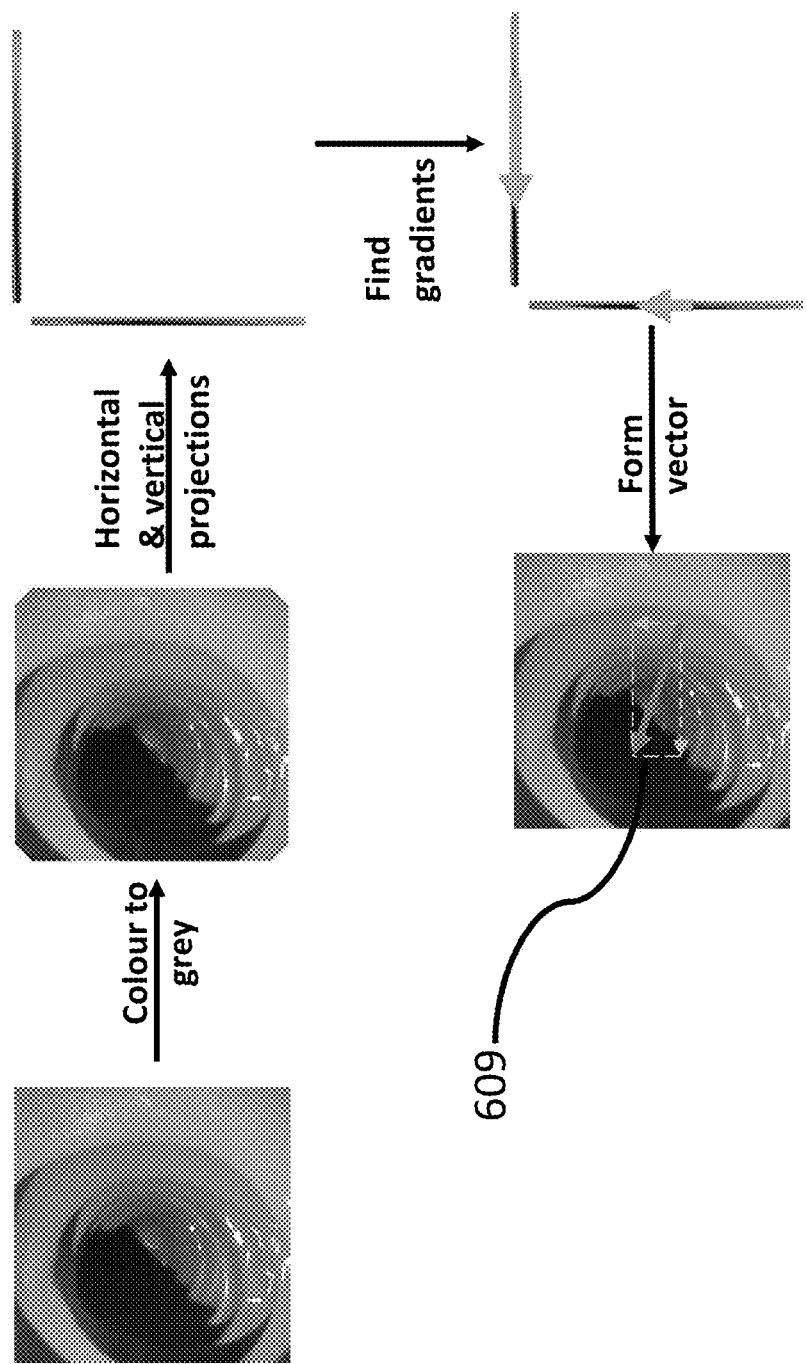

FIG. 6A and FIG. 6B show additional examples of the use of image data to provide information about the location of the lumen center and depth information about features in the image. In some embodiments, a light intensity gradient of the image frame may be part of the input data to be processed by the machine learning method. As described above, the position of the lumen center 601 may be determined using suitable image processing and analysis methods such as feature extraction. In some cases, the same image may also be used for providing depth information or for detection of an obstacle in close proximity. Alternatively, additional image data may be collected, e.g., from a second image sensor, for detecting obstacles by analyzing light reflection. The image data used for detecting obstacles may or may not be same image data used for locating a lumen center. The obstacle 607 may be detected based on light reflection method as described previously. In some instances, a gradient map 605 indicative of the relative or absolute distance of features perceived in the scene or depth information about the image may be generated. The gradient map, location of a detected obstacle, and/or location of the lumen center may be used by the steering system controller to determine a target direction and provide a steering control signal for control of the distal end 603 of the colonoscope. The target direction 603 may or may not be aligned with the lumen center.

As shown in FIG. 6B, the light intensity gradient 609 for an image frame may be obtained using a series of image processing steps. The gradient vector may be determined for the whole image frame or for a portion of the image frame. In the example, a greyscale image of a captured image may be generated which comprises light intensity distribution information. Gradients along the horizontal and/or vertical directions, or along a horizontal projection line and/or a vertical projection line, may be obtained for use in calculating a gradient vector 609. The gradient vector 609 may be included in the input data used to determine a steering control direction (and/or for various other applications) by the machine learning process.

In some cases, the lumen center may not be visible in the image. For instance, when the distal end reaches looping or bending sections of the colon, the lumen center may not be visible directly in the image. In this case, the locus of the lumen center may be estimated or obtained indirectly. For example, the locus of the lumen center may be estimated based on that determined for previous image data. The locus of the lumen center may be estimated based on motion estimation or motion vectors obtained from the image analysis. For instance, a sequence of positions of the lumen center may be obtained from a sequence of images, and a motion vector between consecutive images may be calculated from the consecutive positions of the lumen center and the rate of advancement of the colonoscope. The motion vector or motion estimation method may also be performed using any other features within the image. The motion vector and position of the lumen center in the last image may be used to estimate or predict the position of the lumen center in the following image frame. Various methods (e.g., optical flow, phase correlation, block-based methods, Lucas-Kanade method, Horn-Schunk method, Buxton-Buxton method, Black-Jepson method, discrete optimization methods, pixel recursive algorithms, RANSAC, etc) may be used to obtain the motion vector and/or estimate the location of the lumen center. In some cases, the methods used may be selected according to the texture of the colon lumen or other features perceived in the images.

In some instances, an image frame may be pre-processed (i.e., analyzed coarsely) to determine whether the lumen center can be determined directly prior to performing the motion vector calculation. For example, images may be examined for the presence of a visible lumen center by extracting the specific feature of the lumen center using, for example, the pattern matching or pattern recognition methods as described elsewhere herein.

Machine Learning Algorithms for Integrating and Processing Sensor Data:

In some embodiments, a target direction and/or steering control signal may be determined from sensor input data using an artificial intelligence or machine learning method. In some cases, the artificial intelligence method employed may comprise an artificial neural network (ANN). In some cases, the artificial intelligence method may be a deep machine learning method. In some cases, the method may be a supervised deep machine learning method. The steering control system may employ the artificial neural network (ANN) to determine steering direction and/or to provide steering control signals to the robotic endoscope. The artificial neural network may employ any type of neural network model, such as a feedforward neural network, radial basis function network, recurrent neural network, or convolutional neural network, and the like. In some embodiments, the steering control system may use a pre-trained ANN architecture. The steering control system may process input data provided by a plurality of sensors as described above, and generate control signals or target direction in real-time. In some instances, e.g., when the sensor data comprises image data, the sensor data may be pre-processed, e.g., using one or more image processing methods, prior to sending it as input to the ANN.

As used herein, the term "real time" refers to the rate at which sensor data is acquired, processed, and/or used by a machine learning or artificial neural network algorithm to update a prediction of steering direction and/or steering control signal in response to changes in one or more of the input data streams. In general the update rate for the steering control signal provided by the disclosed automated steering control methods and systems may range from about 10 Hz to about 1000 Hz. In some embodiments, the update rate may be at least 10 Hz, at least 20 Hz, at least 30 Hz, at least 40 Hz, at least 50 Hz, at least 100 Hz, at least 200 Hz, at least 300 Hz, at least 400 Hz, at least 500 Hz, at least 600 Hz, at least 700 Hz, at least 800 Hz, at least 900 Hz, or at least 1000 Hz. In some embodiments, the update rate may be at most 1000 Hz, at most 900 Hz, at most 800 Hz, at most 700 Hz, at most 600 Hz, at most 500 Hz, at most 400 Hz, at most 300 Hz, at most 200 Hz, at most 100 Hz, at most 50 Hz, at most 40 Hz, at most 30 Hz, at most 20 Hz, or at most 10 Hz. Those of skill in the art will recognize that the update rate may have any value within this range, for example, about 24 Hz.

As noted above, in some cases, weighting factors or other computational parameters of the neural network can be learned in a training phase. For instance, the parameters may be trained using the input data from a training data set and a gradient descent or backward propagation method so that the output value(s) (e.g., target steering direction or steering control signal) that the ANN computes are consistent with the examples included in the training data set. The parameters may be obtained from a back propagation neural network training process that may or may not be performed using the same hardware as the real-time control or application process.

Figure 7:
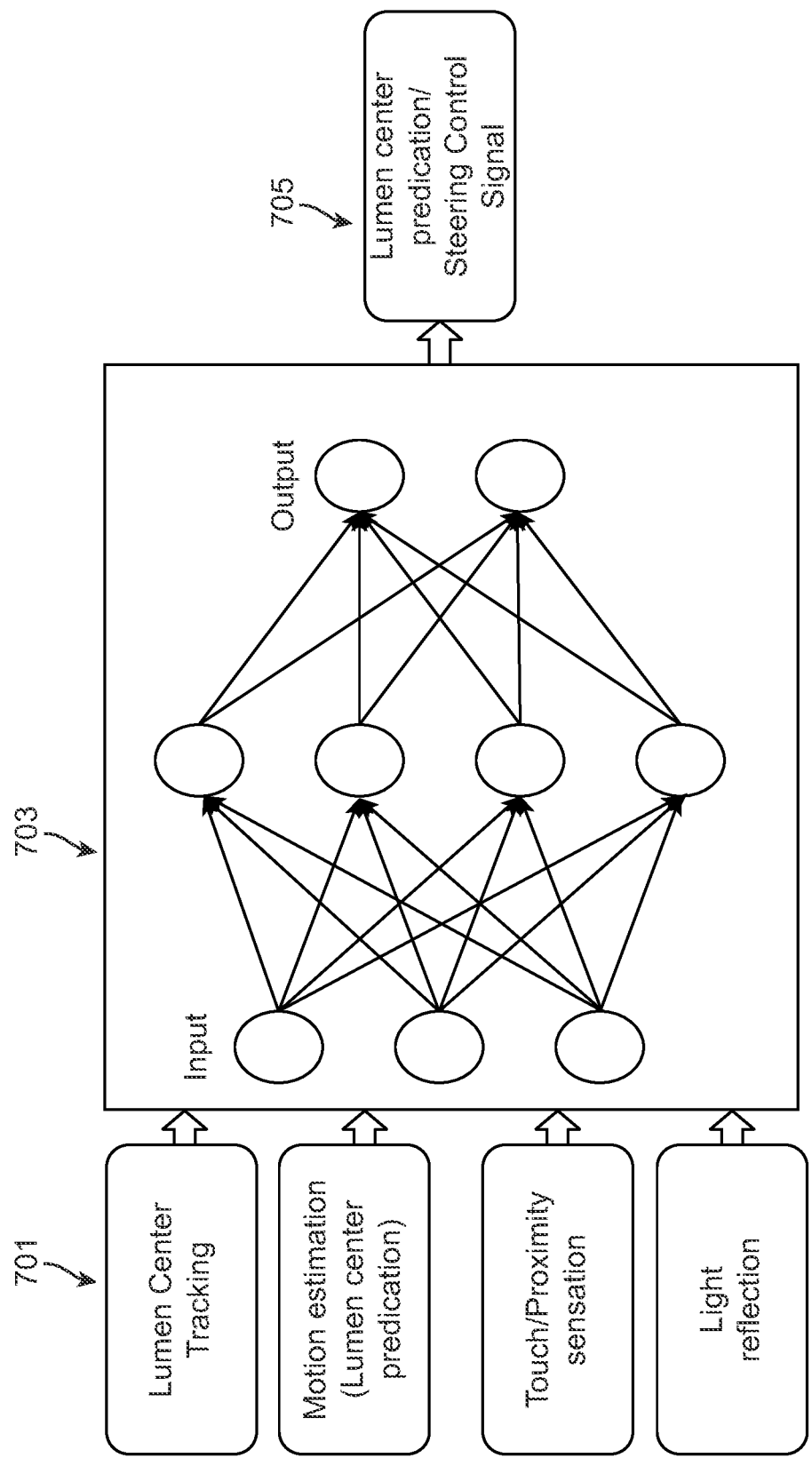
FIG. 7 shows a schematic diagram for an exemplary artificial neural network (ANN) used for steering control of a robotic endoscope system, for example, a robotic colonoscope.

FIG. 7 shows an exemplary ANN 703 used for automated steering control of a robotic colonoscopy system. The ANN 703 may comprise multiple layers. For example, the ANN system may comprise at least an input layer, a number of hidden layers and an output layer. As illustrated in FIG. 7, an ANN system may comprise any total number of layers, and any number of hidden layers. The simplest architecture of a neural network starts with an input layer followed by a sequence of intermediate or hidden layers, and ends with output layer. The hidden or intermediate layers may act as learnable feature extractors, while the output layer in this example provides a predicted target steering direction or steering control signal.

Each layer of the neural network may comprise a number of neurons (or nodes). A neuron receives input that comes either directly from the input data (e.g., sensor data, image data, processed sensor or image data, object recognition data, motion tracking data, etc.) or the output of other neurons, and performs an specific operation, e.g., summation. In some cases, a connection from an input to a neuron is associated with a weight (or weighting factor). In some cases, the neuron may sum up the products of all pairs of inputs and their associated weights. In some cases, the weighted sum is offset with a bias. In some cases, the output of a neuron may be gated using a threshold or activation function. The activation function may be linear or nonlinear. The activation function may be, for example, a rectified linear unit (ReLU) activation function or other functions such as saturating hyperbolic tangent, identity, binary step, logistic, arcTan, softsign, parameteric rectified linear unit, exponential linear unit, softPlus, bent identity, softExponential, Sinusoid, Sinc, Gaussian, sigmoid functions, or any combination thereof.

The output 705 of the neural network may be a control signal or a target direction. The ANN may take input data from a plurality of sensors, process it using the multiple layers of neurons, and output a control signal for controlling the steering direction of the colonoscope. The control signal may be transmitted to an actuation unit as described elsewhere herein. In some instances, data relating to the dynamics or kinematics of the robotic system may also be incorporated into the ANN to generate control signals that are sent to the actuation unit. In some cases, the output may be a target direction. The target direction may be transmitted to a controller of the actuation unit to effectuate steering direction of the colonoscope. In this case, the steering control system may not require knowledge of the dynamics or kinematics of the robotic system.

In some instances, the input data 701 supplied to the input layer of the neural network may be provided by at least an image sensor and a touch or proximity sensor. In some instances, the input data may be provided by an image sensor only. In some instances, the input data may be provided by a touch or proximity sensor only. The input data may comprise information about the location of a lumen center, location of one or more objects in close proximity to the distal end of the colonoscope, or a relative position of the distal end with respect to the lumen center or colon wall. The neural network may be trained using one or more training data sets to learn a mapping between the input data and the output control signals or target direction. The input data can be of a variety of forms. In some cases, the input data may comprise raw sensor data such as the image captured by a camera and/or proximity sensor data. In some cases, the input data may comprise processed sensor data such as an intensity gradient map indicative of depth information for the colon wall within the field-of-view, the location of the lumen center or of obstacles, the relative position of the distal end of the colonoscope with respect to the colon wall or lumen center, or motion vectors derived from sequential image data. Depending on the forms of input data used, the input data set may have different dimensionalities, such as one, two, three, four, five, six, seven, or more dimensions.

In some cases, the input data may be changing with different environments, e.g., as the colonoscope advances through the colon. In some cases, the integrity of the input data may change. For instance, when the location of the lumen center cannot be extracted directly from image, the image data may be analyzed using the motion based method to estimate the location of the lumen center. In this case, the input data may comprise the estimated lumen center position but not include the raw image data. In other instances, image sensor data and/or touch or proximity sensor data may be examined to determine sensor integrity. If it is detected that the sensor has malfunctioned or that the quality of the sensor data does not meet certain threshold (e.g., a specified signal-to-noise ratio), the corresponding sensor data may not be included in the input data. Alternatively, all the sensor data may be included in the input data set and analyzed by the ANN regardless of sensor integrity or data quality.

Other types of machine learning methods, such as recurrent neural networks (RNN) or convolutional neural network (CNN) systems (for the processing of image data), can also be used in the disclosed methods and systems for determining the steering direction or control signal. CNN are commonly composed of layers of different types: convolution, pooling, upscaling, and fully-connected neuron layers. In some cases, an activation function such as rectified linear unit may be used in some of the layers. In a CNN system, there can be one or more layers for each type of operation. A CNN system may comprise any number of layers in total, and any number of layers for different types of operations. The simplest convolutional neural network architecture starts with an input layer followed by a sequence of convolutional layers and pooling layers, and ends with fully-connected layers. In some cases, the convolutional layers are followed by a layer of ReLU activation function. Other activation functions can also be used, for example the saturating hyperbolic tangent, identity, binary step, logistic, arcTan, softsign, parameteric rectified linear unit, exponential linear unit, softPlus, bent identity, softExponential, Sinusoid, Sinc, Gaussian, the sigmoid function and various others. The convolutional, pooling and ReLU layers may act as learnable features extractors, while the fully connected layers acts as a machine learning classifier.

In some cases, the convolutional layers and fully-connected layers may include various computational parameters, e.g., weights, biases, and threshold values. These parameters can be learned in a training phase. The parameters may be trained using a training data set and gradient descent method so that the output values that the CNN computes are consistent with the examples included in the training data set. The parameters may be obtained from a back propagation neural network training process that may or may not be performed using the same hardware as the production or application process.

Each convolution layer may comprise a plurality of parameters for the convolution operation. One or more filters may be implemented in each convolution layer, and used to convolve around an input volume (e.g., a two-dimensional subsection of an image) and produce an output volume (e.g., a processed subsection of the image having a reduced pixel count). Each filter may comprise one or more parameters or weights. In some embodiments, the parameters may also include biases (i.e., parameters that permit the activation function to be shifted).

The size of the output volume of the convolution layer may also depend on hyper-parameters, i.e., variables that are set before actually optimizing or training a neural network model's adjustable parameters. For example, some hyper-parameters may specify the structure of the neural network, while others may determine how the network is trained. In some cases, the hyper-parameters may include the number of nodes (or neurons) per layer, the number of hidden layer used, the depth (i.e., the number of hidden layers plus one (for a feedforward neural network) or the effective number of layers through which a signal is propagated (for a recurrent neural network)), stride (i.e., the shift used by a filter in a CNN convolution layer as it convolves around an input volume), and zero-padding (i.e., addition of a set of zeros along the borders of an input volume to avoid excessive shrinking of the output volume during convolution).

In some instances, the number of nodes used in the input layer of the ANN (which enable sub-sampling of an image frame and additional sensor inputs) may range from about 10 to about 10,000 nodes. In some instances, the number of nodes used in the input layer may be at least 10, at least 100, at least 200, at least 300, at least 400, at least 500, at least 600, at least 700, at least 800, at least 900, at least 1000, at least 2000, at least 3000, at least 4000, at least 5000, at least 6000, at least 7000, at least 8000, at least 9000, or at least 10,000. In some instances, the number of node used in the input layer may be at most 10,000, at most 9000, at most 8000, at most 7000, at most 6000, at most 5000, at most 4000, at most 3000, at most 2000, at most 1000, at most 900, at most 800, at most 700, at most 600, at most 500, at most 400, at most 300, at most 200, at most 100, or at most 10. Those of skill in the art will recognize that the number of nodes used in the input layer may have any value within this range, for example, 512 nodes.

In some instance, the total number of layers used in the ANN (including input and output layers) may range from about 3 to about 20. In some instance the total number of layer may be at least 3, at least 4, at least 5, at least 10, at least 15, or at least 20. In some instances, the total number of layers may be at most 20, at most 15, at most 10, at most 5, at most 4, or at most 3. Those of skill in the art will recognize that the total number of layers used in the ANN may have any value within this range, for example, 8 layers.

In some instances, the total number of learnable parameters, e.g., weighting factors, biases, or threshold values, used in the ANN may range from about 1 to about 10,000. In some instances, the total number of learnable parameters may be at least 1, at least 10, at least 100, at least 500, at least 1,000, at least 2,000, at least 3,000, at least 4,000, at least 5,000, at least 6,000, at least 7,000, at least 8,000, at least 9,000, or at least 10,000. Alternatively, the total number of learnable parameters may be any number less than 100, any number between 100 and 10,000, or a number greater than 10,000. In some instances, the total number of learnable parameters may be at most 10,000, at most 9,000, at most 8,000, at most 7,000, at most 6,000, at most 5,000, at most 4,000, at most 3,000, at most 2,000, at most 1,000, at most 500, at most 100 at most 10, or at most 1. Those of skill in the art will recognize that the total number of learnable parameters used may have any value within this range, for example, about 2,200 parameters.

Optimization of an Automated Colonoscope Steering Mechanism:

As mentioned above, various parameters, e.g., threshold values, biases, or weights, of the neural network may be adjusted during a training phase. A number of training datasets may be supplied to the neural network for training the parameters, e.g., weights, biases, and threshold values, and various other characteristics that define the neural network. In another aspect of the invention, a method for using a machine learning architecture to optimize an automated colonoscope steering mechanism is provided. The method may comprise: providing at least a first set of input sensor data obtained from at least a first type of sensor; providing a plurality of training datasets, wherein a training dataset comprises at least a first set of known input sensor data for at least the first type of sensor and a corresponding set of known output steering control signals; and analyzing the plurality of training datasets using the machine learning architecture to determine a set of parameters, e.g., weighting parameters, wherein the learned parameters are subsequently used by the machine learning architecture to provide a steering control signal for the automated colonoscope steering mechanism that is adaptive to changes in the at least first set of input sensor data.

Figure 8A:
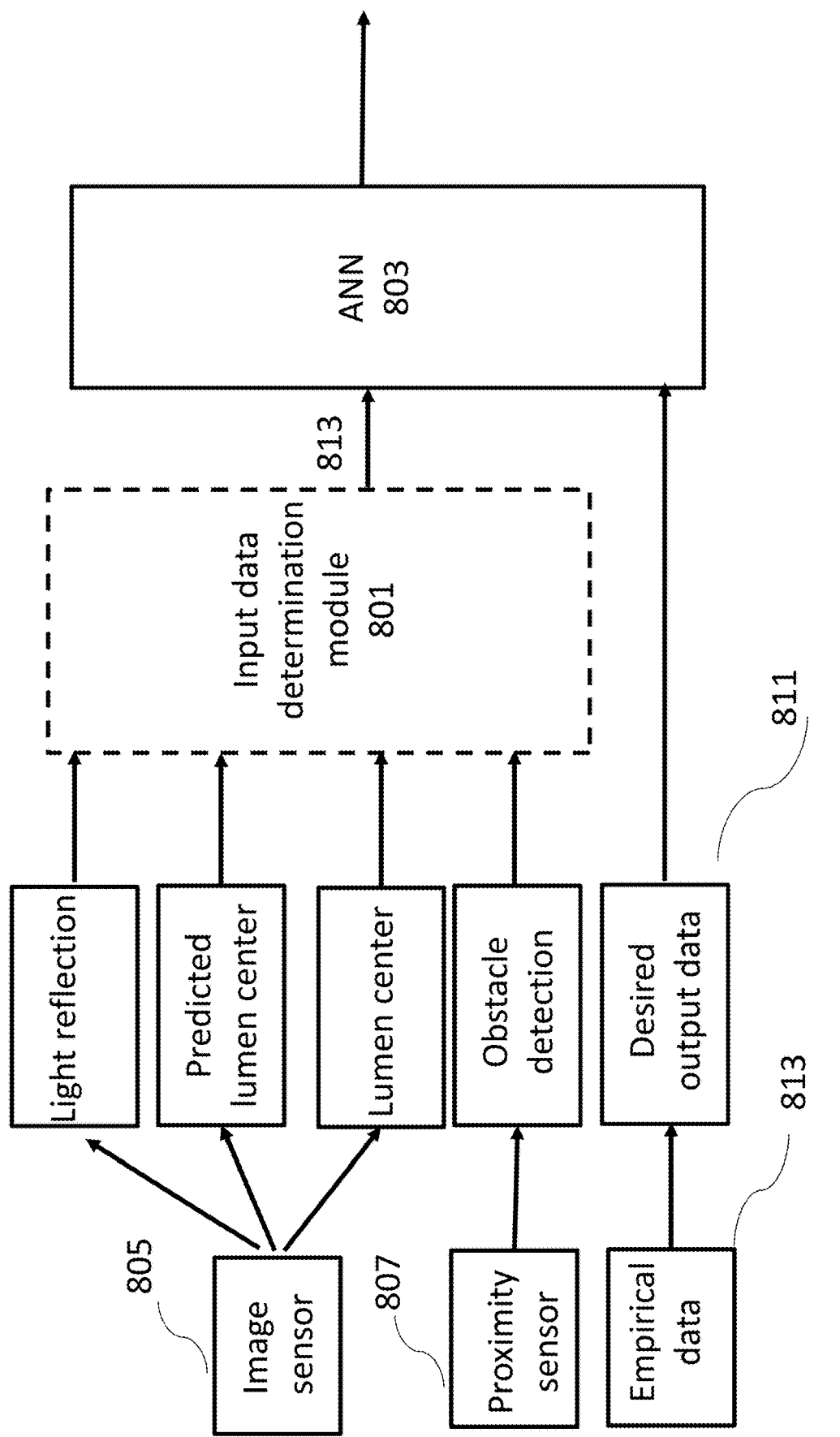
FIG. 8A and FIG. 8B schematically illustrate examples of input sensor data and training datasets supplied to a machine learning algorithm, e.g., a neural network, for the purpose of refining operational parameters of the algorithm and providing a steering control signal for a robotic endoscope that adapts in real-time to changes in one or more of the input sensor data streams.

FIG. 8A schematically illustrates exemplary training datasets supplied to a neural network 803 for learning the parameters of the network. In some embodiments, the training datasets may comprise input data 813 and desired output data 811. The desired output data may be paired with input data. In some embodiments, the desired output data may be control signals supplied to an actuation unit for effectuating movement of the colonoscope. In some embodiments, the desired output data may be a target navigation direction supplied to a controller of the colonoscope such that the distal end may be steered towards the target navigation direction. In some embodiments, the desired output data may be control instructions supplied to a controller of the colonoscope.

In some cases, the output steering control signals of the training datasets may be obtained from sets of empirical steering control instructions provided to the steering mechanism of a robotic colonoscope. The robotic colonoscope may be the same as the colonoscope as described in FIG. 1A. In some cases, a steerable distal end of the robotic colonscope may comprise a bendable/extendable section as illustrated in FIG. 1B, wherein bending is accomplished through the actuation of a series of embedded tendons running through the bendable/extendable section. The steering mechanism may be the same mechanism as described in FIG. 2. The robotic colonoscope from which the training datasets obtained may or may not be the same robotic colonoscope to be controlled using the trained ANN. In some cases, the output steering control signals may be the steering control instructions generated in response to the input sensor data of the training datasets by one or more skilled operators of the robotic colonoscope. For instance, a skilled operator, surgeon, or endoscopist may be provided with the image data captured by the cameras and/or information about obstacles detected by the proximity sensors, and the operator or surgeon may then instruct the colonoscope to move based on the perceived information. The control instructions may, for example, instruct the colonoscope to steer away from obstacles and towards the lumen center. The control instruction may be indicative of a target navigation direction towards which the colonoscope may be guided. The target navigation direction may or may not be aligned with the lumen center. Various use interfaces can be used to obtain the control instruction such as such as a button, joystick, thumbstick, touchpad, motion control, voice control, accelerometer, haptic feedback, or the like. In some cases, the desired output data may be generated based on a combination of surgeon-provided instructions and a pre-determined relationship between input sensor data and control instructions. For instance, based on the input sensor data, a preliminary navigation direction may be calculated using the pre-determined relationship and then further corrected or modified by a surgeon.

The control instructions or target navigation directions may be recorded along with input data and used as the training datasets. In some instances, the control signal supplied to one or more actuation units may be generated based on the control instructions and the control signal may be recorded and used as the desired output data.

In some cases, the robotic colonoscope used to generate the empirical data for the training datasets may share the same motion dynamics or various other properties as those of the colonoscope to be controlled. The colonoscope used for training the neural network may or may not be the same colonoscope to be controlled later by the trained neural network. In some cases, the empirical data obtained from a plurality of colonoscope systems may be used for training the neural network. The plurality of colonoscope systems may or may not be exactly the same. For instance, when the output data is the control signal to be sent to an actuation unit, the colonoscope systems used to generate the training data may share the same motion dynamics or kinematics properties. In some instances, when the output data is the navigation direction, the plurality of colonoscope systems may differ in terms of motion dynamics, and appropriate control signals may be generated by a local controller of the colonoscope according to the target navigation direction.

In some instance, the input data of the training dataset may comprise sensor data derived from at least one proximity sensor. In some instances, the input data of the training dataset may comprise sensor data from at least one image sensor. In some instances, the input data of the training datasets may comprise sensor data derived from at least one proximity sensor 807 and at least one optical image sensor 805. The sensor data collected from the optical image sensor may comprise information indicative of a center position of a colon lumen or a location of an obstacle relative to the guiding portion (e.g., distal end) of the robotic colonoscope. The center position of the colon lumen may be obtained directly by analyzing an image of the colon lumen (e.g., using automated image processing and feature extraction methods), or by calculating a predicted or estimated center position of the colon lumen (e.g., by calculating motion vectors), or a combination of both. For instance, motion vectors obtained from previously collected image frames may be used to estimate the center position of the colon lumen, and the estimated position may be used as the input data when the lumen center is not shown in the image data. In other instances, estimates of the location of lumen center derived directly by using the feature extraction method and by using the motion-based estimation method respectively may be combined to determine the location of the lumen center. Various methods may be used for combining the two location data estimates to form a prediction, such as weighted sum approaches, Kalman filters, Extended Kalman filters, complementary filters, and the like. The sensor data collected from the proximity sensor may comprise information indicative of the position of the guiding portion of the robotic colonoscope relative to a wall of the colon lumen.

Figure 8B:
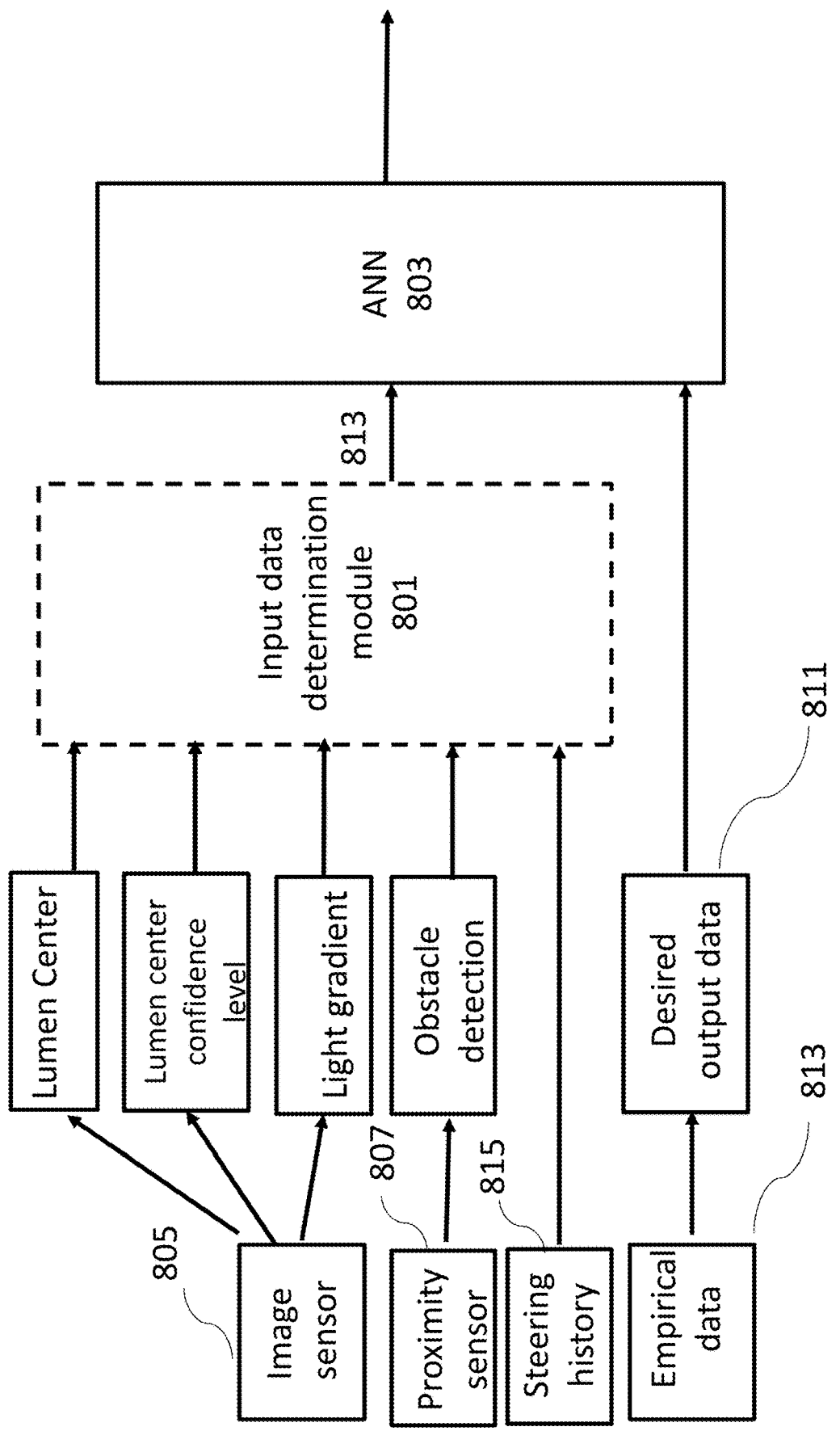

FIG. 8B schematically illustrates another example of input sensor data and training datasets that may be supplied to a machine learning algorithm 803, e.g., a neural network, for learning the weighting factors and other parameters of the network that are used to map input values to the desired output. The training process is similar to the example as described in FIG. 8A. The training data may comprise data on the location of the lumen center, confidence levels for the determination of lumen center, light intensity gradient data, obstacle detection data, steering history data 815, empirical steering data 813 (e.g., data provided through operation of the endoscope or colonoscope by a skilled operator) and desired output data 811. The location of the lumen center, the confidence level of having correctly identified the lumen center, and light intensity gradient data can be derived from image data captured by the image sensor 805 as described elsewhere herein. For instance, the location of the lumen center can be determined using the method as described in FIG. 5B, the confidence level for the determination of lumen center may be a confidence score determined based on one or more factors as described in FIG. 5C, and the light intensity gradient for an image (or portion of an image) may be used to determine a gradient vector using the method as described in FIG. 6B. Obstacle detection data can be obtained from proximity sensor data 807. For instance, the obstacle detection data may be the proximity vector obtained as described in FIG. 4B.

The input data may further comprise steering history data 815. The steering history data may comprise information related to recent steering control actions. For instance, for each steering control instruction or command, the colonoscope may be steered by a steering vector in 2D or 3D space. The steering vector may correspond to the motion of the distal end of the colonoscope. The steering history data may be generated based on a plurality of steering vectors. For example, the steering history data may be an average or median of the recent steering vectors over a specified period of time. In another example, the steering history data may be determined through extrapolation of recent steering vectors. The steering history data may comprise an average or median value of the steering vectors over the past 0.1, second, 1 second, 2 seconds, 3 seconds, 4 seconds, 5 seconds, 10 seconds, 20 seconds, 30 seconds, 40 seconds, 50 seconds, 1 minute, or any time value within this range.

Figure 8C:
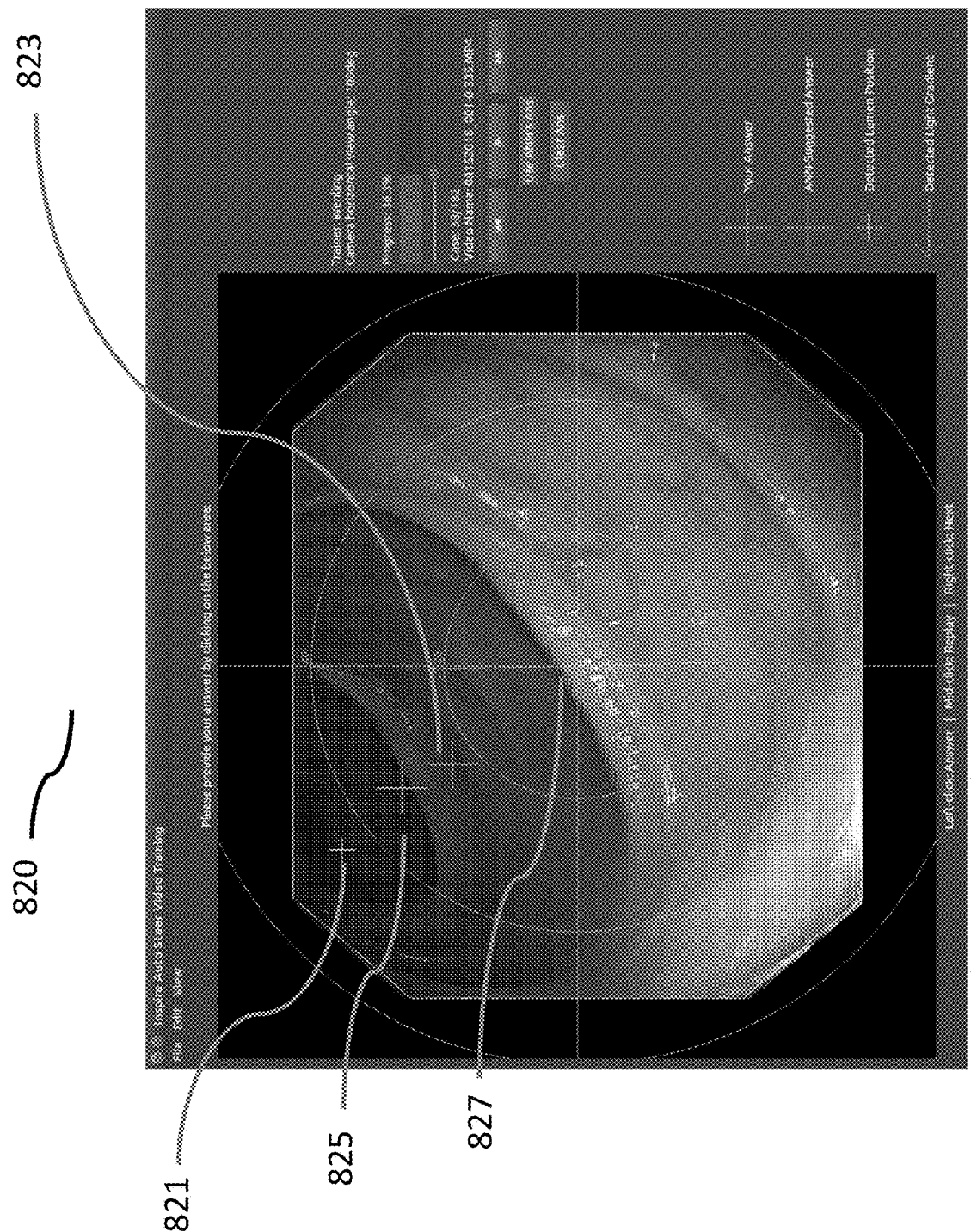
FIG. 8C shows an exemplary user interface for a training process, in accordance with embodiments of the invention.

The input data may be obtained from a training process or stored in a database. In some cases, the sensor data and associated steering history data may be collected prior to obtaining the desired output data 811. In some cases, the sensor data and associated steering history data may be collected concurrently with obtaining the desired output data. FIG. 8C shows an exemplary user interface 820 for a training process, in accordance with embodiments of the invention.

The user interface 820 may be configured to receive user input and to output sensor data and/or steering control information to a user. Examples of UI's include, without limitation, a graphical user interface (GUI) and web-based user interface. The user input may comprise at least a desired output data indicating a desired steering direction. For instance, a skilled operator, surgeon, or endoscopist may be provided with image data and augmented information through the UI such that the surgeon may then instruct the colonoscope to move based on the perceived information. The user interface may include a screen such as a display screen, touch screen and any other user interactive external device such as handheld controller, mouse, joystick, keyboard, trackball, touchpad, button, verbal commands, gesture-recognition, touch-capacitive sensors, foot switch, or any other device. The graphical user interface may be displayed on a display screen. For example, the display screen may comprise a light-emitting diode (LED) screen, OLED screen, liquid crystal display (LCD) screen, plasma screen, or any other type of screen.

Some or all of the sensor data may be displayed on the GUI. In some cases, an image frame with augmented information may be displayed on the display screen. The augmented information may comprise still and/or moving images and/or information (such as text, graphics, charts, plots, and the like) to be overlaid onto an image frame displayed on a screen. The image frame is collected by an imaging device as described elsewhere herein. The image frame may be provided in real-time or pre-stored in a storage device.

The augmented information superimposed onto the image frame may comprise a plurality of graphical elements. The plurality of graphical elements may comprise any shapes, colors and sizes to indicate, for example, a location of the detected lumen center 821, a suggested steering direction 823 generated by current machine learning method, or a light intensity gradient 827 that provides depth information for features within the image. The detected lumen center may be obtained using feature extraction methods as described elsewhere herein. In some cases, a user input steering direction 823 may be overlaid on the image. For instance, when a user or surgeon clicks a location on the image indicating a desired direction or a position of the lumen center, the corresponding location or steering vector may be used as input data for training the machine learning architecture.

As noted, the desired output steering control data used for training the machine learning algorithm may be data obtained during trial runs where the robotic endoscope is operated by a surgeon or other skilled operator. For example, surgeons may be presented with live and/or pre-recorded video images via a user interface such as the one shown in FIG. 8C during which the surgeon may be prompted to identify and input the location of the lumen center in the image via the user interface. In some cases, the size of the training dataset may be further extended by incorporating simulated image data as well as live and/or pre-recorded images. For example, in some instances the training dataset may be extended by adjusting one or more properties of the input image data pertaining to the same desired output lumen center location. For example, the intensity of one or more color channels (e.g., the red, green, or blue channel) in a color image may be shifted by a specified value while the lumen center location remains the same, thereby creating a simulated image for which the correct location of the lumen center has been previously identified. In another example, the brightness and/or contrast of the image may be modified, or noise and/or random features may be added to the image while the correct output lumen center location remains the same. In some instances, the training datasets may be extended by adjusting one or more properties of the input image data in such a way that the correct location of the lumen center is changed according to a specified transformation relationship. For example, the input image data may be distorted or translated in one or more directions (e.g., horizontal, vertical, radial, perspective), rotated in one or more directions, and correct location of the lumen center location is transformed accordingly. Table 1 summarizes examples of the types of image parameters or image transformations that may be applied to create simulated data for use in training the machine learning algorithms used in the disclosed steering control mechanisms.

TABLE 1

Examples of image parameters that may be adjusted to create simulated image data for training machine learning algorithms.

| Variation Category | Simulation Effect | Simulation Method | Expected Impact on Lumen Center (position/direction) |
|---|---|---|---|
| Colon, camera | Color: red +/−10% | Tune red channel | No impact |
| Colon, camera | Color: green +/−10% | Tune green channel | No impact |
| Colon, camera | Color: blue +/−10% | Tune blue channel | No impact |
| Colon, camera | Color saturation +/−20% | Tune saturation | No impact |
| Colon | Introduce 1~5 random objects, each with an area of 0-10% of lumen region | Overlay image with small objects having random shape, color, and/or intensity at random positions | No impact |
| Camera | Noise +/−10 gl | Overlay image with gaussian noise | No impact |
| Camera | Radial distortion +/−5% | Radially distort | Distorted |
| Colon, camera | Brightness +/−20% | Tune brightness | No impact |
| Colon, camera | Contrast +/−20% | Tune contrast | No impact |
| View | Scale +/−50% | Scale | Scaled |
| View | Horizontal scale +/−50% | Horizontal scale | Scaled |
| View | Vertical scale +/−50% | Vertical scale | Scaled |
| View | Horizontal translation +/−20% of view width | Horizontal translation | Translated |
| View | Vertical translation +/−20% of view height | Vertical translation | Translated |
| View | Orientation 0~360deg | Rotate | Rotated |
| View | Horizontal perspective distortion +/−20% | Horizontal perspective distort | Distorted |
| View | Vertical perspective distortion +/−20% | Vertical perspective distort | Distorted |

Sensor Data Collection for Training and Real Time Steering Control:

In some cases, sensor data derived from different sensors may be collected at the same time point. Alternatively, sensor data derived from different sensors may not be collected at the same time point. Different types of sensor data may or may not be obtained at the same frequency. In some cases, when different types of sensor data are not collected at the same time point or the same acquisition rate, time stamps may be used to register the different types of data. The image sensor data may be acquired and/or processed at a rate of at least 5 HZ, 10 HZ, 20 HZ, 30 HZ, 40 HZ, 50 HZ, 60 HZ or 80 HZ. The touch or proximity sensor data may be obtained at a data acquisition rate of at least, 10 HZ, 20 HZ, 40 HZ, 60 HZ, 80 HZ, 100 HZ, 200 HZ, 400 HZ, 600 HZ, 800 HZ, or 1000 HZ.

In some cases, the sensor data may be used as input data directly. For instance, images captured by a camera that provide information about the position of the guiding portion relative to the colon wall may be supplied to the neural network as input data. In some cases, data derived from pre-processing of sensor data, such as gradient maps, motion vectors, or locations of the lumen center extracted from images, may be supplied to the neural network as input data. In some embodiments, e.g., when the input data are image data, the neural network may be capable of adapting to a loss of or change in the integrity of the input data. For example, a loss of data integrity may comprise a failure of the automated image feature extraction step to identify a center position of the colon lumen. The adaptation to a loss of or change in the integrity of image data in the case of failure to identify a lumen center position may be achieved by including both the image data and the motion vector-derived estimate of the lumen center position in the input data for the ANN.

In some instances, the input sensor data may be analyzed for a loss of or change in data integrity prior to being supplied to the neural network as input data. For example, the sensor data may be pre-examined for a loss of or change in input data integrity and, based on the evaluation of data integrity, the selection of input data may be adjusted. An input data determination module 801 may be utilized to determine the choice of input data. For example, in the case of a failure of the automated image feature extraction step to clearly identify a center position of the colon lumen in image data, the input data determination module 801 may determine whether the location based on the feature extraction approach should be used, or the estimated location based on the motion vector approach should be used, or some combination of both should be used. Determination of a loss of, or change in, sensor input data integrity may comprise evaluating a variety of factors that impact the quality of the sensor data. For instance, sensor data may be determined to have lost integrity when the signal-to-noise ratio falls below a specified threshold. Once the integrity of the input sensor data has been evaluated, the input data determination module 801 may determine which data are included in the set input data fed to the ANN.

Figure 9:
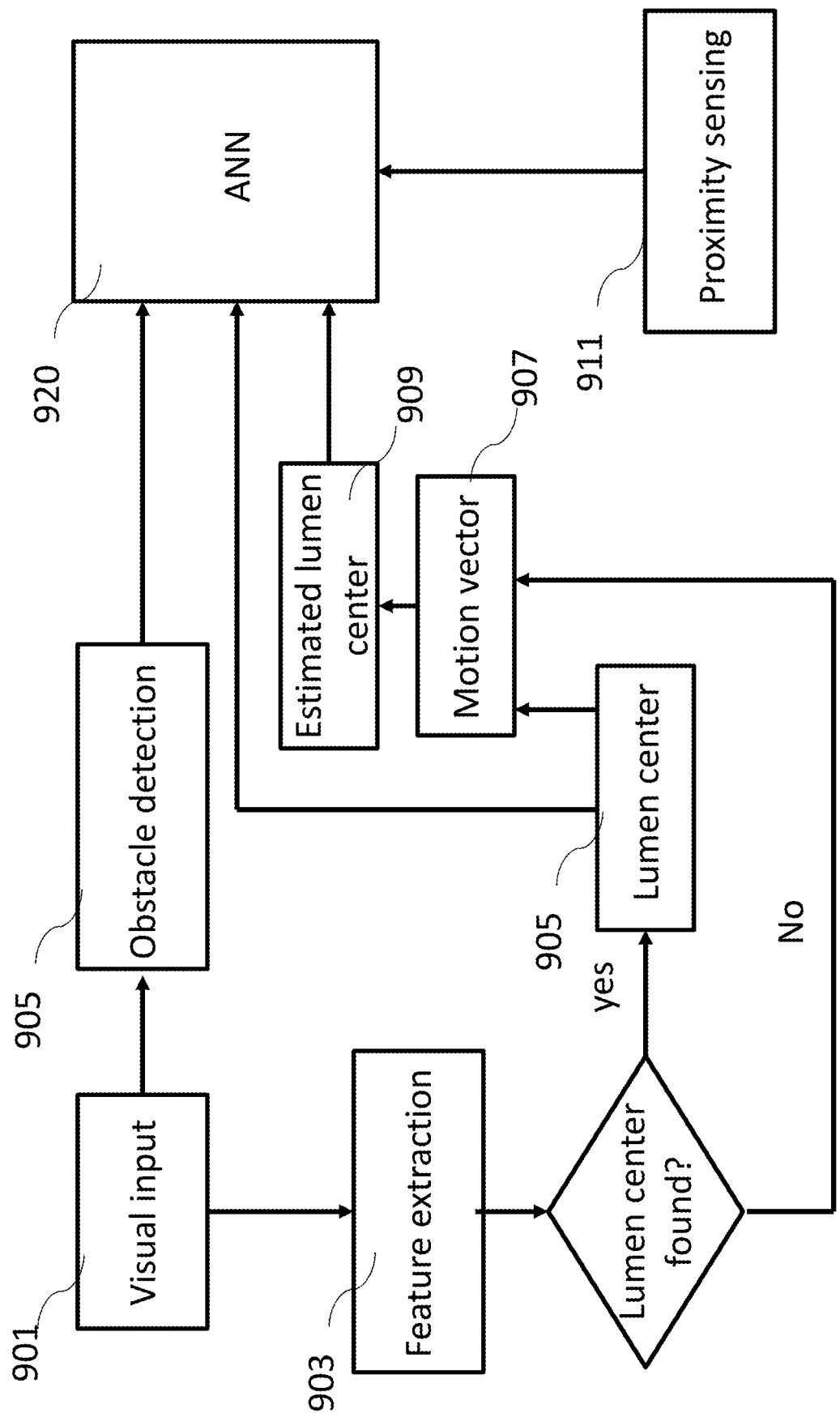
FIG. 9 provides a flowchart that illustrates how the input data that are fed to a neural network are evaluated and modified according to a change in data integrity that impacts the determination of a center position for the lumen through which a robotic endoscope is advancing.

FIG. 9 illustrates a flow chart of how the set of input data sent to the ANN are selected based on changes in the integrity of image sensor data. As illustrated in FIG. 9, upon receiving a vision input such as an image frame 901, the image data may be analyzed to identify the lumen center 903. In some cases, the same image data may also be used for detecting obstacles 905 using the light reflection method as described elsewhere herein. The obstacles detected using the light reflection information may be obstacles within a field of view of the camera. The location of the detected obstacle and/or distance to the obstacle may be supplied as input data to the neural network of the adaptive steering control system 920. If a lumen center is recognized or extracted from the image data, the location of the lumen center may be determined 905 and may be used as the input data for the neural network. The location of the lumen center may also be recorded and used for updating the motion vector 907. The motion vector may or may not be included in the input data supplied to the neural network. If a lumen center is not detected in the image data, the motion vector may be used to estimate location of the lumen center 909 and the estimated lumen center location is included in the input data supplied to the neural network. In some embodiments, the location of the lumen center may be determined based on either the image feature extracted lumen center or the estimated lumen center. In some embodiments, the location of the lumen center may be determined based on a combination of both methods. When the position of the lumen center is identified by image feature extraction, it may be used in conjunction with the motion vector-based estimate of the location of the lumen center to determine a confirmed location of the lumen center. Various methods can be used for fusing the data from the two methods, such as a weighted sum approach or use of a Kalman-filter. Proximity sensing data 911 that is indicative of obstacles or the position of the distal end of the colonoscope relative to the colon wall or lumen center may also be included in the input data supplied to the neural network. In some instances, e.g., when image processing fails to identify the position of the lumen center by either the feature extraction or motion vector methods, the ANN may rely on proximity sensor data alone for predicting a target direction and/or generating a steering control signal.

Processors, Computer Systems, and Distributed Computing Environments:

One or more steering control processors may be used to implement the machine learning training methods or machine learning-based steering control systems of the present disclosure. The processor may be a hardware processor such as a central processing unit (CPU), a graphic processing unit (GPU), a general-purpose processing unit, or computing platform. The processor may be comprised of any of a variety of suitable integrated circuits, microprocessors, logic devices and the like. Although the disclosure is described with reference to a processor, other types of integrated circuits and logic devices are also applicable. The processor may have any suitable data operation capability. For example, the processor may perform 512 bit, 256 bit, 128 bit, 64 bit, 32 bit, or 16 bit data operations.

The processor may be a processing unit of a computer system. The processors or the computer system used for training the machine learning algorithm may or may not be the same processors or system used for implementing the steering control system. The computer system may enable a cloud computing approach. The computer system may allow training datasets to be shared and updated by one or more computer systems or across one or more machine learning-based robotic colonoscopy systems.

The computer system can be operatively coupled to a computer network ("network") with the aid of a communication interface. The network can be the Internet, an intranet and/or extranet, an intranet and/or extranet that is in communication with the Internet, or a local area network. The network in some cases is a telecommunication and/or data network. The network can include one or more computer servers, which can enable distributed computing, such as cloud computing. In some instances, the machine learning architecture is linked to, and makes use of, data and stored parameters that are stored in cloud-based database. The network, in some cases with the aid of the computer system, can implement a peer-to-peer network, which may enable devices coupled to the computer system to behave as a client or a server.

The computer system can comprise a mobile phone, a tablet, a wearable device, a laptop computer, a desktop computer, a central server, etc. The computer system includes a central processing unit (CPU, also "processor" and "computer processor" herein), which can be a single core or multi core processor, or a plurality of processors for parallel processing. The CPU can be the processor as described above.

The computer system also includes memory or memory locations (e.g., random-access memory, read-only memory, flash memory), electronic storage units (e.g., hard disk), communication interfaces (e.g., network adapter) for communicating with one or more other systems, and peripheral devices, such as cache, other memory, data storage and/or electronic display adapters. In some cases, the communication interface may allow the computer to be in communication with another device such as the colonoscope. The computer may be able to receive input data from the coupled devices such as the colonoscope for analysis. The memory, storage unit, interface and peripheral devices are in communication with the CPU through a communication bus (solid lines), such as a motherboard. The storage unit can be a data storage unit (or data repository) for storing data.

The CPU can execute a sequence of machine-readable instructions, which can be embodied in a program or software. The instructions may be stored in a memory location. The instructions can be directed to the CPU, which can subsequently program or otherwise configure the CPU to implement methods of the present disclosure. Examples of operations performed by the CPU can include fetch, decode, execute, and write back.

The CPU can be part of a circuit, such as an integrated circuit. One or more other components of the system can be included in the circuit. In some cases, the circuit is an application specific integrated circuit (ASIC).

The storage unit can store files, such as drivers, libraries and saved programs. The storage unit can store one or more training datasets and/or trained parameters of the neural network. The storage unit can store user data, e.g., user preferences and user programs. The computer system in some cases can include one or more additional data storage units that are external to the computer system, such as located on a remote server that is in communication with the computer system through an intranet or the Internet.

The computer system can communicate with one or more remote computer systems through the network. For instance, the computer system can communicate with a remote computer system of a user. Examples of remote computer systems include personal computers, slate or tablet PC's, smart phones, personal digital assistants, and so on. The user can access the computer system via the network.

Methods as described herein can be implemented by way of machine (e.g., computer processor) executable code stored on an electronic storage location of the computer system, such as, for example, on the memory or electronic storage unit. The machine executable or machine readable code can be provided in the form of software. During use, the code can be executed by the processor. In some cases, the code can be retrieved from the storage unit and stored on the memory for ready access by the processor. In some situations, the electronic storage unit can be precluded, and machine-executable instructions are stored on memory.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system, can be embodied in software. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system can include or be in communication with an electronic display for providing, for example, images captured by the imaging device. The display may also be capable to provide a user interface. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit.

Adaptive Steering Control System for a Robotic Endoscope:

The trained machine learning architecture, e.g. an artificial neural network, described above may be used in an automated, adaptive steering control system for controlling the movement of the distal end of a robotic endoscope, e.g., a robotic colonoscope, in real-time. The system may comprise: one or more image sensors configured to capture one or more images of a colon lumen; and one or more processors that are individually or collectively configured to (i) perform automated feature extraction on the one or more images to determine a center position of the colon lumen, (ii) perform automated image processing on the one or more images to identify a location of a colon lumen wall or other obstacle that is in close proximity to an distal end of the robotic colonoscope based on areas of high light reflection, and (iii) determine a navigation direction that directs the robotic colonoscope towards the center position of the colon lumen using a machine learning—based analysis of the center positions and locations determined in steps (i) and (ii), wherein the machine learning-based analysis provides a steering control output signal that adapts to loss of or changes in the integrity of center position or location data.

Figure 10A:
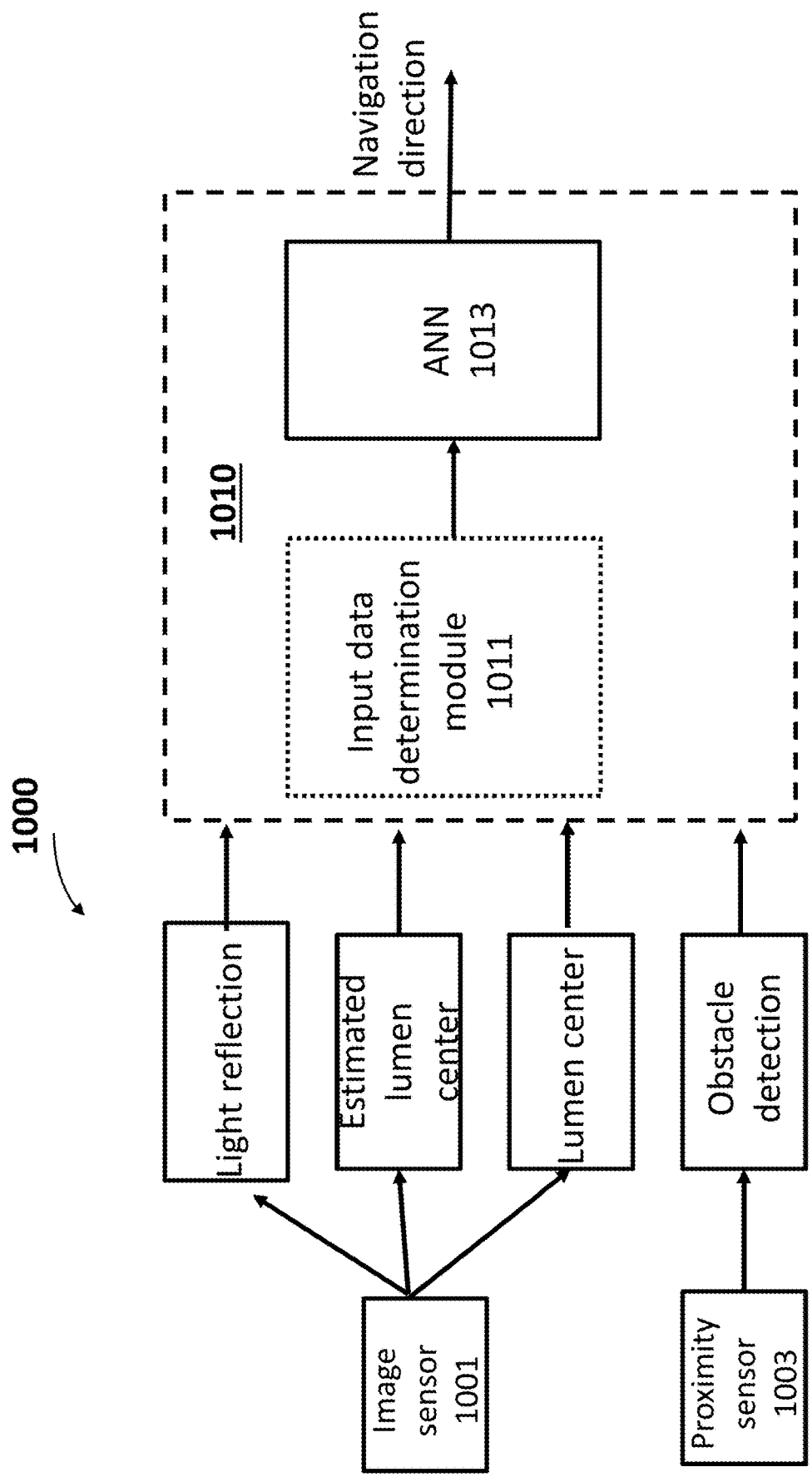
FIG. 10A and FIG. 10B show block diagrams of exemplary adaptive steering control systems for a robotic endoscope.

FIG. 10A shows a block diagram of an adaptive steering control system 1000. The steering control system may be the same as the system as described in FIG. 2. The control system as shown in FIG. 10A may comprise one or more image sensors 1001. The image sensors may be configured to collect image data as described elsewhere herein. The image data and information derived from the image data may be input to a steering control module 1010 for generating a control signal or navigation direction in real-time. The steering control module can be the same as the steering control module as described in FIG. 2. The steering control module 1010 may be configured to generate the control signal or navigation direction using a machine learning method such as artificial neural network 1013. In some cases, the image data may be processed to extract information. For example, a lumen center may be detected in the image data and the location of the lumen center may be determined and used as input data to the steering control module. In another example, an intensity gradient map derived from the image data, or areas of the image exhibit high light reflection may be analyzed for detection of an obstacle as described elsewhere herein. The image data may be acquired and processed at a rate of at least 10 HZ, 20 HZ, 30 HZ, 40 HZ, 50 HZ, 60 HZ, 70 HZ, or 80 HZ. Image data or information derived from image data may be included in the input data set supplied to the steering control module. In some cases, examples of the types of information derived from image data may include, but are not limited to, location of the lumen center, estimated location of the lumen center, a calculated motion vector, an intensity gradient map, the locations of obstacles detected by analysis of light reflection, and the like.

In some embodiments, in addition to the image data, proximity sensor data 1003 may also be collected and supplied to the steering control module. The proximity sensor data may comprise information indicative of the distance to an obstacle or the position of a guiding portion of the colonoscope (e.g., the distal end) relative to its environment.

In some cases, sensor data derived from the different sensors may be collected at the same time point. Alternatively, sensor data derived from different sensors may not be collected at the same time point. Different types of sensor data may or may not be obtained at the same frequency. In some cases, when different types of sensor data are not collected at the same time point or the same acquisition rate, time stamps may be used to register the different types of data. The image sensor data may be obtained at an image acquisition rate of at least, 5 HZ, 10 HZ, 20 HZ, 30 HZ, 40 HZ, 50 HZ, 60 HZ, 70 HZ, or 80 HZ. The touch or proximity sensor data may be obtained at a data acquisition rate of at least, 5 HZ, 10 HZ, 20 HZ, 40 HZ, 60 HZ, 80 HZ, 100 HZ, 200 HZ, 400 HZ, 600 HZ, 800 HZ, or 1000 HZ that may or may not be the same as the rate at which image sensor data is acquired and processed.

In some embodiments, the image data may be analyzed to determine whether or not a loss of or change in the integrity of the image data has occurred. For example, a loss of or change in the integrity of the image data may comprise a failure of the automated image feature extraction step to unambiguously identify a center position of the colon lumen, or the failure of the automated image processing step to identify an obstacle. A loss of or change in the integrity of input sensor data may be determined by an input data determination module 1011 as described elsewhere herein. The input data determination module may be configured to determine and adjust which selection of raw or pre-processed input data is sent to the machine learning algorithm based on the loss or change in integrity of one or more input data streams. For example, the input data determination module 1011 may determine whether the location of lumen center determined using the feature extraction method is used, or the estimated location of the lumen center based on the motion vector method is used, or a combination of both is used. In some cases, e.g., when a loss of image sensor data integrity is identified, the estimated location of lumen center may be included in the input data set along with proximity sensor data and/or data related to obstacles detected using the light reflection method. In some cases, when a loss of image sensor data integrity is identified, only the proximity sensor data may be included in the input data set used for determining the output target navigation direction or steering control signal. In some cases, the input data supplied to the neural network may comprise the original (raw) image data rather than the pre-process determination of the location of lumen center.

The artificial neural network 1013 may be pre-trained using the methods described above. Various parameters, e.g., weights, biases, and activation thresholds, may be learned during the training phase, and subsequently may be loaded to a memory unit accessible to the steering control module. In some instances, the sensor input data and steering control output directions or signals from each new instance of performing an endoscopic procedure (e.g., a colonoscopy) are used to update the training dataset(s) used by that specific colonoscope or by a plurality of colonoscopes that communicate via a distributed computing system. The output of the artificial neural network may comprise a control signal to an actuation unit of the colonoscope or a target navigation direction. The target navigation direction may or may not be aligned with the location of lumen center.

Figure 10B:
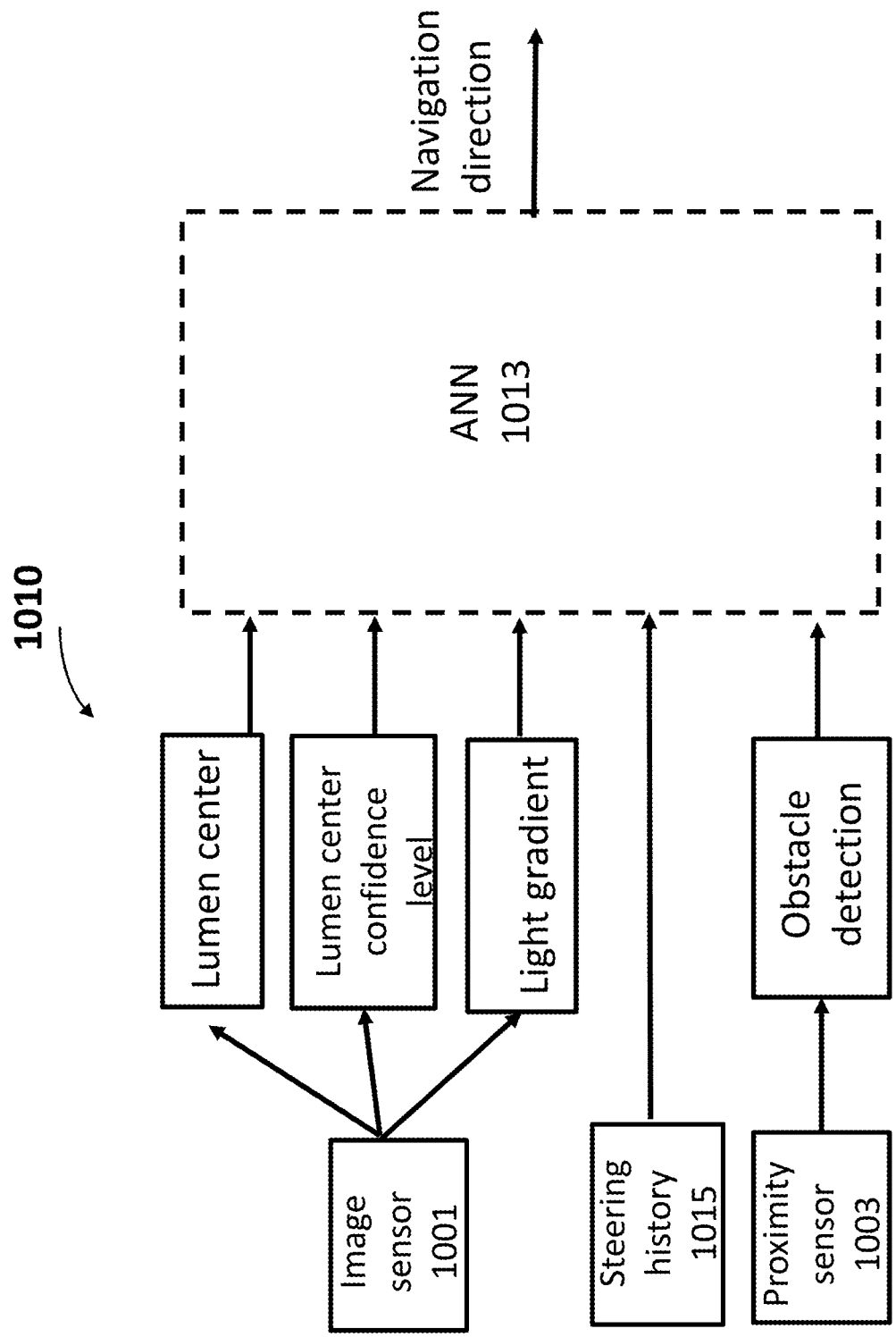

FIG. 10B shows another example of a steering control system 1010. The steering control system 1010 may be similar to the control system 1000 as described above except that the input data may be different. In the illustrated example, the input data for generating a steering control signal may comprise a determination of a lumen center location, a confidence level in the determination of lumen center, and light intensity gradient data derived from image sensor data 1001, steering history data 1015, and proximity sensor data 1003. The artificial neural network 1013 may be pre-trained in a process as described in FIG. 8C. In some cases, the steering control system 1010 may not comprise an input data determination module. All of the input data may be processed by the artificial neural network to generate a control signal. In some cases, when a lumen center is not perceivable in the image frame, the system may be configured to perform an automatic route search to obtain an image with the lumen center within the view. Details regarding automatic route search are discussed later herein.

Figure 11:
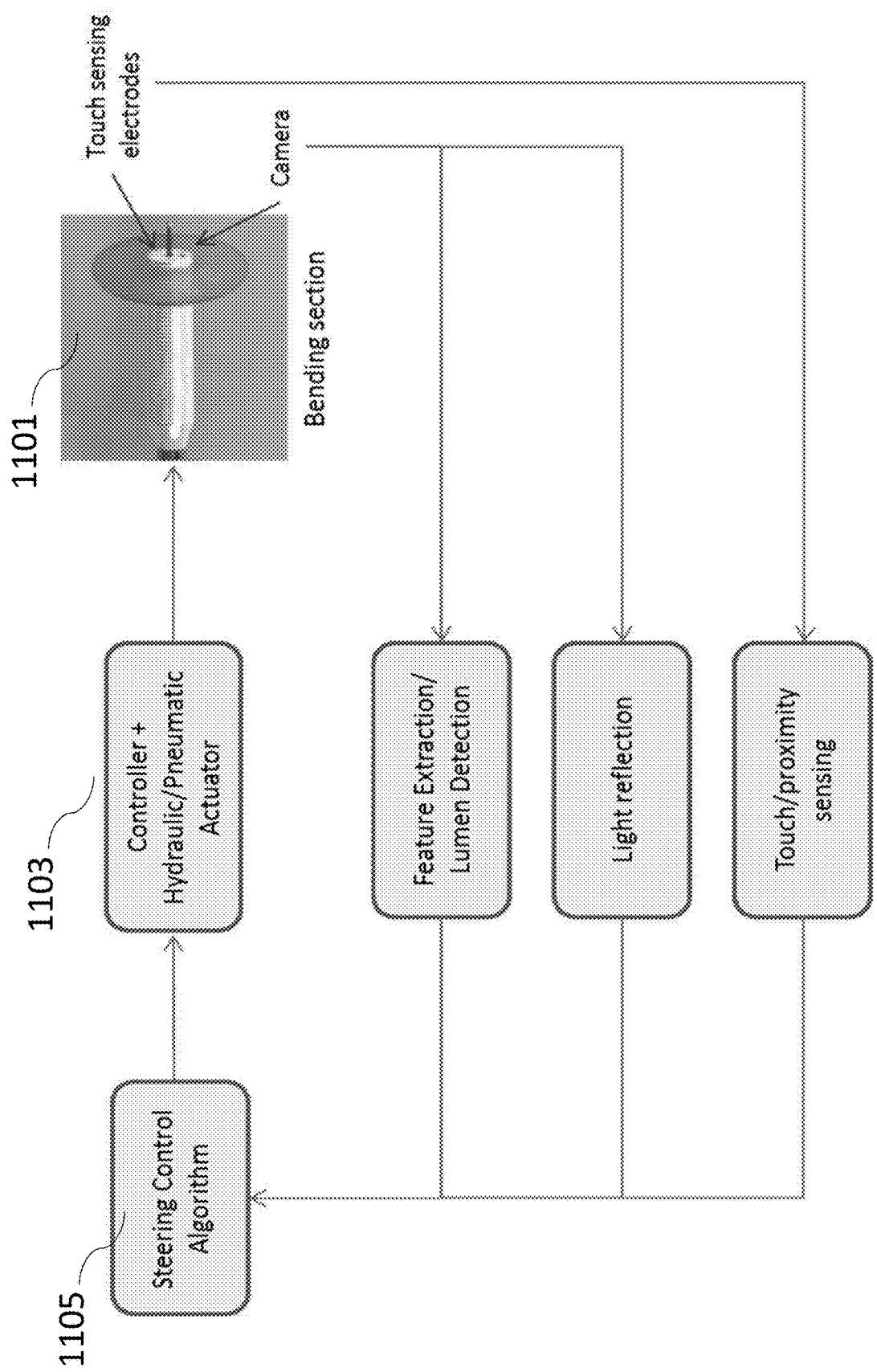
FIG. 11 illustrates an example of using the provided automated steering control method for controlling the steering direction of a robotic endoscope system.

Example—A Soft Robotic Endoscope Comprising an Automated Steering Control System FIG. 11 provides a block diagram illustrating a robotic colonoscope that comprises the automated steering control system of the present disclosure. As illustrated in the figure, the robotic colonoscope system comprises a guiding portion 1101 (i.e., a steerable bending section) where a plurality of sensors may be affixed. In this particular example, the plurality of sensors comprises an imaging sensor (e.g., a camera) and a touch (or proximity) sensor. The movement of the steerable bending section is controlled by an actuation unit 1103. In this example, the degrees of motion that are controlled by the actuation unit include at least rotational motion about a pitch axis and a yaw axis. In some embodiments, the degrees of motion controlled by the actuation unit may also include, for example, rotation about a roll axis or translational movement (e.g., forward or backward). In some cases, the actuation unit may also comprise a controller configured to receive control instructions or a target navigation direction generated by the steering control system, and generate control signals to one or more actuators in the actuation unit. Alternatively, the actuation unit may receive control signals directly from the steering control system. The steering control system includes a processor that is programmed to employ a steering control algorithm 1105, as described previously. The steering control algorithm may be, for example, a deep learning method (e.g., an ANN or CNN algorithm).

The steering control system (and methods disclosed herein) may be used in various ways in conjunction with the soft robotic colonoscopy system. For example, the steering control system may provide feedback control of steering direction for the bending section of the colonoscope. The steering control system receives input sensor data collected by the plurality of sensors, i.e., the camera and touch sensor in this example, and outputs a target direction or a control signal to the actuation unit. In some instances, the steering control system may provide open loop control or predictive control. Image data from the camera is processed using a feature extraction algorithm and/or motion vector method as described previously to identify a center position of the colon lumen, and is also processed using the light reflection method described previously to identify regions of the lumen wall and/or obstacles that are in close proximity to the distal end of the colonoscope, and is subsequently passed to the steering control algorithm. Touch sensor data is fed to the steering control algorithm in parallel with the image sensor data, and is used to complement the image-based analysis and/or to substitute for image-based analysis in instances where the image processing algorithms fail to identify the position of the lumen center, when the image sensor malfunctions, or when the quality of the image sensor data fails to meet a defined threshold, e.g., a defined signal-to-noise ratio. The steering control algorithm processes the sensor input data base on previous learning from one or more training data sets, and outputs a target steering direction and/or steering control signal to the actuation unit.

Examples of the features and benefits of the robotic colonoscope illustrated schematically in FIG. 11 include: (i) a miniaturized and disposable soft colonoscope designed to ensure non-invasive, reliable, pain-free and safe colorectal screening and endoluminal surgical procedures; (ii) an automated, robotic-driven self-steering mechanism that maintains precise device positioning relative to the colonic lumen center; and (iii) a pneumatic/hydraulic-driven soft elastomeric active bending mechanism that allows omni-directional steering of the device towards areas of interest to perform diagnostic and therapeutic procedures.

Example—Graphical User Interface for Steering Control Systems

Figure 12:
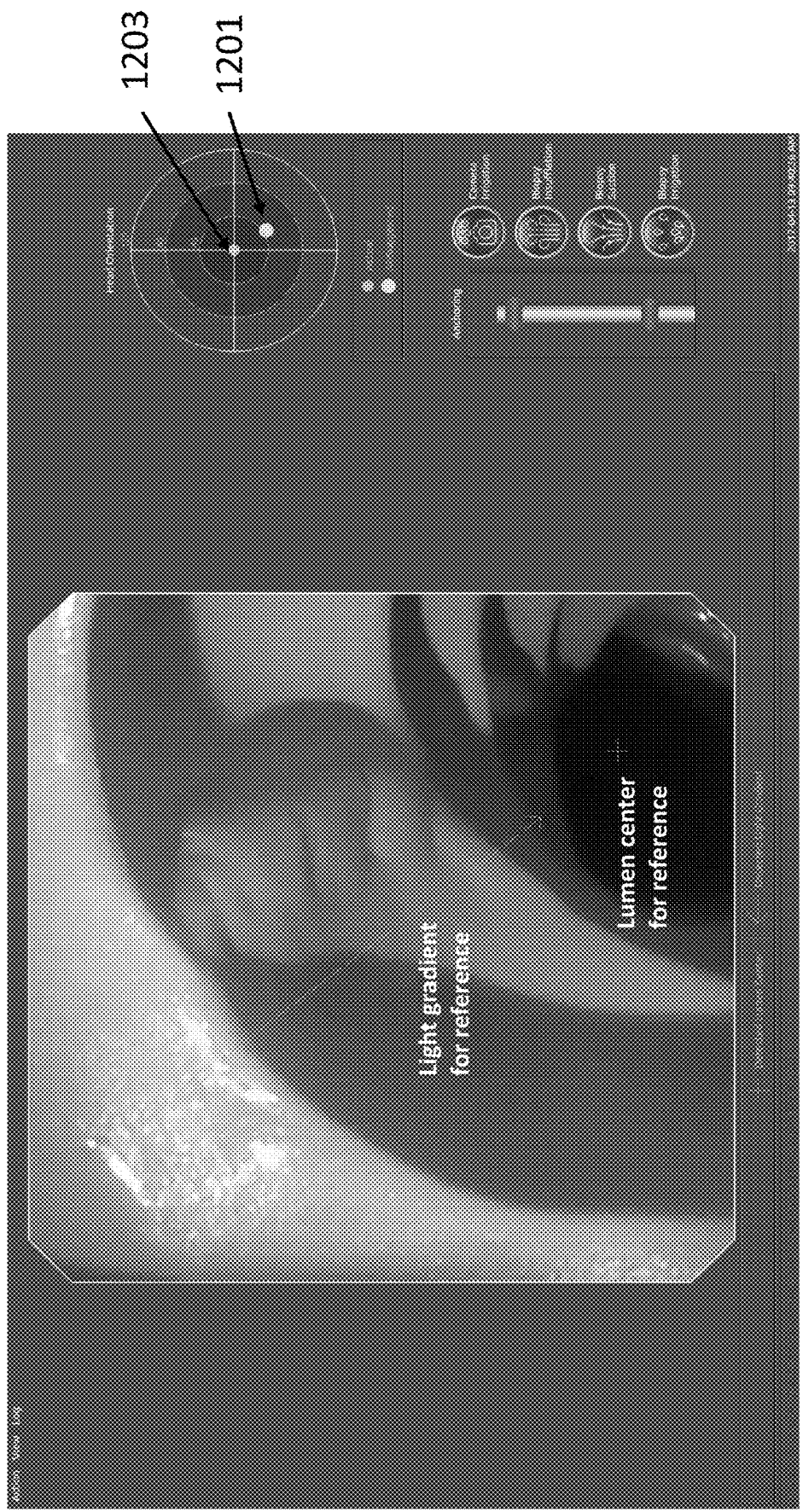
FIG. 12 shows an exemplary screen shot of user interface software for implementing the artificial neural network-based steering control system of the present disclosure.

In many embodiments, the endoscope steering control systems of the present disclosure may comprise additional software components, e.g., software for providing a user interface. FIG. 12 shows an exemplary software user interface, e.g., a graphical user interface, for implementing the artificial neural network based steering control methods of the present disclosure. The software may be used to implement a trained ANN-based steering control system (i.e., during training of the system and/or during the performance of endoscopic procedures) and display real-time sensor data and/or steering control information to a user. Real-time sensor data such as image frames or video streams may be displayed. In some embodiments, images with augmented information may be provided. Augmented information such as light intensity gradient data, detected lumen center positions, etc., may be overlaid onto the real-time image frames.

The steering control system for the endoscope, e.g., a colonoscope, may be a fully-automated control system, semi-automated control system, or a user-supervised control system. In some cases, a user may be allowed to manually control the steering of the colonoscope while assisted by steering direction data provided by an ANN. For example, an actual steering direction 1203 and an ANN-generated proposed steering direction 1201 may be displayed on the user interface simultaneously, thereby allowing the user to make adjustments to the steering direction. In some cases, the steering control system may be a fully automated control system that does not require a user to provide steering instructions during the process.

Prophetic Example—Steering Control with Auto-Tracking

The disclosed systems and methods can be used for automated steering control of robotic endoscopes, e.g., robotic colonoscopes, and for various related applications. For instance, the control system may be used for tracking an object of interest. The object of interest may be any object in a lumen such as a polyp, a lesion, an adenoma, or other cancerous growth. The provided control system may allow the distal end of the colonoscope to maintain a fixed position relative to the object of interest which may be beneficial for performing surgical procedures or high resolution imaging. For instance, orientation of the distal end of the colonoscope may be automatically controlled by the provided system such that the location of the object of interest in the field-of-view remains relatively steady as the colonoscope is advanced. The provided control system may also allow the object of interest to be maintained in a substantially stationary location within the field-of-view by the surgeon while reducing contact between the colonoscope and the lumen wall.

In some embodiments, the control system configured to provide this auto-tracking capability may comprise: a) a first image sensor configured to provide a first image data stream, and the first image data stream comprises data relating to a position of the object of interest within a field-of-view of the first image sensor; and b) a processor that is configured to generate a steering control output signal based on an analysis of the first image data stream using a machine learning architecture such that the object of interest has a substantially fixed position relative to the field-of-view of the first image sensor, and the steering control output signal adapts to changes in the data of the first image data stream in real time. The control system may be the same as the steering control system described elsewhere herein.

In some embodiments, a steering control signal is adjusted so that the position of the object of interest within the field-of-view varies from one image frame to the next by less than 10 pixels, less than 100 pixels, less than 500 pixels, less than 1000 pixels, or less than 2000 pixels.

In some embodiments, the input data supplied to the ANN based control system may comprise a location of the object of interest, a confidence level in the determination of the object location, light intensity gradient data, steering history data, and/or proximity sensor data. The location of an object of interest can be determined using the same image processing methods as described for identifying the location of a lumen center. The confidence level for determination of the object location may be determined based on one or more factors such as light intensity data, calculations of the moment of inertia or convexity of the image of the object of interest, etc., as described elsewhere herein.

The orientation or steering direction of the colonoscope may be controlled such that the object of interest may be perceived in a stationary location within the field-of-view. The location may be the center of the field-of-view or any other location within the field-of-view. In some cases, the location may be determined by a user. Alternatively, the location can be determined automatically according to the specific operations or purposes.

Figure 13:
FIG. 13 shows an exemplary field-of-view image comprising an object of interest and a tool for performing a surgical operation.

FIG. 13 shows an exemplary field-of-view comprising an object of interested 1301 and a tool for surgical operations. The object of interest may be detected or recognized using methods such as automated image feature extraction as described elsewhere herein. The distal end of the colonoscope, where the camera is attached, may be controlled by the provided control system such that the object 1301 maintains a stationary location within the field-of-view. In some cases, augmented information such as a contour of the detected object of interest may be overlaid onto the real-time images. The control system may be configured to compensate for undesired movements such as shaking and automatically track the object of interest as the colonoscope is advanced or during the surgical procedure such that the surgeon is not distracted by the unwanted movements.

Prophetic Example—Steering Control with Auto-Route Searching

Figure 14:
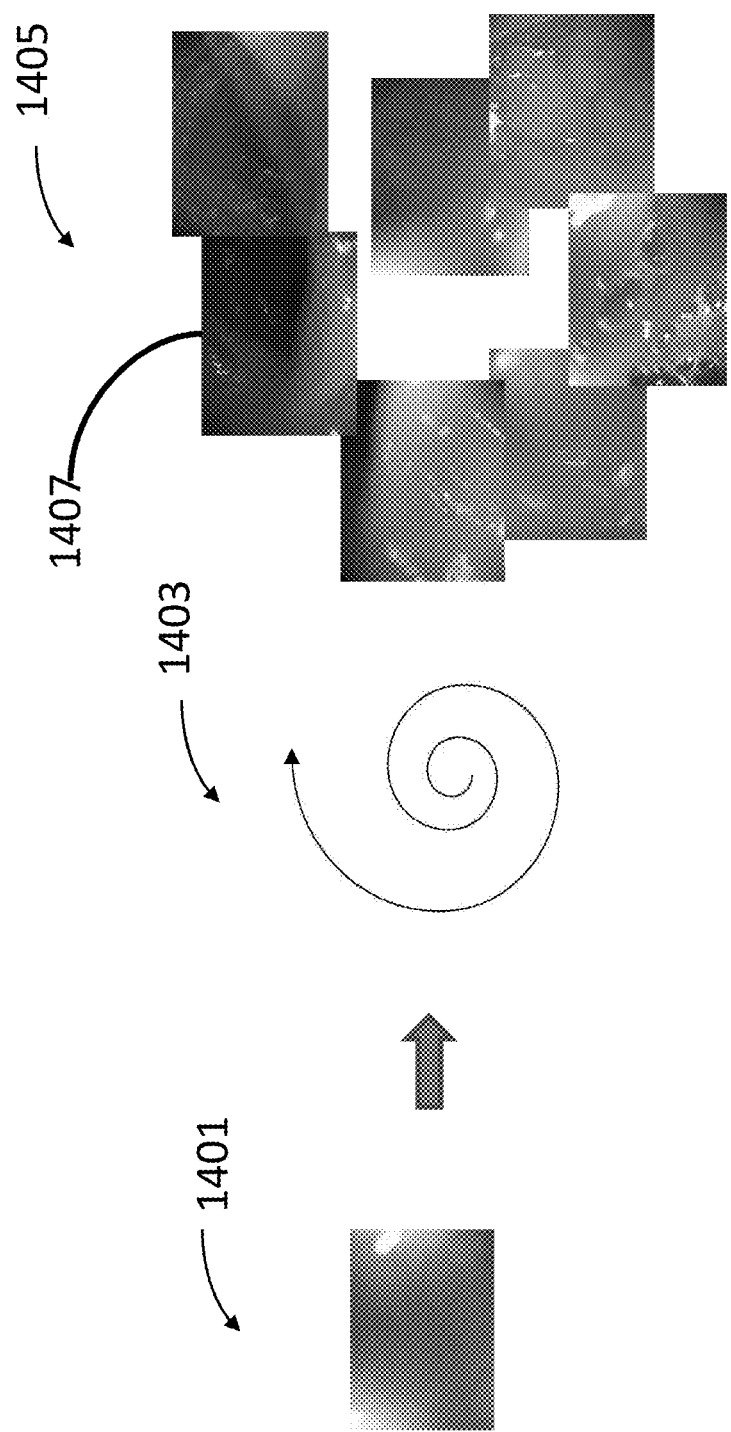
FIG. 14 shows an example of a method for performing an auto route search.

In some embodiments, e.g., when an object of interest or lumen center is not perceivable in the field-of-view, the control system may be configured to perform an automated route searching procedure prior to generating a steering control signal. This step may be performed prior to an ANN operation for generating a control signal. FIG. 14 shows an example of performing an auto route search. An image 1401 may be processed to generate a confidence level for detection of the lumen center or an object of interest. The confidence level may be calculated using the methods as described above. The confidence level may be compared against a threshold value to determine whether to perform an auto route searching procedure. For instance, when the confidence level falls below the threshold, indicating a lumen center or object of interest may not be well perceived in the image frame, an automated route search may be performed. The distal end of the colonoscope may be steered to follow a specified route searching pattern while the image sensor acquires a series of images for use in identifying an image in which the lumen center or object of interest can be identified. The specified route 1403 may comprise two-dimensional search patterns or three-dimensional search patterns. The specified route may comprise any pattern of any dimension, scale or shape such as a spiral pattern, a rectilinear grid pattern, or a circular pattern. The route may be selected or specified by a user. The route may be automatically selected by a machine learning method, for example. In some cases, the route may be automatically selected based on processing of the real-time image data stream. For instance, based on the information obtained from the image data such as the confidence level for identification of the lumen center or an object of interest, or light intensity gradient data, a route searching pattern of a specified direction, scale, or shape may be automatically generated.

One or more images 1405 may be captured during the route searching procedure. In some embodiments, confidence level may be calculated for each image and compared to the threshold. In some cases, the route searching process may be stopped when an image with a confidence level at or above the threshold is obtained. In some cases, two or more of the captured images may have a confidence level above the threshold, and the image with the highest confidence level may be used as input data by the machine learning algorithm for generating a steering control signal.

Prophetic Example—Steering Control with 3D Mapping

In some embodiments, the provided systems and methods may be used for constructing a three-dimensional map of the center position of a lumen. The three-dimensional map of the lumen may be provided on a graphical user interface to assist a surgeon during a surgical process. The three-dimensional map may provide accurate spatial information such as coordinates that identify the location of a feature of interest that is detected in the image data stream. The method may comprise: a) providing a first image data stream, wherein the first image data stream comprises image data relating to a position of a distal end of the robotic endoscope relative to the center of the lumen, relative to a wall of the lumen, relative to an obstacle, or any combination thereof; b) generating a steering control output signal based on an analysis of the first image data stream using a machine learning architecture to identify a steering direction for movement towards the center of the lumen, wherein the steering control output signal adapts to changes in the data of the first image data stream in real time; c) storing a sequence of data pairs in a computer memory device, wherein each data pair comprises a steering direction and a translational displacement of the robotic endoscope; and d) using a processor and the stored values of steering direction and translational displacement to create a three-dimensional map of the position of the center of the lumen.

In some embodiments, the provided systems and methods may be used for reconstructing a three-dimensional image map of the interior of a lumen. The three-dimensional map may be constructed based on the image data stream provided by imaging sensors attached to the distal end of a robotic endoscope. The robotic endoscope may be controlled using the steering control system provided herein. The method for reconstructing a three-dimensional image map of the interior of a lumen using a robotic endoscope equipped with an adaptive steering control system may comprise: a) providing a first image data stream, wherein the first image data stream comprises image data relating to a position of a distal end of the robotic endoscope relative to the center of the lumen, relative to a wall of the lumen, relative to an obstacle, or any combination thereof; b) generating a steering control output signal based on an analysis of the first image data stream using a machine learning architecture to identify a steering direction for movement towards the center of the lumen, wherein the steering control output signal adapts to changes in the data of the first image data stream in real time; c) storing the image data from the first image data stream, and values of steering direction and translational movement of the robotic endoscope, in a computer memory device; d) using the stored values of steering direction and translational movement to create a three-dimensional map of the position of the center of the lumen; and e) overlaying the stored image data with the three-dimensional map of the position of the center of the lumen to reconstruct a three-dimensional image map of the lumen interior.

The three-dimensional image map may comprise image data and augmented information overlaid onto the image data. The augmented information may comprise steering vector data for the robotic endoscope, an image of the robotic endoscope, the position (or center line) of the lumen center, and various other pieces of information. In some cases, the image of the robotic endoscope in the three-dimensional view is constructed based on a pre-stored computer-aided design model of the robotic endoscope. In some cases, the image of the robotic endoscope in the three-dimensional view is constructed based on real-time sensor data. For instance, sensor data provided by one or more sensors located in or along the main body of the robotic endoscope may be utilized to provide proximity or location data for the main body of the robotic endoscope relative to the center or interior of the lumen. Various sensors may be used to provide such locational or positional information such as photosensors, optical image sensors, additional touch/proximity sensors, motion sensors, or location sensors as described elsewhere herein. In some cases, a combination of sensor data and design specifications for the robotic endoscope (e.g., geometric model or kinematics model) of the robotic endoscope may be used to provide a real-time configuration of the robotic endoscope relative to the lumen. The three-dimensional image map of the lumen walls may be displayed to a user on a display screen or via any other suitable devices. For instance, a viewing device such as a wearable augmented reality device may be provided. The three-dimensional image map may be a first person view or a perspective view of a reconstructed lumen interior and the robotic endoscope.

Example—Steering Control Method Using Machine Learning-Based Analysis of Processed Image Data As noted above, in some embodiments the input data utilized by the disclosed steering control methods and systems for guiding a robotic endoscope may be comprised solely of image data generated by one or more image sensors, e.g., a series of one or more time-stamped individual images or a series of one or more video images derived from a video camera. In some instances, as in the present example, the raw image data may be pre-processed using an image processing algorithm (or a combination of two or more image processing algorithms) to, for example, identify the location of the lumen center, estimate the direction in which the lumen center lies (if not visible in the image), calculate a confidence level of having correctly determined the location of or direction towards the lumen center, etc. Any combination of these image processing-derived parameters, as well as other information derived from processing of the image data, e.g., light intensity gradient vectors, motion vectors, etc., may be used as input for a machine learning algorithm that maps the input data to output values comprising a navigation direction and/or set of steering control instructions.

Figure 15:
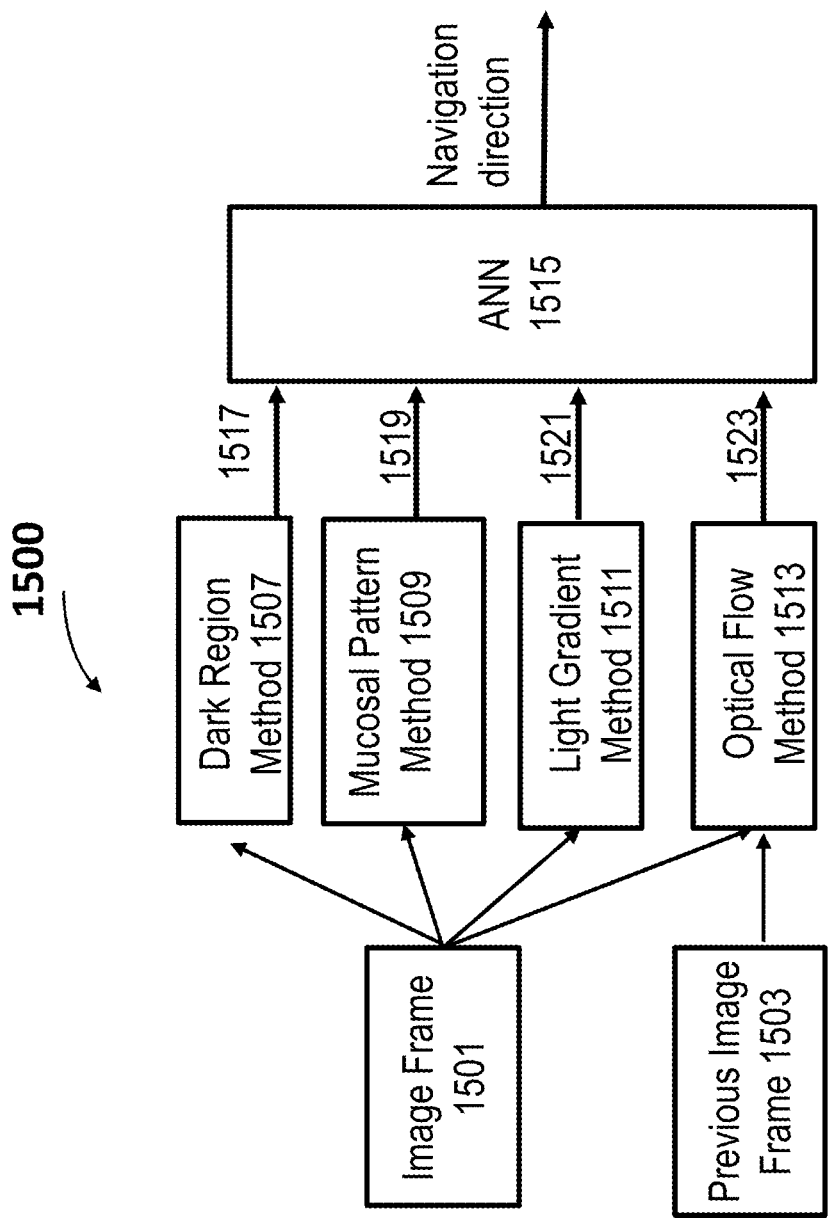
FIG. 15 shows a block diagram of an exemplary adaptive steering control system for a robotic endoscope that uses data collected by image sensors to generate a steering control signal, where the image data is processed using two or more image processing algorithms and subsequently used as input for an artificial neural network (ANN) that maps the input data to a navigation direction.

FIG. 15 shows a non-limiting example of a block diagram for steering control system 1500 that uses data collected by one or more image sensors. The steering control system 1500 may be configured to generate a steering control signal or navigation direction using a machine learning method such as an artificial neural network 1515. The input data for the ANN may be generated from one or more image frames using a plurality of image processing methods. In some cases, the image frame data may also comprise previous or historical image frames. Examples of suitable image processing methods that may be utilized include, but are not limited to, a dark region detection method 1507 (to generate output data 1517), a mucosal pattern method 1509 (to generate output data 1519), a light gradient method 1511 (to generate output data 1521), and an optical flow method 1513 (to generate output data 1523). It should be noted that various other image processing methods known to those of skill in the art may also be used to determine, e.g., the lumen center location, an estimate of the direction towards the lumen center, and/or a confidence level. Any combination of data 1517, 1519, 1521, and/or 1523 may be used as input to be analyzed by the artificial neural network 1515. The location of the lumen center, a confidence level calculation, a motion vector, or a light intensity gradient vector, or any combination thereof, as determined for a series of one or more images may be processed by the artificial neural network 1515 to determine a navigation direction and/or generate a set of one or more steering control signals. The artificial neural network 1515 may comprise any of a variety of neural network algorithms known to those of skill in the art. The ANN may be trained using a process such as that illustrated in FIGS. 8A-8C. The one or more training data sets utilized may comprise image data collected by an image sensor and/or simulated image data that is paired with desired output steering control data.

Figure 16:
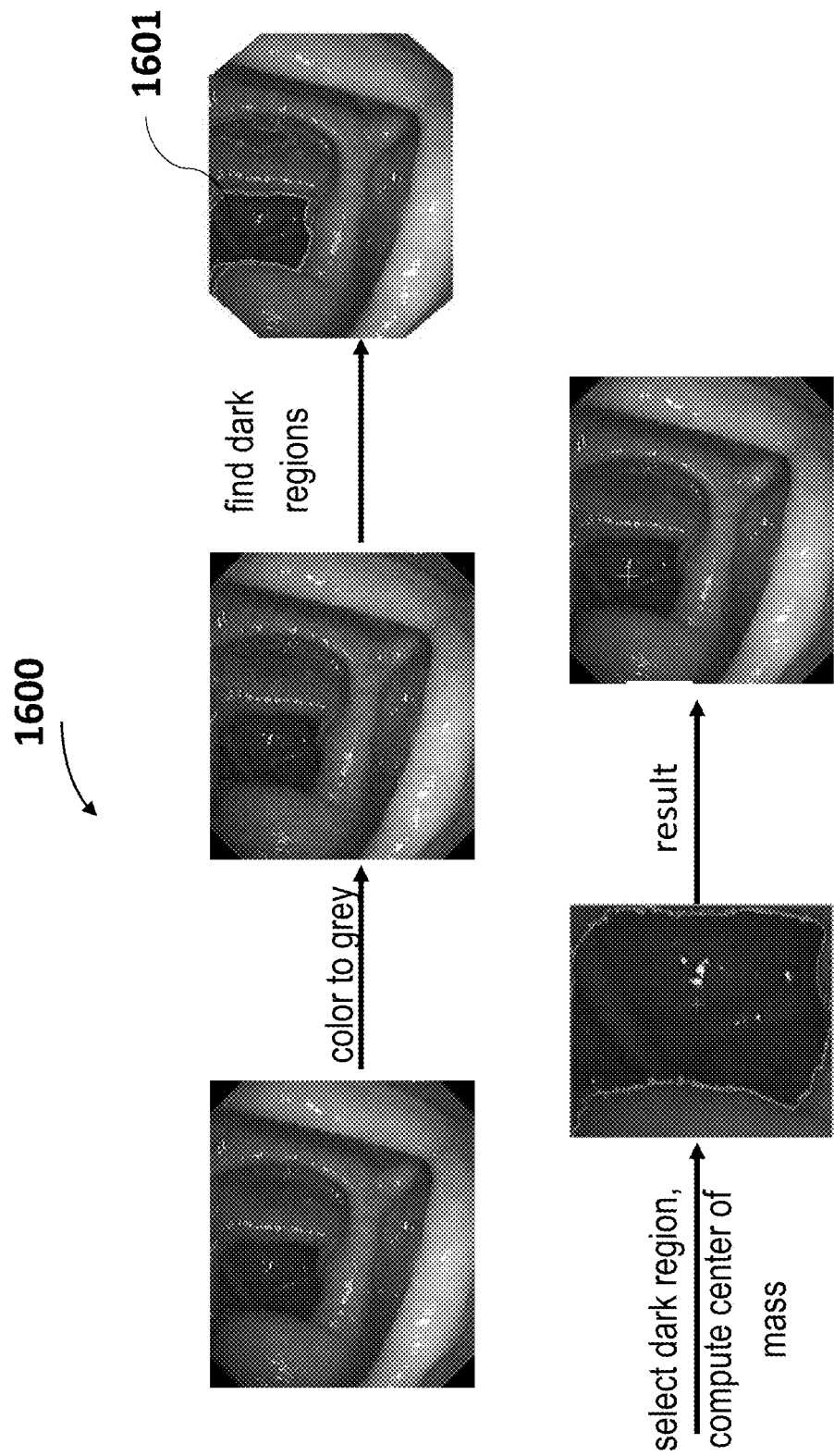
FIG. 16 illustrates the steps of an image processing method used to identify dark regions within an image of, for example, a colon lumen that may be candidates for the position of the center of the colon lumen.

FIG. 16 illustrates the steps of an exemplary image processing method (i.e., a dark region detection method 1507) used to identify dark region(s) within an image of, for example, a colon lumen that may be candidates for the position of the center of the colon lumen. In some cases, the captured raw image frame may be a color image (e.g., an RGB image), in which case the color image may first be converted to greyscale image to facilitate the identification of dark region(s) based on image intensity values. As shown in the example, light intensity thresholding may be applied to the greyscale image to identify a dark region 1601. In some instances, the intensity threshold value may be a constant. In some instances, the intensity threshold value may be a variable, and may be adjusted based on any of a variety of pre-determined algorithms. For example, the intensity threshold value may be adjusted iteratively until the identified dark region reaches a specified area (e.g., 1% of the total image area). Alternatively, the intensity threshold may be determined as a function of the local image intensity, overall average image intensity, or other image parameters. In some cases, one or more candidate dark regions may be detected as a result of intensity thresholding. These candidate dark regions may then be analyzed to select a single dark region as the lumen center. The dark region corresponding to the center of the lumen may be selected from the one or more candidate dark regions, for example, based on a calculation of confidence level for each candidate dark region and/or the proximity of the location of the dark region to the previously determined lumen center location. The confidence level may be represented by a confidence score computed using, for example, the method described in FIG. 5C. Once a specific dark region is selected, a center-of-mass calculation for the dark region may be used to determine the location of the lumen center.

Figure 17:
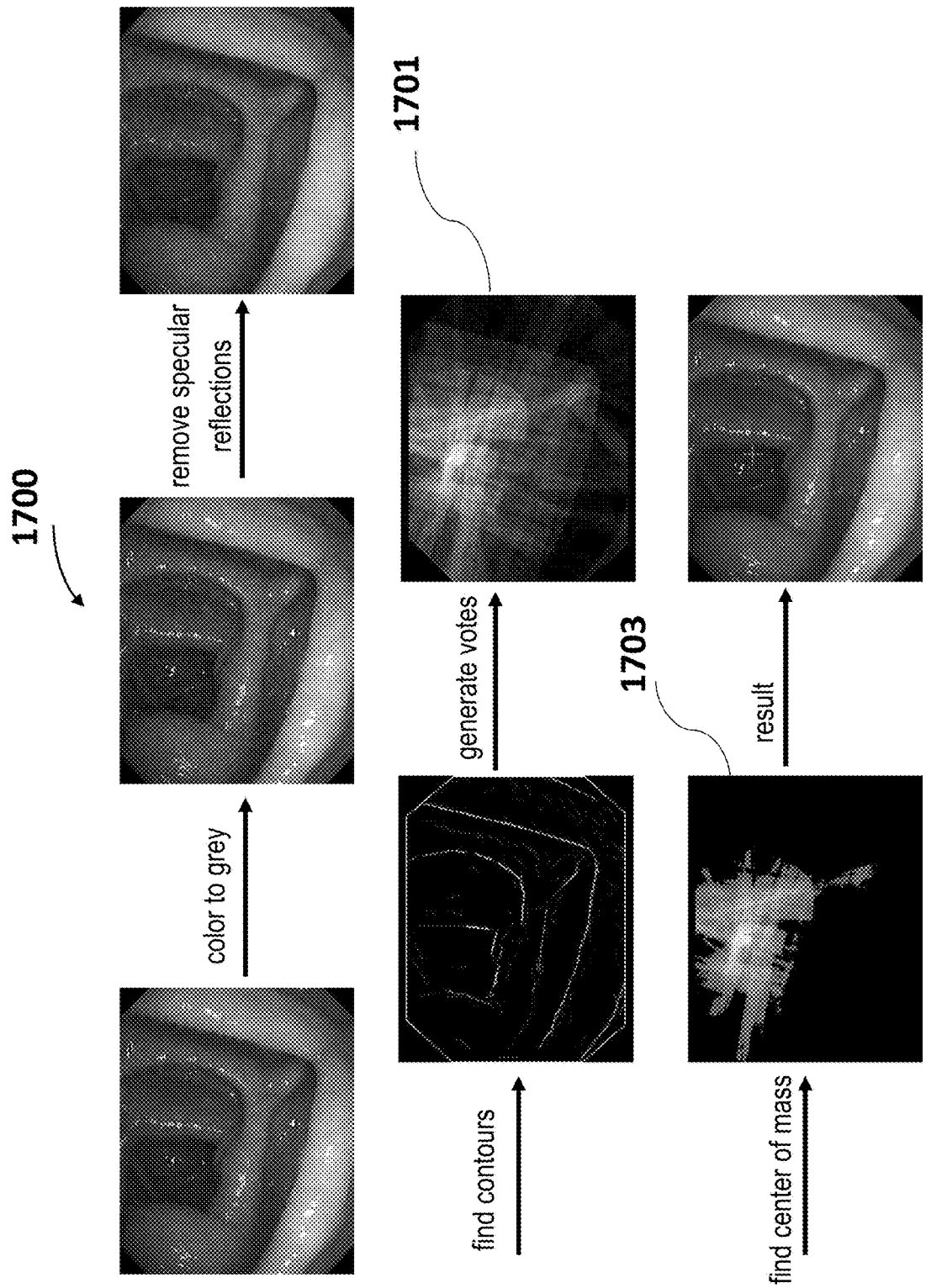
FIG. 17 illustrates the steps of an image processing method used to identify patterns within an image of, for example, a colon lumen, and subsequently identify the position of the center of the colon lumen.

Referring back to FIG. 15, a mucosal pattern method 1509 may be used to derive the location of the lumen center within an image and/or a confidence level for the determination of the location of the lumen center 1519. The steps involved in implementing this process are illustrated in FIG. 17. If the input image data comprises color image frames, then a first step in the process may be to transform the color image to a greyscale image. The greyscale image may then be processed to remove specular reflections and/or identify contours within the image. Any of a variety of edge detection or pattern detection algorithms known to those of skill in the art may be utilized in identifying contours, e.g., a Hough Transform and the like. The detected contours are then further analyzed to identify the location of the lumen center. In some cases, the lumen center may be identified by finding the intersection of the normal vectors for each of a series of contour segments. For example, as shown in FIG. 17, a normal vector may be generated for each segment of each of the one or more contours identified, where the normal vector is a vector that is perpendicular to the local segment of the contour and passes through the segment. A "vote" is generated for each normal vector that passes through a given pixel of the image, and the total number of votes for a given pixel equals the total number of normal vectors passing through that pixel. The lumen center may be identified as the area of the image comprising the highest vote count, i.e., the highest number of normal vectors counted per pixel. Image 1701 shows an example of the normal vectors generated for each segment of the detected contours, where the intensity of the image corresponds to the vote count for each pixel. The contours may be segmented using any of a variety of techniques. For example, each segment may comprise one pixel, two pixels, three pixels, and the like, of a given contour. In another example, a segment may be defined by locally fitting a straight line segment to the given contour.

In some cases, a threshold may be applied to the vote count in image 1701 before computing the location of the lumen center. For instance, a threshold may be applied to remove pixels that have a vote count below a threshold value. For example, points or pixels having a vote count of less than or equal to a value of three may be removed, thereby resulting in a thresholded vote count image 1703. In some cases, the center-of-mass of the pixel region identified in the thresholded vote count image 1703 may be computed and used as the location of the lumen center. In some embodiments, a confidence level for the determination of the lumen center position may also be calculated. In some cases, the confidence level may be computed based on a moment of inertia calculation for the vote count image 1701 or for the thresholded vote count image 1703.

Again referring back to FIG. 15, in some embodiments a light intensity gradient method 1511 may be used to process a captured image frame 1501 and generate light intensity gradient data 1521. The light intensity gradient method utilized may be the same method as described in FIG. 6B. In some embodiments, an optical flow method 1513 may be used to process the captured image frame 1501 and a previous image frame 1503 to generate a motion vector 1523. Optical flow methods detect the pattern of apparent motion of image object(s) between two consecutive frames that are caused by the movement of, in this case, the camera and generate a two-dimensional vector field, where each vector is a displacement vector showing the movement of specific points in the image from the first frame to the second frame.

To date, no single image processing method has proven reliable enough to accurately determine the location of the lumen center, or an estimate of the direction in which it lies, from image data that may often include variations in lighting intensity, specular reflections, foreign objects, etc. Typically, different image processing algorithms tend to perform well under certain conditions, and poorly under others, where the conditions for performing well may vary according to which image processing algorithm is employed. For example, the dark region detection method described above may perform poorly for images in which stool fragments, blood, or shadows are present, while the mucosal pattern detection method may perform poorly for images in which there is little or no mucosal pattern visible, e.g., near the rectum, at points of splenic flexure, or in samples of pig's colon used for ex vivo trials.

In the present example, a combination of image processing methods was used to improve the accuracy of determining the location of the lumen center and calculating confidence levels, as well as the reliability of the determination of navigation direction and/or steering control instructions provided by an ANN. Seven videos of actual colonoscopy procedures were collected using an Olympus colonoscope, and 805 video clips of 2 seconds each in length were extracted from them. Most of the images in these video clips show the lumen within the field-of-view. A custom training program was used to display the video images to a surgeon, and enabled the surgeon to click on a position within the image to indicate where the colonoscope should be directed based on the surgeon's past experience in performing colonoscopies. Approximately 80% of the data generated from the video clips was used to train the ANN, while the remaining 20% was used to evaluate the performance of the system.

Figure 18:
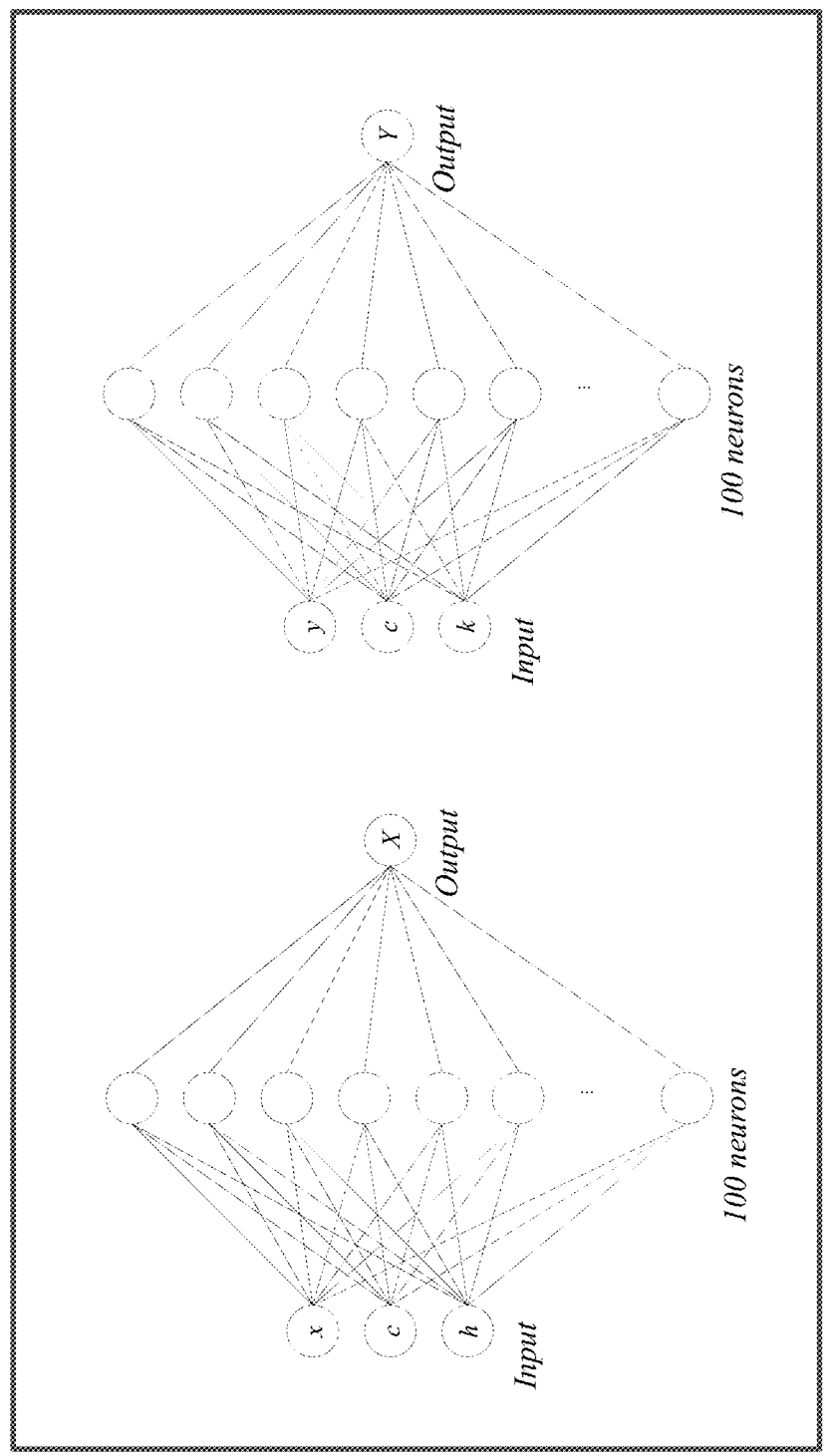
FIG. 18 illustrates a "twin" ANN model used to process image data and determine a steering direction and/or set of steering control instructions for a robotic endoscope.

A "twin" ANN model (FIG. 18) was used for the purpose of capturing the "logic" used by surgeons in steering a colonoscope, and was trained to map the image-derived input data to output values for navigation direction. The input data comprised values for the location of the lumen center (x, y) and confidence level (c) of the combined lumen detection method, and the light gradient (h, k), while as noted, the output data comprises values for the target steering position (X, Y). The input ranges for ANN hyper-parameter values were: (i) 1-3 hidden layers, and (ii) 3-1,000 nodes (neurons) per layer. The values for the ANN hyper-parameters following optimization of the network were 1 hidden layer, and 100 nodes per layer.

Figure 19:
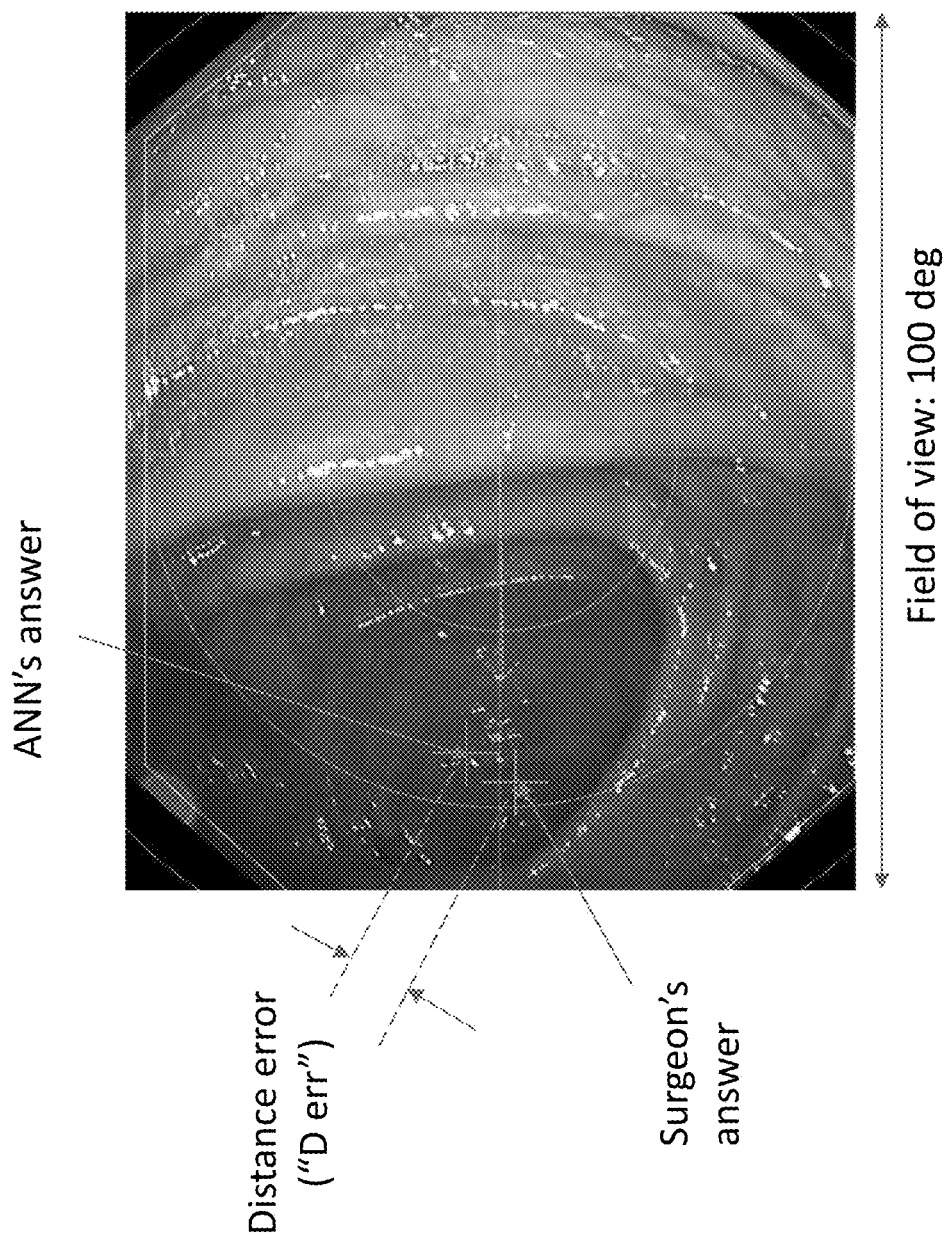
FIG. 19 shows an image of the interior of the colon and illustrates the definition of the error measurement, $D_{err}$, used to evaluate performance of a prototype system.

The performance of the ANN-based automated steering direction method was evaluated by comparing the separation distance, $D_{err}$ (in units of degrees), between the surgeon's indicated location for the lumen center and that determined by the ANN, as indicated in FIG. 19.

Figure 20:
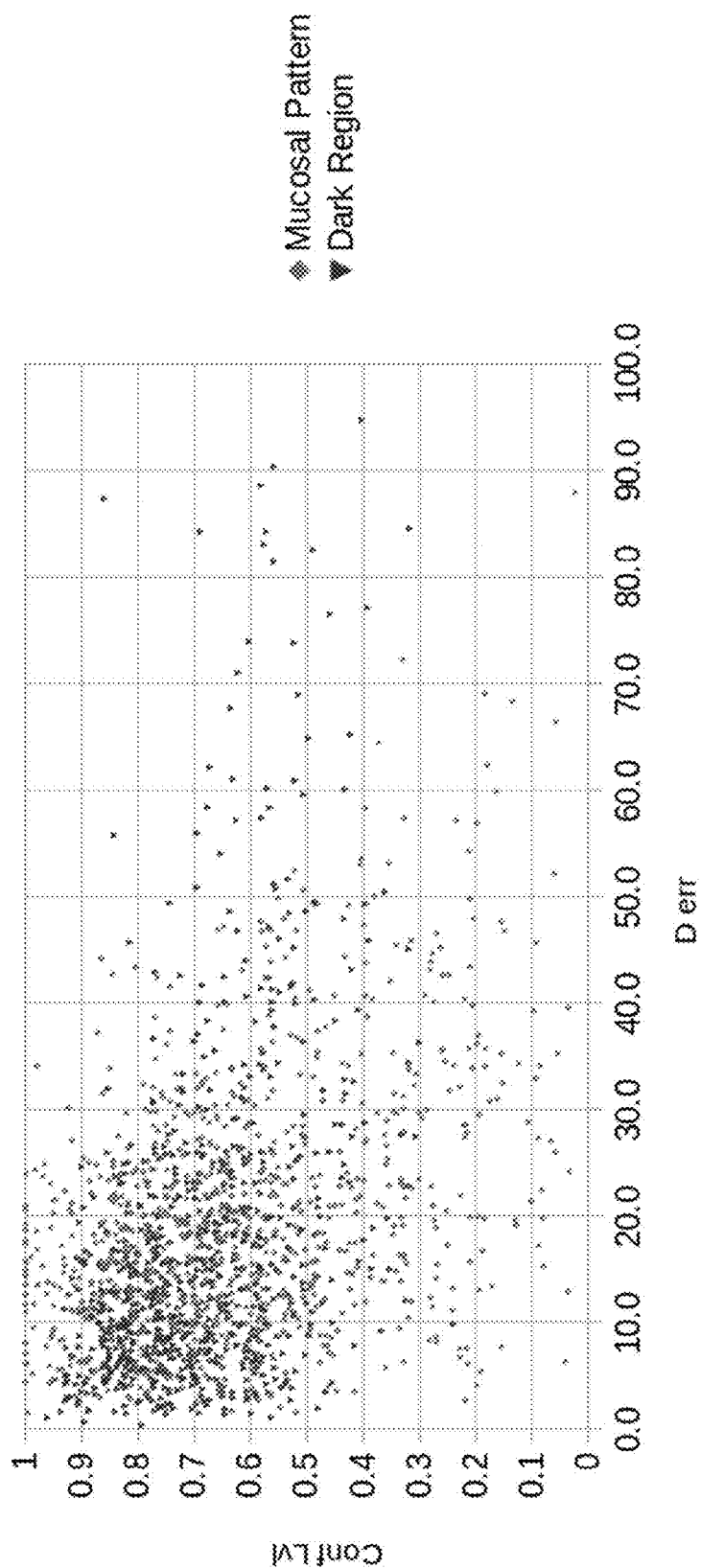
FIG. 20 shows an example of a scatter plot of confidence level data versus Derr.
Figure 21:
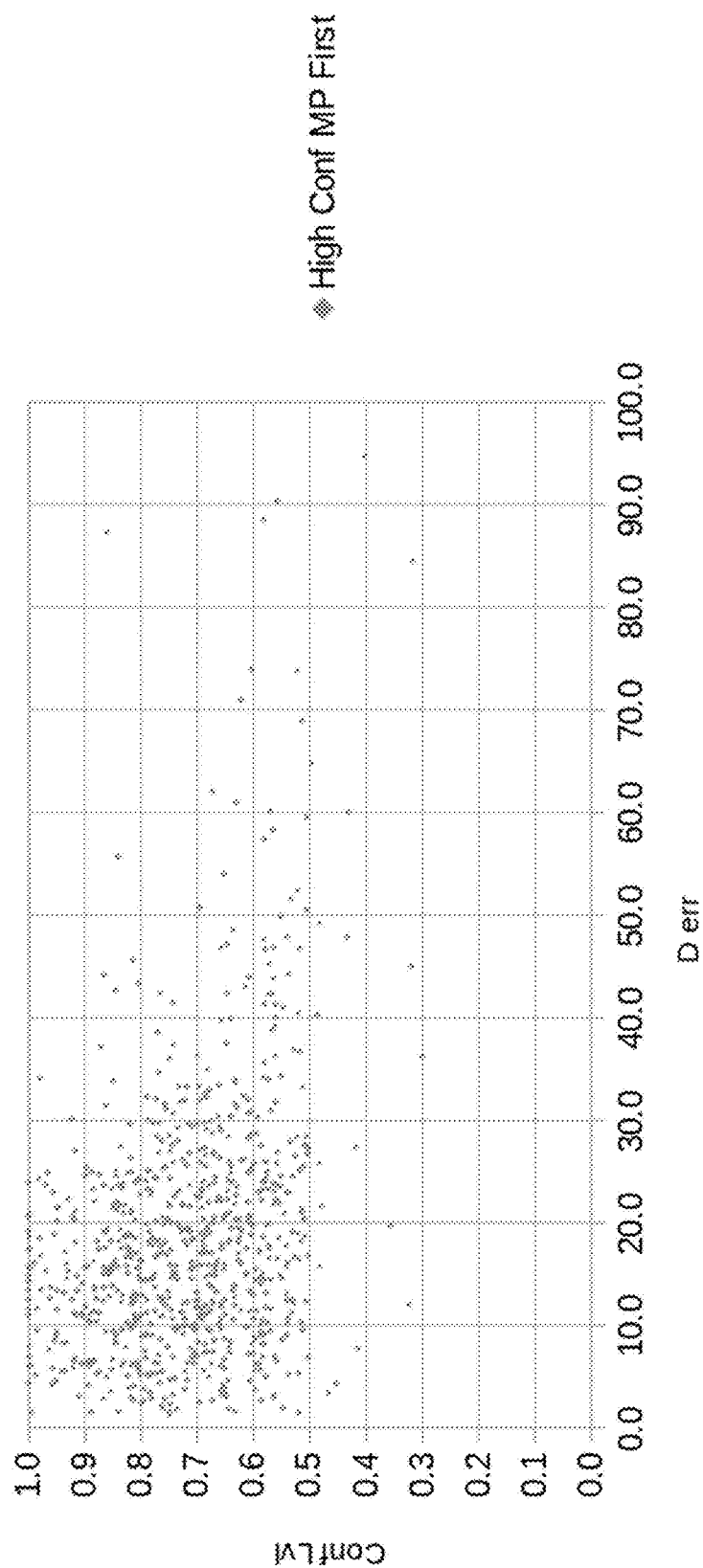
FIG. 21 shows an example of a scatter plot of confidence level data versus Derr.
Figure 22:
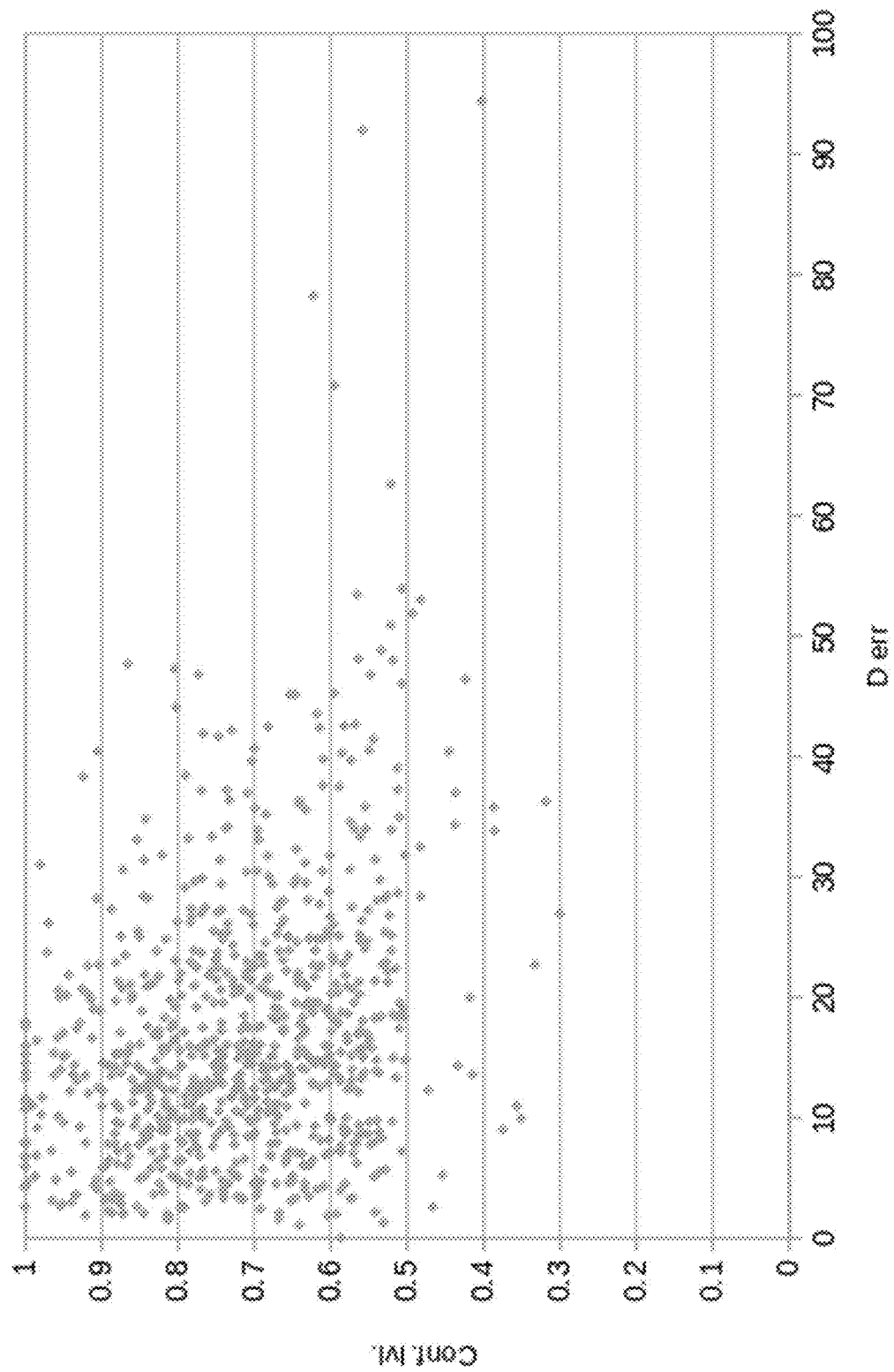
FIG. 22 shows an example of a scatter plot of confidence level data versus Derr.

The results of the comparison between a surgeon's indicated location for the lumen center and that predicted by different combinations of image processing and ANN-based analysis are summarized in FIGS. 20-22. FIG. 20 shows a scatter plot of confidence level data versus $D_{err}$, where the confidence levels and values of $D_{err}$ were determined using only the dark region detection or the mucosal pattern detection method. FIG. 21 shows a scatter plot of confidence level data versus $D_{err}$, where the confidence levels and values of $D_{err}$ were determined using a combination of the dark region detection and mucosal pattern detection methods. In the example of results shown in FIG. 21, the result obtained with the mucosal pattern detection method was used if the confidence level was greater than 0.5, otherwise the result obtained using the dark region detection method was used. Note that the individual data points are much more tightly clustered than those plotted in FIG. 20. Any of a variety of alternative approaches could be used to combine the results obtained using two or more different image processing methods, for example, a weighted average of the predicted X and Y positions for the lumen center and/or a weighted average of the confidence levels calculated for the results of the individual image processing methods could be used. FIG. 22 shows a scatter plot of confidence level data versus $D_{err}$, where the confidence levels and values of $D_{err}$ were determined using a combination of the dark region detection, mucosal pattern detection, and light intensity gradient methods, where the image-derived data were further processed using the ANN. The individual data points plotted in FIG. 22 are somewhat more tightly clustered than those plotted in FIG. 21 (mean $D_{err}$=17.2 degrees for the former compared to 18.3 degrees for the latter). The extent to which this indicates significant improvement is difficult to determine at present, as there are currently no general standards available regarding maximum allowable error and the value of maximum allowable error is likely to be case dependent. According to a surgeon involved in this study, human error may vary from 2 degrees to 30 degrees depending on the specific case (and may be higher for extreme cases). Current development work is focused on improving the combination of image processing algorithms utilized, e.g., by incorporation of optical flow methods, as well as on improving the design of the ANN model and improving the quantitative methods used for validation of the process.

As noted above, in some embodiments the machine learning algorithm utilized for processing the input image data (or data derived from the image data using one or more image processing algorithms) and mapping it to an output comprising a determination of navigational direction and/or a set of steering control instructions may be an artificial neural network.

Figure 23:
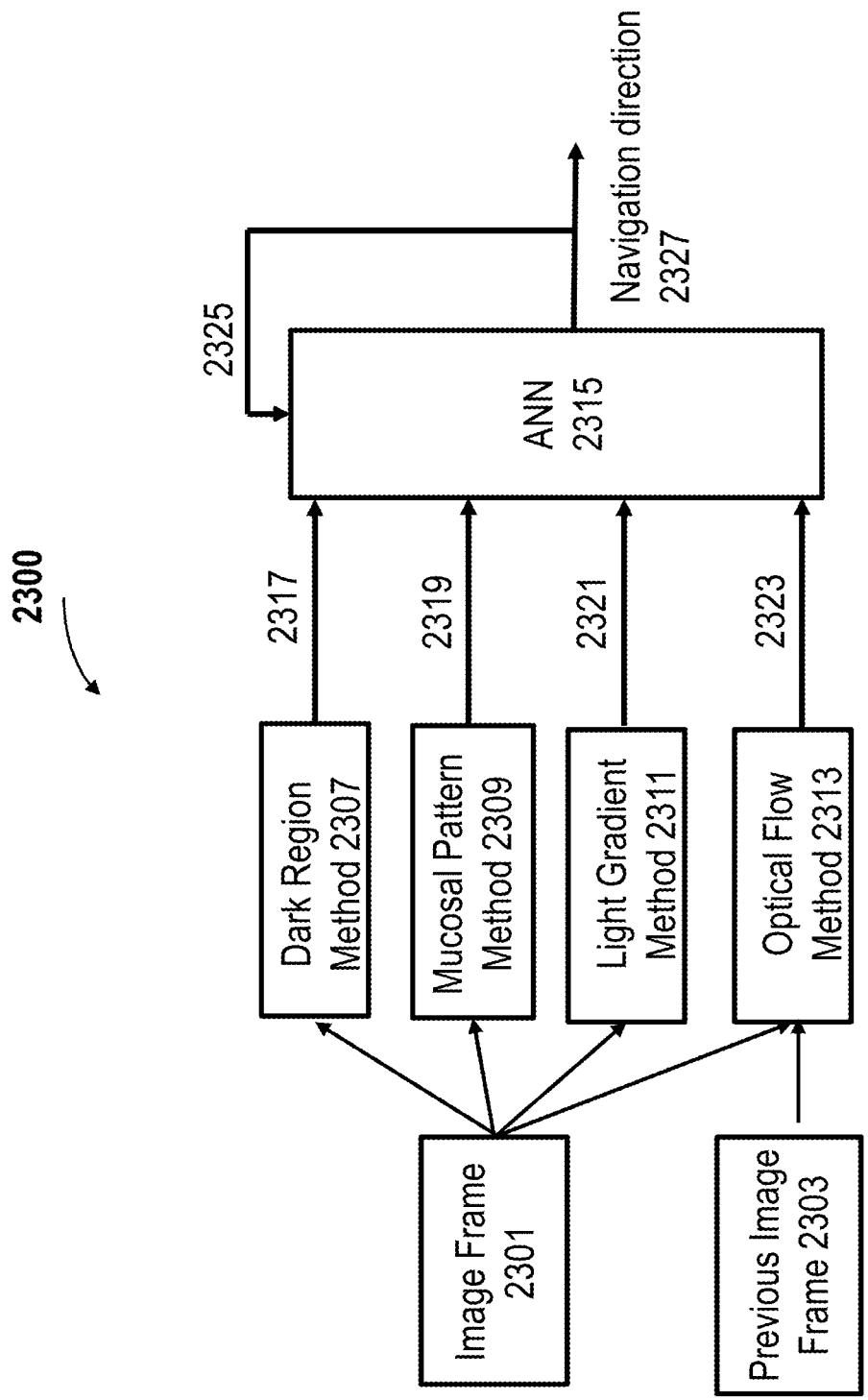
FIG. 23 shows a block diagram of an exemplary adaptive steering control system for a robotic endoscope that uses data collected by image sensors to generate a steering control signal, where the image data is processed using two or more image processing algorithms and subsequently used as input for a recurrent neural network that maps the input data to a navigation direction and/or set of steering control instructions.

Prophetic Example—Use of Recurrent Neural Networks or Recurrent Convolutional Neural Networks for Automated Steering Control of a Robotic Endoscope In some embodiments, the artificial neural network employed in the steering control method 2300 may comprise a recurrent neural network 2315, as illustrated in FIG. 23, such that at least part of the output data 2327 may be supplied back to the network as input data 2325. A recurrent neural network (RNN) is a class of artificial neural network where connections between nodes form a directed cycle that allows the network to exhibit dynamic temporal behavior and use its internal memory to process arbitrary sequences of inputs. Any of a variety of RNN algorithms known to those of skill in the art may be utilized. Fully recurrent neural networks are networks of nodes each having a directed (one-way) connection to every other node and each having a time-varying real-valued activation threshold. Each connection between nodes has an adjustable real-valued weighting factor. Nodes may be either input nodes (i.e., that receive data from outside the network), output nodes (i.e., that yield results), or hidden nodes (i.e., that modify the data as it transits from input to output). As shown in FIG. 23, the input data may comprise image-derived data 2317, 2319, 2321, 2323, or any combination thereof, and at least part of the output data 2325. In some cases, the at least part of the output data 2325 may comprise a confidence level for having correctly determined the location of the lumen center as analyzed by the recurrent neural network 2315. In some cases, the at least part of the output data 2325 may comprise the lumen center location. In other cases, the at least part of the output data 2325 may comprise both the lumen center location and the confidence level.

For supervised learning using paired sets of input data and known output values (i.e., the correct navigation direction and/or sets of steering control instruction) at discrete times, sequences of real-valued input vectors arrive at the input nodes, one vector at a time. At any given time step, each non-input node computes an output result as a nonlinear function of the weighted sum of the intermediate inputs provided by all nodes that connect to it, and weighting factors and/or other parameters are subsequently adjusted step-by-step to reliably map input data to the correct output. For reinforcement learning, a fitness function (or "reward function") is used to train the network rather than paired sets of input and output data. Weighting factors and/or other parameters are adjusted in order to maximize the value of the fitness or reward function. Each sequence of input vectors produces an error value comprising the sum of the deviations between the target output data values and the corresponding output data values computed by the network. For a training set comprising a plurality of input vector sequences, the total error is the sum of the errors for all individual input vectors.

In one non-limiting example of the use of an RNN for automated steering control of a robotic endoscope, the input to the RNN algorithm may comprise image-derived data obtained by using a combination of at least four image processing methods. For example, the input data for the RNN may comprise image derived data obtained using a combination of the dark region detection method, the mucosal pattern detection method, the light intensity gradient method, and an optical flow method. For each image frame, the dark region method may be used with iterative thresholding to identify up to 3 dark regions or candidates for the position of the lumen center. For each candidate region i, one may calculate a set of parameters $\{X_{DRi}, Y_{DRi}, I_{DRi}, M_{DRi}\}$ where $\{X_{DRi}, Y_{DRi}\}$ is the location of the center-of-mass, $I_{DRi}$ is the relative mean intensity (calculated as (mean intensity for candidate region/mean intensity for entire image); a confidence level factor for this method), and $M_{DRi}$ is the normalized moment of inertia (calculated as (moment of inertia for candidate region/area of candidate region/mean intensity of candidate region); another confidence level factor for this method).

Similarly, for each image frame, the mucosal pattern method may be used to calculate a set of parameters $\{X_{MP}, Y_{MP}, I_{MP}, M_{MP}\}$, where $\{XMP, YMP\}$ is the location of the center-of-mass of the thresholded vote counts, $I_{MP}$ is the mean vote value (calculated as (sum of vote values for all pixels in the entire image/area of the entire image); a confidence level factor for this method, as more votes means more pattern to rely on), and My is the normalized moment of inertia of the thresholded votes (calculated as (moment of intertia for the thresholded votes/mean vote count value for the thresholded votes/area of thresholded votes); a confidence level factor for this method).

For each image frame, the light intensity gradient method may be used to calculate a set of parameters $\{X_{LG}, Y_{LG}\}$, which are the X and Y components of the normalized intensity gradient (calculated as (gradient/max possible value of gradient).

For each image frame and the previous image frame, the optical flow method may be used to calculate a set of parameters $\{X_{OF}, Y_{OF}, S_{OF}, T_{OF}\}$, which are the X-translation, Y-translation, scale, and rotation respectively calculated by comparing the two frames.

To summarize, the input to the RNN is a 14-component vector: $\{X_{DRi}, Y_{DRi}, I_{DRi}, M_{DRi}, X_{MP}, Y_{MP}, I_{MP}, M_{MP}, X_{LG}, Y_{LG}, X_{OF}, Y_{OF}, S_{OF}, T_{OF}\}$ and the network is trained using one or more sets of training data as described elsewhere herein.

Figure 24:
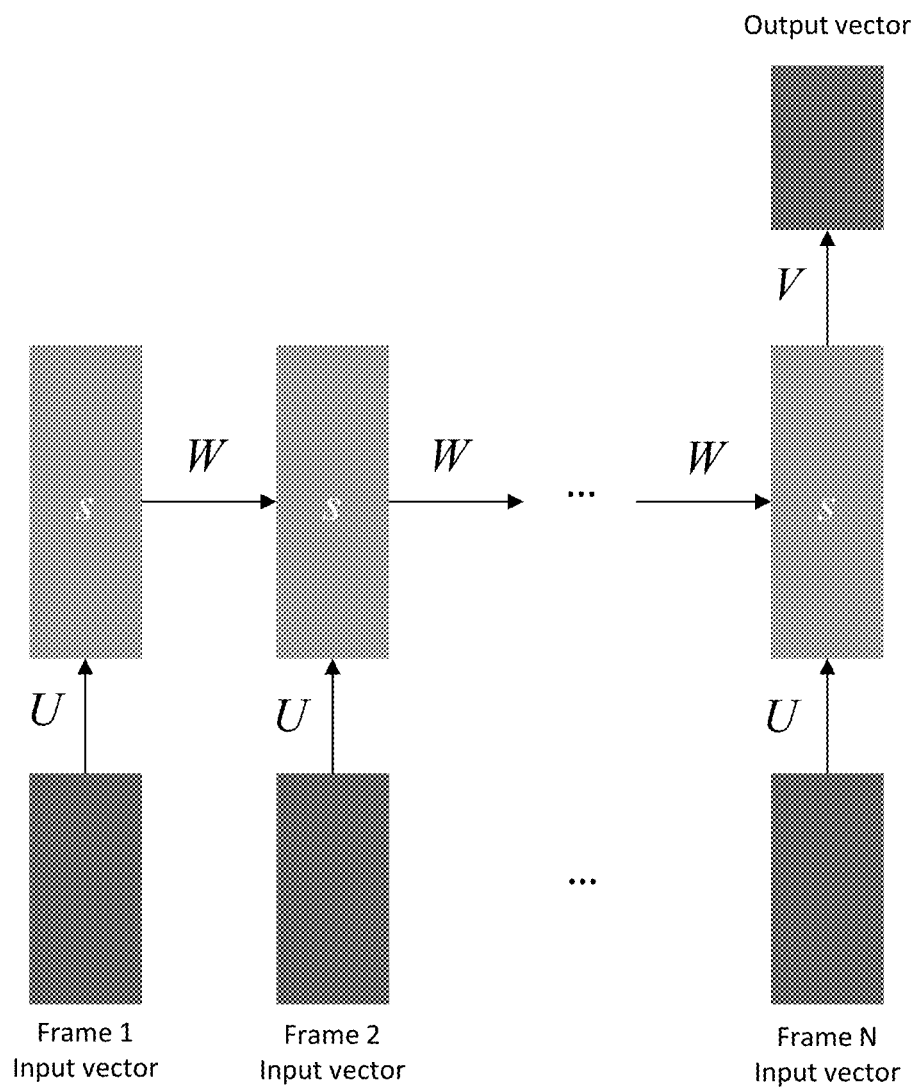
FIG. 24 illustrates the architecture and adjustable parameters comprising a recurrent neural network (RNN).

The architecture and adjustable parameters of the RNN are further illustrated in FIG. 24. In this figure, rectangles indicate vectors, arrows indicate a matrix multiplication step, those rectangles labeled with an "s" indicate the temporal "memory" of the network, and the symbols U, V, and W indicate different matrices of weighting factors to be trained. The number of image frames (N) to be utilized will be determined as part of the training process. N will likely be chosen to cover at least 2 seconds of video, but frame rate is to be determined based on the computational resources available. The dimensions of the U, V, and W matrices depend on that of s, which in turn is to be determined based on optimizing the model to find a suitable compromise between under-fitting and over-fitting. The simple RNN model illustrated in the figure may be upgraded to use more vertical layers, or may be replaced with a more effective model, e.g., an LSTM (an RNN composed of long short-term memory (LSTM) units), a GRU (an RNN composed of gated recurrent (GRU) units), etc.

Figure 25:
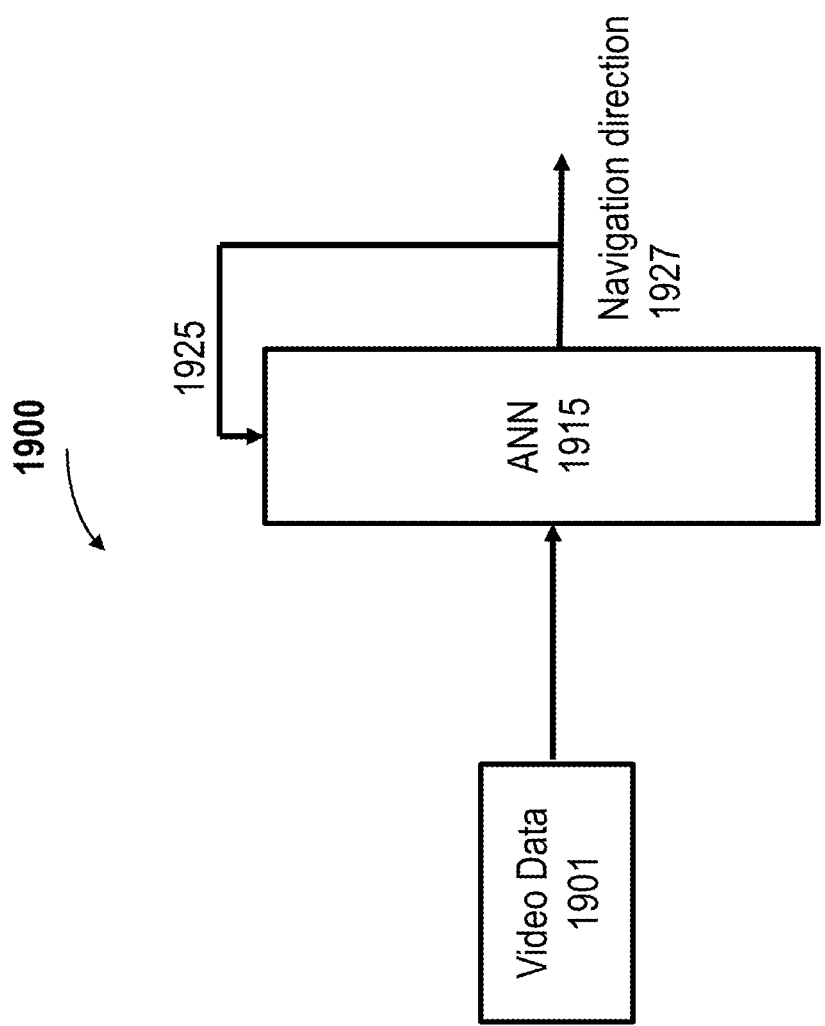
FIG. 25 shows a block diagram of an exemplary adaptive steering control system for a robotic endoscope that uses data collected by image sensors to generate a steering control signal, where the image data is processed directly by a recurrent convolutional neural network that maps the input data to a navigation direction and/or set of steering control instructions.

In some cases, the recurrent network may be a recurrent convolutional neural network (RCNN), as illustrated in FIG. 25. In this example, video image data may be used directly as input to the machine learning algorithm, and the neural network is allowed to formulate the logical processing steps that provide optimal mapping of the input data to an output navigational direction and/or set of steering control instructions.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:

1. A control system for providing an adaptive steering control output signal for steering a robotic endoscope, the control system comprising:
   a) a first image sensor configured to capture a first input data stream comprising a series of two or more images of a lumen; and
   b) one or more processors that are individually or collectively configured to:
      i) perform automated image processing and feature extraction on one or more of the images using a combination of at least two different image processing algorithms simultaneously to generate an input data set comprising at least two different estimates of a location of a lumen center;
      ii) output a steering direction based on an analysis of the input data set using an artificial neural network that has been trained using a training data set, the training data set comprises recorded image data from previous endoscopic procedures and empirical steering control instructions provided to a virtual steering mechanism by a surgeon or other skilled operator during simulated endoscopic procedures, wherein the steering direction adapts to changes in the input data set in real time, and wherein the steering direction need not be aligned with the estimated location (s) of the lumen center; and
      iii) generate the adaptive steering control output signal in real time.

2. The control system of claim 1, wherein the first input data stream comprises video data.

3. The control system of claim 1, wherein the automated image processing and feature extraction further comprises a determination of the location of a wall of the lumen, a determination of the location of an obstacle, a calculation of a confidence level for determining the location of the center of the lumen, a determination of a loss of or change in the integrity of lumen center position data, or any combination thereof.

4. The control system of claim 1, wherein the center of the lumen is not visible within the one or more images, and a predicted position for the center of the lumen is calculated based on motion vectors derived from the center positions of the lumen in two or more images previously captured by the first image sensor.

5. The control system of claim 1, wherein the automated image processing comprises identifying areas of high light reflection and thereby determining the proximity of a lumen wall or an obstacle to a distal end of the robotic endoscope based on a relationship between light reflection and proximity.

6. The control system of claim 1, wherein one estimate of the location of the center of the lumen comprises: (i) generating a plurality of vectors, where each vector is aligned in a direction that is normal to a local segment of a contour identified in an image, and (ii) counting the number of vectors that intersect a given pixel in the image.

7. The control system of claim 1, wherein the one or more processors are further configured to generate the adaptive steering control output signal to direct the robotic endoscope to search along a specified route within the lumen when a confidence level for determining the location of the center of the lumen relative to a distal end of the robotic endoscope is below a first threshold, and to repeat the steps of:
   (i) performing automated image processing and feature extraction on one or more images of at least the first input data stream to identify the center position of the lumen,
   (ii) calculating a new confidence level for the determination of the location of the center of the lumen, and
   (iii) generating the steering control output signal to direct the robotic endoscope to search along the specified route until the new confidence level is above a second threshold.

8. The control system of claim 7, wherein the confidence level is calculated based on an intensity calculation, a moment of inertia calculation, and/or a convexity calculation for the location of the center of the lumen determined from the first input data stream.

9. The control system of claim 7, wherein the specified route is a pre-determined route for steering the distal end of the robotic endoscope selected from the group consisting of a spiral search pattern, a rectilinear grid search pattern, a circular search pattern, or any combination thereof.

10. The control system of claim 1, wherein the at least two different image processing algorithms are selected from the group consisting of a dark region method, a mucosal pattern method, a light gradient method, and an optical flow method.

11. The control system of claim 1, further comprising a second image sensor that is used in conjunction with the first image sensor to provide a stereoscopic image stream that comprises depth information about the lumen proximal to a distal end of the robotic endoscope.

12. The control system of claim 1, wherein one of the at least two different image processing algorithms comprises an optical flow method.

13. The control system of claim 1, wherein the artificial neural network is trained using a training dataset that comprises simulated image data, wherein the simulated image data comprises an adjustment to one or more properties of the recorded image data.

14. The control system of claim 1, wherein the artificial neural network comprises a convolutional neural network.

15. The control system of claim 1, wherein the artificial neural network comprises a recurrent neural network.

16. The control system of claim 1, wherein the recurrent neural network comprises a recurrent convolutional neural network.

17. A method for providing an adaptive steering control output signal for steering a robotic endoscope, the method comprising:
   a) providing a first input data stream comprising a series of two or more images of a lumen;
   b) performing automated image processing and feature extraction on one or more of the images using a combination of at least two different image processing algorithms simultaneously to generate an input data set comprising at least two different estimates of a location of a lumen center;
   c) outputting a steering direction based on an analysis of the input data set using an artificial neural network that has been trained using a training data set, the training data set comprises recorded image data from previous endoscopic procedures and empirical steering control instructions provided to a virtual steering mechanism by a surgeon or other skilled operator during simulated endoscopic procedures, wherein the steering direction adapts to changes in the input data set in real time, and wherein the steering direction need not be aligned with the estimated location(s) of the lumen center; and d) generating the adaptive steering control output signal in real time.

18. The method of claim 17, wherein the first input data stream comprises video data.

19. The method of claim 17, wherein the automated image processing and feature extraction further comprises a determination of the location of a wall of the lumen, a determination of the location of an obstacle, a calculation of a confidence level for determining the location of the center of the lumen, a determination of a loss of or change in the integrity of lumen center position data, or any combination thereof.

20. The method of claim 17, wherein the center of the lumen is not visible within the one or more images, and a predicted position for the center of the lumen is calculated based on motion vectors derived from the center positions of the lumen in two or more images previously captured by a first image sensor.

21. The method of claim 17, wherein the automated image processing comprises identifying areas of high light reflection and thereby determining the proximity of a lumen wall or an obstacle to the distal end of the robotic endoscope based on a relationship between light reflection and proximity.

22. The method system of claim 17, wherein one estimate of the location of the center of the lumen comprises: (i) generating a plurality of vectors, where each vector is aligned in a direction that is normal to a local segment of a contour identified in an image, and (ii) counting the number of vectors that intersect a given pixel in the image.

23. The method of claim 17, further comprising generating a steering control output signal to direct the robotic endoscope to search along a specified route within the lumen when a confidence level for determining the location of the center of the lumen relative to the distal end of the robotic endoscope is below a first threshold, and repeating the steps of:
   (i) performing automated image processing and feature extraction on one or more images of at least the first input data stream to identify the center position of the lumen,
   (ii) calculating a new confidence level for the determination of the location of the center of the lumen, and
   (iii) generating the steering control output signal to direct the robotic endoscope to search along the specified route until the new confidence level is above a second threshold.

24. The method of claim 23, wherein the confidence level is calculated based on an intensity calculation, a moment of inertia calculation, and/or a convexity calculation for the location of the center of the lumen determined from the first input data stream.

25. The method of claim 23, wherein the specified route is a pre-determined route for steering the distal end of the robotic endoscope selected from the group consisting of a spiral search pattern, a rectilinear grid search pattern, a circular search pattern, or any combination thereof.

26. The method of claim 17, wherein the at least two different image processing algorithms are selected from the group consisting of a dark region method, a mucosal pattern method, a light gradient method, and an optical flow method.

27. The method of claim 17, further comprising providing a second input data stream comprising a series of two or more images of the lumen, and wherein the automated image processing of step (b) is applied to both the first input data stream and the second input data stream and provides a stereoscopic image stream that comprises depth information about the lumen proximal to a distal end of the robotic endoscope.

28. The method of claim 17, wherein one of the at least two different image processing algorithms comprises an optical flow method.

29. The method of claim 17, wherein the artificial neural network is trained using a training dataset that comprises simulated image data, wherein the simulated image data comprises an adjustment to one or more properties of the recorded image data.

30. The method of claim 17, wherein the artificial neural network comprises a convolutional neural network.

31. The method of claim 17, wherein the artificial neural network comprises a recurrent neural network.

32. The method of claim 17, wherein the recurrent neural network comprises a recurrent convolutional neural network.

33. A robotic endoscope, comprising:
a) an elongated body structure comprising one or more actuation units and a steerable distal portion; and
b) a control system comprising:
   i) a first image sensor configured to capture a first input data stream comprising a series of two or more images of a lumen; and
   ii) one or more processors that are individually or collectively configured to:
      i) perform automated image processing and feature extraction on one or more of the images using a combination of at least two different image processing algorithms simultaneously to generate an input data set comprising at least two different estimates of a location of a lumen center;
      ii) output a steering direction based on an analysis of the input data set using an artificial neural network that has been trained using a training data set, the training data set comprises recorded image data from previous endoscopic procedures and empirical steering control instructions provided to a virtual steering mechanism by a surgeon or other skilled operator during simulated endoscopic procedures, wherein the steering direction adapts to changes in the input data set in real time, and wherein the steering direction need not be aligned with the estimated location(s) of the lumen center; and
      iii) generate an adaptive steering control output signal to control the one or more actuation units in real time.

34. The robotic endoscope of claim 33, wherein the elongated body structure further comprises one or more wires that are driven by the one or more actuation units to steer the steerable distal portion.

35. The robotic endoscope of claim 33, wherein the elongated body structure comprises an elongated elastomeric body structure.

36. The robotic endoscope of claim 33, wherein the automated image processing and feature extraction further comprises a determination of the location of a wall of the lumen, a determination of the location of an obstacle, a calculation of a confidence level for determining the location of the center of the lumen, a determination of a loss of or change in the integrity of lumen center position data, or any combination thereof.

37. The robotic endoscope system of claim 33, wherein the control system comprises a second image sensor that is used in conjunction with the first image sensor to provide a stereoscopic image stream that comprises depth information about the lumen proximal to a distal end of the robotic endoscope.

38. The robotic endoscope of claim 33, wherein one of the at least two different image processing algorithms comprises an optical flow method.

39. The robotic endoscope of claim 33, wherein the artificial neural network is trained using a training dataset that comprises simulated image data, wherein the simulated image data comprises an adjustment to one or more properties of the recorded image data.

40. The robotic endoscope of claim 33, wherein the artificial neural network comprises a convolutional neural network.

41. The robotic endoscope of claim 33, wherein the artificial neural network comprises a recurrent neural network.

42. The robotic endoscope of claim 33, wherein the recurrent neural network comprises a recurrent convolutional neural network.

* * * * *